United States Patent
Biggins et al.

(10) Patent No.: US 11,749,375 B2
(45) Date of Patent: Sep. 5, 2023

(54) HUMAN THERAPEUTIC TARGETS AND MODULATORS THEREOF

(71) Applicant: LIFEMINE THERAPEUTICS, INC., Cambridge, MA (US)

(72) Inventors: John Baxter Biggins, Long Beach, NY (US); Brian Roger Bowman, New Rochelle, NY (US); Gregory L. Verdine, Boston, MA (US)

(73) Assignee: LIFEMINE THERAPEUTICS, INC., Cambridge, MA (US)

( * ) Notice: Subject to any disclaimer, the term of this patent is extended or adjusted under 35 U.S.C. 154(b) by 730 days.

(21) Appl. No.: 16/646,978

(22) PCT Filed: Sep. 14, 2018

(86) PCT No.: PCT/US2018/051134
§ 371 (c)(1),
(2) Date: Mar. 12, 2020

(87) PCT Pub. No.: WO2019/055816
PCT Pub. Date: Mar. 21, 2019

(65) Prior Publication Data
US 2020/0211673 A1   Jul. 2, 2020

Related U.S. Application Data

(60) Provisional application No. 62/558,744, filed on Sep. 14, 2017.

(51) Int. Cl.
G16B 20/00 (2019.01)
G16B 35/10 (2019.01)

(52) U.S. Cl.
CPC ............ *G16B 20/00* (2019.02); *G16B 35/10* (2019.02)

(58) Field of Classification Search
CPC ................................ G16B 20/00; G16B 35/10
See application file for complete search history.

(56) References Cited

U.S. PATENT DOCUMENTS 6,432,648 B1 * 8/2002 Blumenfeld ........... G16B 20/20
536/23.5
8,065,089 B1   11/2011 Najarian
(Continued)

FOREIGN PATENT DOCUMENTS

WO   WO-2002/077179 A2   10/2002
WO   WO-2007/139871 A2   12/2007
(Continued)

OTHER PUBLICATIONS

Almeida, H. et al. (Nov. 27, 2020). "TOUCAN: A Framework For Fungal Biosynthetic Gene Cluster Discovery," NAR Genomics and Bioinformatics 2(4):1qaa098, 11 pages.
(Continued)

*Primary Examiner* — Eliyah S. Harper
(74) *Attorney, Agent, or Firm* — MORRISON & FOERSTER LLP

(57) ABSTRACT

Among other things, the present disclosure provides technologies for efficient and effective identification of ETaGs, for example, from fungi genomes. In some embodiments, provided technologies are particularly useful for identifying mammalian targets of biosynthetic products of fungi. In some embodiments, provided technologies are particularly useful for identifying and/or prioritizing human targets for drug development. In some embodiments, provided technologies are particularly useful for developing modulators for human targets based on biosynthetic products of fungi.

23 Claims, 40 Drawing Sheets

(56) References Cited

U.S. PATENT DOCUMENTS

| | | | |
|---|---|---|---|
| 2001/0039014 A1* | 11/2001 | Bass | C12N 15/1031 |
| | | | 702/20 |
| 2002/0164588 A1* | 11/2002 | Eisenberg | G16B 20/30 |
| | | | 435/6.16 |
| 2004/0058872 A1 | 3/2004 | Keller et al. | |
| 2004/0076981 A1* | 4/2004 | Yoder | C12Q 1/6895 |
| | | | 435/254.2 |
| 2006/0205017 A1 | 9/2006 | Handelsman et al. | |
| 2007/0003999 A1 | 1/2007 | Keller et al. | |
| 2009/0011476 A1 | 1/2009 | Hoffmeister et al. | |
| 2009/0191602 A1 | 7/2009 | Tang et al. | |
| 2009/0191636 A1* | 7/2009 | Ramage | C12N 15/8277 |
| | | | 435/469 |
| 2011/0076682 A1 | 3/2011 | Keller et al. | |
| 2011/0091454 A1 | 4/2011 | Diber et al. | |
| 2012/0190038 A1 | 7/2012 | Tang et al. | |
| 2012/0315680 A1 | 12/2012 | Tang et al. | |
| 2014/0273144 A1 | 9/2014 | Hawkins et al. | |
| 2015/0037862 A1 | 2/2015 | Keller et al. | |
| 2015/0203884 A1 | 7/2015 | Tang et al. | |
| 2015/0218531 A1 | 8/2015 | Tang et al. | |
| 2015/0310168 A1* | 10/2015 | Machida | G16B 40/00 |
| | | | 702/19 |
| 2016/0237443 A1 | 8/2016 | Keller et al. | |
| 2017/0029790 A1 | 2/2017 | Tang et al. | |
| 2017/0121719 A1 | 5/2017 | Oakley et al. | |
| 2018/0068062 A1 | 3/2018 | Zhang et al. | |
| 2019/0130999 A1 | 5/2019 | Oppenheim et al. | |
| 2019/0194098 A1 | 6/2019 | Cheung et al. | |
| 2020/0143907 A1 | 5/2020 | Engreitz et al. | |

FOREIGN PATENT DOCUMENTS

| | | |
|---|---|---|
| WO | WO-2011/044496 A2 | 4/2011 |
| WO | WO-2014/071182 A1 | 5/2014 |
| WO | WO-2017/100917 A1 | 6/2017 |
| WO | WO-2017/205387 A1 | 11/2017 |
| WO | WO-2018/094110 A2 | 5/2018 |
| WO | WO-2018/175635 A1 | 9/2018 |
| WO | WO-2019/055816 A1 | 3/2019 |

OTHER PUBLICATIONS

Bailey, T.L. et al. (May 7, 2015). "The MEME Suite," Nucleic Acids Res. 43(W1):W39-W49.

Baran, R.H. et al. (Oct. 2008, e-pub. Sep. 16, 2008). "Detecting Horizontally Transferred and Essential Genes Based on Dinucleotide Relative Abundance," DNA Research 15:267-276.

Bat-Erdene, U. et al. (May 2020, e-pub. Nov. 13, 2020). "Iterative Catalysis in the Biosynthesis of Mitochondrial Complex II Inhibitors Harzianopyridone and Atpenin B," J. Am. Chem. Soc. 142(19):8550-8554, 10 pages.

Blin, K. et al. (2021, e-pub. May 12, 2021). "antiSMASH 6.0: Improving Cluster Detection and Comparison Capabilities," Nucleic Acids Res. 49(W1):W29-W35.

Costanzo, M. et al. (Sep. 23, 2016, e-pub. Oct. 30, 2017). "A Global Genetic Interaction Network Maps a Wiring Diagram of Cellular Function," Science 353(6306):aaf1420, 34 pages.

Emms, D.M. et al. (2015, e-pub. Aug. 6, 2015). "OrthoFinder: Solving Fundamental Biases in Whole Genome Comparisons Dramatically Improves Orthogroup Inference Accuracy," Genome Biology 16:157, 14 pages.

Emms, D.M. et al. (2019, e-pub. Nov. 14, 2019). "OrthoFinder: Phylogenetic Orthology Inference for Comparative Genomics," Genome Biol. 20(1):238, 14 pages.

Fischbach, M. et al. (Dec. 2010, e-pub. Jan. 28, 2014). "Prokaryotic Gene Clusters: A Rich Toolbox For Synthetic Biology," Biotechnology Journal 5(12):1277-1296, 26 pages.

Gilchrist, C.L. et al. (2021). "Clinker & Clustermap.js: Automatic Generation of Gene Cluster Comparison Figures", Bioinformatics 37(16):2473-2475, 9 pages.

Gonzalez-Valbuena, E.E. et al. (2017, e-pub. Nov. 10, 2017). "Metrics to Estimate Differential Co-Expression Networks," BioData Mining 10:32, 1-15.

Heinz, S. et al. (May 28, 2010). "Simple Combinations of Lineage-Determining Transcription Factors Prime cis-Regulatory Elements Required for Macrophage and B Cell Identities," Mol Cell 38(4):576-589.

Katz, L. et al. (2016, e-pub. Jan. 6, 2016). "Natural Product Discovery: Past, Present, and Future," J Ind Microbiol Biotechnol. 43(2-3):155-176.

Kautsar, S.A. et al. (2020, e-pub. Oct. 15, 2019). "MIBiG 2.0: A Repository for Biosynthetic Gene Clusters of Known Function," Nucleic Acids Res. 48(D1):D454-D458.

Keller, N.P. (Mar. 2019). "Fungal Secondary Metabolism: Regulation, Function And Drug Discovery," Nature Reviews Microbiology 17(3):167-180, 38 pages.

Khaldi, N. et al. (Sep. 2010, e-pub. Sep. 1, 2011). "SMURF: Genomic Mapping Of Fungal Secondary Metabolite Clusters," Fungal Genetics and Biology 47(9):736-741, 13 pages.

Li, L. et al. (2003). "OrthoMCL: Identification of Ortholog Groups for Eukaryotic Genomes," Genome Res. 13(9):2178-2189.

Lim, F.Y. et al. (May 29, 2018). "Fungal Isocyanide Synthases and Xanthocillin Biosynthesis in Aspergillus Fumigatus," mBio 9(3):e00785-18, pp. 1-17.

Manni, M. et al. (Jul. 28, 2021). "BUSCO Update: Novel And Streamlined Workflows Along With Broader And Deeper Phylogenetic Coverage For Scoring Of Eukaryotic, Prokaryotic, And Viral Genomes," Molecular Biology And Evolution 38(10):4647-4654.

Medema, M.H. et al. (Jun. 14, 2011). "anti SMASH: Rapid Identification, Annotation and Analysis of Secondary Metabolite Biosynthesis Gene Clusters in Bacterial and Fungal Genome Sequences," Nucleic Acids Research 39:W339-W346.

Moreno-Hagelsieb, G. et al. (Feb. 1, 2008, e-pub. Nov. 26, 2007). "Choosing BLAST Options For Better Detection Of Orthologs As Reciprocal Best Hits," Bioinformatics 24(3):319-324.

Newman, D.J. et al. (Feb. 7, 2016). "Natural Products as Sources of New Drugs from 1981 to 2014," J. Nat. Prod. 79: 629-661.

Palazzotto, E. et al. (2018, e-pub. Apr. 12, 2018). "Omics And Multi-Omics Approaches To Study The Biosynthesis Of Secondary Metabolites In Microorganisms," Current Opinion In Microbiology 45:109-116.

Piel, J. (2009, e-pub. Dec. 5, 2008). "Metabolites From Symbiotic Bacteria," Natural Product Reports 26(3):338-362.

Scherlach, K. et al. (2021, e-pub. Jun. 23, 2021). "Mining and Unearthing Hidden Biosynthetic Potential", Nat Commun. 12(1):3864, 12 pages.

Sharp, P.M. et al. (1987). "The Codon Adaptation Index—A Measure of Directional Synonymous Codon Usage Bias, and Its Potential Applications," Nucleic Acids Res. 15(3):1281-1295.

Steenwyk, J.L. et al. (May 4, 2022). "An Orthologous Gene Coevolution Network Provides Insight Into Eukaryotic Cellular and Genomic Structure and Function," Sci. Adv. 8, eabn0105, 13 pages.

Tatusov, R.L. et al. (Oct. 24, 1997). "A Genomic Perspective on Protein Families," Science 278:631-637.

Trivedi, R. et al. (2020). "Substitution Scoring Matrices for Proteins—An Overview," Protein Science 29:2150-2163.

Wall, D.P. et al. (2007). "Ortholog Detection Using The Reciprocal Smallest Distance Algorithm," Methods Mol Biol. 396:95-110, 24 pages.

Wasil, Z. et al. (Aug. 13, 2018). "Oryzines A & B, Maleidride Congeners from Aspergillus oryzae and Their Putative Biosynthesis", J. Fungi 4:96, 12 pages.

Weber, T. et al. (2019). "antiSMASHS, antiSMASH Database Manual," an Introduction to Genome Mining Using antiSMASH, pp. 1-26.

Yan, Y. et al. (Jul. 1, 2020, e-pub. Jul. 1, 2021). "Recent Developments in Self-Resistance Gene Directed Natural Product Discovery," Nat Prod Rep. 37(7):879-892, 24 pages.

Abe, Y. et al., Effect of increased dosage of the ML-236B (compactin) biosynthetic gene cluster on ML-236B production in Penicillium citrinum, Mol. Genet. Genomics, 268(1):130-7 (2002).

(56) References Cited

OTHER PUBLICATIONS

Alanjary, M. et al., The Antibiotic Resistant Target Seeker (ARTS), an exploration engine for antibody cluster prioritization and novel drug target discovery, Nucleic Acids Research, 45:W42-W48 (2017).

Blin, K. et al., antiSMASH 4.0—improvements in chemistry prediction and gene cluster boundary identification, Nucleic Acids Research, 45:W36-W41 (2017).

Chiang, YM et al, A gene cluster containing two fungal polyketide synthases encodes the biosynthetic pathway for a polyketide, asperfuranone, in Aspergillus nidulans, Journal of the American Chemical Society, 13(18): 2965-2970 (2009).

Chung, KR et al., Determination of a transcriptional regulator-like gene involved in biosynthesis of elsinochrome phytotoxin by the citrus scab fungus, *Elsinoe fawcettii*. Microbiology, 154(11):3556-3566 (2008).

Cimermancic, P. et al., Insights into Secondary Metabolism from a Global Analysis of Prokaryotic Biosynthetic Gene Clusters, Cell, 158(2):412-421 (2014).

Clevenger, K. D. et al., A scalable platform to identify fungal secondary metabolites and their gene clusters, Nat. Chem. Bio., 13(8):895-901 (2017).

Dixon, S. J. and Strockwell, R. R., Identifying druggable disease-modifying gene products, Curr. Opin. Chem. Biol. 13(5-6):549-555 (2009).

Ehrlich, KC et al., Aflatoxin biosynthesis gene clusters and flanking regions, Journal of Applied Microbiology, 99(3):518-527 (2005).

Harvey, C. J., Precursor-Directed Biosynthesis Of Macrolide Antibiotics, Dissertation as submitted to the Department of Chemistry and the Committee on Graduate Studies of Stanford University in Partial Fulfillment of the Requirements for the Degree of Doctor of Philosophy, 176 pages (Apr. 2012).

International Search Report for PCT/US2018/051134 (Human Therapeutic Targets and Modulators Thereof, filed Sep. 14, 2018), issued by ISA/US, 6 pages (dated Feb. 21, 2019).

Keller, N. P., Fungal secondary metabolism: regulation, function and drug discovery, Nat. Chem. Biol., 17(3):671-180 (2019).

Kennedy, J. et al., Modulation of polyketide synthase activity by accessory proteins during lovastatin biosynthesis, Science, 284(5418):1368-1372 (1999).

Lowther, W. T. et al., The anti-angiogenic agent fumagillin covalently modifies a conserved active-site histidine in the *Escherichia coli* methionine aminopeptidase, Proc. Natl. Acad. Sci., USA, 95:12153-7 (1998).

Montiel, D. et al., Yeast homologous recombination-based promoter engineering for the activation of silent natural product biosynthetic gene clusters, PNAS, 112(29):8953-8958 (2015).

Regueira, T. B. et al., Molecular basis for mycophenolic acid biosynthesis in Penicillium brevicompactum, Appl. Environ. Microbiol., 77(9):3035-3043 (2011).

Stockwell, B., Outsmarting Cancer. A biologist talks about what makes disease-causing proteins so difficult to target with drugs, Sci. Am., 305:20 (2011).

Tang, X. et al., Identification of Thiotetronic Acid Antibiotic Biosynthetic Pathways by Target-directed Genome Mining, ACS Chem. Biol., 10(12):2841-2849 (2015).

Thaker, M. N. et al., Antibiotic resistance-mediated isolation of scaffold-specific natural product producers, Nature Protocols, 9(6):1459-1479 (2014).

Vesth, TC et al., FunGeneClusterS: Predicting fungal gene clusters from genome and transcriptome data, Synthetic and Systems Biotechnology, 1(2): 122-129 (2016).

Written Opinion for PCT/US2018/051134 (Human Therapeutic Targets and Modulators Thereof, filed Sep. 14, 2018), issued by ISA/US, 11 pages (dated Feb. 21, 2019).

Yan, Y. et al., Resistance-gene-directed discovery of a natural-product herbicide with a new mode of action, Nature, 559(7714): 415-418 (2018).

Yeh, H.H. et al., Resistance Gene-Guided Genome Mining: Serial Promoter Exchanges in Aspergillus nidulans Reveal the Biosynthetic Pathway for Fellutamide B, a Proteasome Inhibitor, ACS Chem. Biol., 11:2275-2284 (2016).

Basson, M. E. et al. (Sep. 1988). "Structural And Functional Conservation Between Yeast And Human 3-Hydroxy-3-Methylglutaryl Coenzyme A Reductases, The Rate-Limiting Enzyme Of Sterol Biosynthesis," Molecular And Cellular Biology 8(9):3797-3808.

Berge, S.M. et al. (Jan. 1977). "Pharmaceuticals Salts," J. Pharmaceutical Sciences 66(1):1-19.

Hannigan, G.D. et al. (Oct. 10, 2019). "A Deep Learning Genome-Mining Strategy For Biosynthetic Gene Cluster Prediction," Nucleic Acids Research 47(18), 20 pages, retrieved on Feb. 2, 2022 from https://academic.oup.com/nar/article/4 7/18/e110/5545735.

Huang, L.-C. et al. (Mar. 5, 2021). "Kinortho: A Method For Mapping Human Kinase Orthologs Across The Tree Of Life And Illuminating Understudied Kinases," bioRxiv 5(49):31 pages, retrieved on Jan. 25, 2023 from https://doi.org/10.1101/2021.03.05.434161.

Kapasa, M. et al. (2010). "Phylogenetic And Regulatory Region Analysis Of Wnts Genes Reveals Conservation Of A Regulatory Module With Put.Alive Implication In Pancreas Development," Biology Direct 5:49, 13 pages, retrieved on Jan. 25, 2023, retrieved from http://www.biology-direct.com/contenli5/1/49.

Kautsar, S.A. et al. (Jan. 13, 2021). "BiG-SLiCE: A Highly Scalable Tool Maps The Diversity Of 1.2 Million Biosynthetic Gene Clusters," GigaScience 10(1): 31 pages, retrieved on Feb. 2, 2022 from https://academic.oup.com/gigascience/article/10/1/giaa154/6092777.

Naughton, L.M. et al. (Aug. 18, 2017). "Identification of Secondary Metabolite Gene Clusters in the *Pseudovibrio* Genus Reveals Encouraging Biosynthetic Potential towards the Production of Novel Bioactive Compounds," Frontiers in Microbiology 8(1494):1-15, retrieved from https://www.frontlersin.org/articles/10.3389/fmlcb.2017.01494/full.

Orvis, J. (Jun. 2010). "Ergatis: A Web Interface And Scalable Software System Ror Bioinformatics Workflow," BioInformatics 26(12):1488-1492, 16 pages, retrieved on Jan. 25, 2023, from https://academic.oup.com/bioinformatics/article/26/12/1488/28'1443?view=extract.

Powers, S. et al. (Mar. 1, 1984). "Genes In S. Cerevisiae Encoding Proteins With Domains Homologous To The Mammalian Ras Proteins", Cell, Elsevier, Amsterdam, NL 36(3):607-612.

Subazini, T.K. et al. (Jun. 23, 2011). "Characterization Of Lovastatin Biosynthetic Cluster Proteins In Aspergillus Terreus Strain ATCC 20542", Bioinformation 6(7):250-254.

Tommasi, S. et al. (Apr. 2002). "RASSF3 And NORE1: Identification And Cloning Of Two Human Homologues Of The Putative Tumor Suppressor Gene RASSF1," Oncogene 21(17):2713-2720.

Vandova, G.A. et al. (Jun. 2, 2020). "Identification Of Polyketide Biosynthetic Gene Clusters That Harbor Self-Resistant Genes," 37 pages, retrieved from https://web.archlve.org/web/20200711060946id/https://www.biorxiv.org/content/biorxiv/early/2020/06/02/2020.06.01.128595.full.pdf.

Vesth, T.C. et al. (Jun. 1, 2016). "Fungeneclusters: Predicting Fungal Gene Clusters From Genome And Transcriptome Data", Synthetic and Systems Biotechnology 1(2):122-129.

\* cited by examiner

```
                            10                  20              30              40
KRAS            M-----------------TEYKLVVVGAGG------VGKSALTIQLIQNHFVDEYDPTIEDSYRKQVVIDG
HRAS            M-----------------TEYKLVVVGAGG------VGKSALTIQLIQNHFVDEYDPTIEDSYRKQVVIDG
NRAS            M-----------------TEYKLVVVGAGG------VGKSALTIQLIQNHFVDEYDPTIEDSYRKQVVIDG
ANHP_459_5      MQP---------------PREYHIVVLGA-------AQFVQNVWIESYDPTIEDSYRKQIEVDG
KB73344_288_17  MSQ---------------REVHIVVLGSGG------VGKSCLTAQFVQNVWIESYDPTIEDSYRKVLEVDG
CM004463        MAS---------------KFLREVKLVVVGGGG---VGKSCLTIQSHFVDEYDPTIEDSYRKQCVIDE
KV42800_485_5   MSRS------AAQA----SFLREVKLVVVGGGGMSLVSPVGKSALTIQFIQSHFVDEYDPTIEDSYRKQCVIDD
AACS_391_8      MPEVMNAMYATKGGIFDVSENDKAQFLREYKLVVVGGGG---VGKSALTIQFIQSHFVDEYDPTIEDSYRKQCIIDD
JH97138_360_5   MANN------AASRAA---QAQFLREYKLVVVGGGG---VGKSALTIQFIQSHFVDEYDPTIEDSYRKQCVIDE
KI911109_c052   M-----------------TLYKLVVLGDGG------VGKTALTIQLCLNHFVETYDPTIEDSYRKQVVIDQ
KE54696_c00122  MDAD--------------PYLL--------KFLREYKLVVVGGGG---VGKSCLTIQLIQSHFVDEYDPTIEDSYRKQCVIDE

KRAS            ETCLLDILDTAGQEEYSAMRDQYMRTGEGFLCVFAINNTKSFEDIHHYREQIKRVKDSE-----------
HRAS            ETCLLDILDTAGQEEYSAMRDQYMRTGEGFLCVFAINNTKSFEDIHQYREQIKRVKDSD-----------
                                      50              60                  70              80              90             100
NRAS            ETCLLDILDTAGQEEYSAMRDQYMRTGEGFLCVFAINNSKSFADINLYREQIKRVKDSD-----------
ANHP_459_5      RQCILEILDTAGTEQF---------IFSITSMSSLNELSEIREQILRIKDDD-----------
KB73344_288_17  RHVILEILDTAGTEQF----LYMKTQGFLLVFSITSESSFWELAELREQIRRIKEDS-----------
CM004463        EVALLDVLDTAGQEEYSAMREQYMRTGEGFLLVYSITSRQSFERITTFQQQILRVKDKD-----------
KV42800_485_5   EVALLDVLDTAGQEEYGAMREQYMRTGEGFLLVYSITSRNSFERISTFHQQILRVKDKD-----------
AACS_391_8      EVALLDVLDTAGQEEYGAMREQYMRTGEGFLLVYSITSRNSFEEISIFHQQILRVKDQD-----------
JH97138_360_5   EVALLDVLDTAGQEEYTALRDQWIRDGEGFVLVYSITARSSFEEINQFYQQILRVKDQD-----------
KI911109_c052   Q-SMLEVLDTAGQEEYTALRDQWIRDGEGFVLVYSITSRASFARIPKFYNQIKMVKESASSGSPAGASYLTSPINSPSGP
KE54696_c00122  EVALLDVLDTAGQEEYSAMREQYMRTGEGFLLVYSITSRQSFEEMLTFQQQILRVKDRD-----------

Boldface: Nucleotide binding residues of KRAS
                            FIG. 13
```

```
KRAS        M----------------TEYKLVVVGAGG-------VGKSALTIQLIQNHFVDEYDPTIEDSYRKQVVIDG
HRAS        M----------------TEYKLVVVGAGG-------VGKSALTIQLIQNHFVDEYDPTIEDSYRKQVVIDG
NRAS        M----------------TEYKLVVVGAGG-------VGKSALTIQLIQNHFVDEYDPTIEDSYRKQVVIDG
ANHP_459_5      MQP------------RREYHIVVLGA--------AQFVQNVWIESYDPTIEDSYRKQIEVDG
KB73344_288_17  MSQ------------REYHIVVLGSGG-------VGKSCLTAQFVQNVWIESYDPTIEDSYRKVLEVDG
CM004463        MAS-----------KFLREYKLVVVGGGG------VGKSCLTIQLIQSHFVDEYDPTIEDSYRKQCVIDE
KV42800_485_5   MSRS------AAQA--------SFLREYKLVVVGGGGMSLVSRVGKSALTIQFIQSHFVDEYDPTIEDSYRKQCVIDD
AACS_391_8      MPEVMNAMYATKGGIFDVSENDKAQFLREYKLVVVGGGG------VGKSALTIQFIQSHFVDEYDPTIEDSYRKQCIIDD
JH97138_360_5   MANN---------AASRAA----QAQFLREYKLVVVGGGG------VGKSALTIQFIQSHFVDEYDPTIEDSYRKQCVIDE
KI911109_c052   M--------------TLYKLVVLGDGG------VGKTALTIQLCLNHFVETYDPTIEDSYRKQVVIDQ
KE54696_c00122  MDAD----------PYLL-------KFLREYKLVVVGGGG------VGKSCLTIQLIQSHFVDEYDPTIEDSYRKQCVIDE

KRAS        ETCLLDILDILDTAGQEEYSAMRDQYMRTGEGFLCVFAINNTKSFEDIHHYREQIKRVKDSE------
HRAS        ETCLLDILDILDTAGQEEYSAMRDQYMRTGEGFLCVFAINNTKSFEDIHQYREQIKRVKDSD------
NRAS        ETCLLDILDILDTAGQEEYSAMRDQYMRTGEGFLCVFAINNSKSFADINLYREQIKRVKDSD------
ANHP_459_5      RQCILEILDTAGTEQF-------IFSITSMSSLNELSEIREQILRIKDDD------
KB73344_288_17  RHVILEILDTAGTEQFK-----LYMKTGQGFLLVFSITSESSFWELAELREQIRRIKEDS------
CM004463        EVALLDVLDTAGQEEYSAMREQYMRTGEGFLLVYSITSRQSFEEITTFQQQILRVKDKD------
KV42800_485_5   EVALLDVLDTAGQEEYGAMREQYMRTGEGFLLVYSITSRNSFEEISTFHQQILRVKDKD------
AACS_391_8      EVALLDVLDTAGQEEYGAMREQYMRTGEGFLLVYSITSRNSFEEISIFHQQILRVKDQD------
JH97138_360_5   EVALLDVLDTAGQEEYGAMREQYMRTGEGFLLVYSITARSSFEEINQFYQQILRVKDQD------
KI911109_c052   Q-SMLEVLDTAGQEEYTALRDQWIRDGEGFVLVYSITSRASFARIPKFYNQIKMVKESASSGSPAGASYLTSPINSPSGP
KE54696_c00122  EVALLDVLDTAGQEEYSAMREQYMRTGEGFLLVYSITSRQSFEEMLTFQQQILRVKDRD------
```

Boldface: KRAS residues w/ 4 Å of BRAF, PDB: 4G0N

FIG. 14

```
                                      10                    20                    30              40
KRAS             M-------------TEYKLVVVGAGG--------VGKSALTIQLIQNHFVDEYDPTIEDSYRKQVVIDG
HRAS             M-------------TEYKLVVVGAGG--------VGKSALTIQLIQNHFVDEYDPTIEDSYRKQVVIDG
NRAS             M-------------TEYKLVVVGAGG--------VGKSALTIQLIQNHFVDEYDPTIEDSYRKQVVIDG
ANHP_459_5       MQP-----------RREYHIVVLGA---------AQFVQNVWIESYDPTIEDSYRKQIEVDG
KB73344_288_17   MSQ-----------REYHIVVLGSGG--------VGKSCLTAQFVQNVWIESYDPTIEDSYRKVLEVDG
CM004463         MAS-----------KFLREYKLVVVGGGG-----VGKSCLTIQLIQSHFVDEYDPTIEDSYRKQCVIDE
KV42800_485_5    MSRS----AAQA--SFLREYKLVVVGGGMSLVSRVGKSALTIQFIQSHFVDEYDPTIEDSYRKQCVIDD
AACS_391_8       MPEVMNAMYATKGGIFDVSENDKAQFLREYKLVVVGGGG--VGKSALTIQFIQSHFVDEYDPTIEDSYRKQCIIDD
JH97138_360_5    MANN----------AASRAA----QAQFLREYKLVVVGGGG--VGKSALTIQFIQSHFVDEYDPTIEDSYRKQCVIDE
KI911109_c052    M-------------TLYKLVVLGDGG--------VGKTALTIQLCLNHFVETYDPTIEDSYRKQVVIDQ
KE54696_c00122   MDAD----------PYLL----------KFLREYKLVVVGGGG--VGKSCLTIQLIQSHFVDEYDPTIEDSYRKQCVIDE

KRAS             ETCLLDILDTAGQEEYSAMRDQYMRTGEGFLCVFAINNTKSFEDIHHYREQIKRVKDSE-------
HRAS             ETCLLDILDTAGQEEYSAMRDQYMRTGEGFLCVFAINNTKSFEDIHQYREQIKRVKDSD-------
NRAS             ETCLLDILDTAGQEEYSAMRDQYMRTGEGFLCVFAINNSKSFADINLYREQIKRVKDSD-------
ANHP_459_5       RQCILEILDTAGTEQF-------IFSITSMSSLNELSEIREQILRIKDDD----
KB73344_288_17   RHVILEILDTAGTEQFK------LVMKTGQGFLLVFSITSESSFWELAELREQIRRIKEDS-----
CM004463         EVALLDVLDTAGQEEYSAMREQYMRTGEGFLLVYSITSRQSFEEITTFQQQILRVKDKD-------
KV42800_485_5    EVALLDVLDTAGQEEYGAMREQYMRTGEGFLLVYSITSRNSFEEISTFHQQILRVKDKD-------
AACS_391_8       EVALLDVLDTAGQEEYGAMREQYMRTGEGFLLVYSITSRNSFEEISFHQQILRVKDQD-------
JH97138_360_5    EVALLDVLDTAGQEEYTALRDQWIRDGEGFVLVYSITARSSFEEINQFYQQILRVKDQD-------
KI911109_c052    Q-SMLEVLDTAGQEEYTALRDQWIRDGEGFVLVYSITSRASFARIPKFYNQIKMVKESASSGSPAGASYLTSPINSPSGP
KE54696_c00122   EVALLDVLDTAGQEEYSAMREQYMRTGEGFLLVYSITSRQSFEEMLTFQQQILRVKDRD-------
```

Boldface: KRAS residues w/ 4 Å of rasGAP, PDB: 1WQ1

FIG. 15

```
KRAS              M------------------------TEYKLVVVGAGG------VGKSALTIQLIQNHFVDEYDPTIEDSYRKQVVIDG
HRAS              M------------------------TEYKLVVVGAGG------VGKSALTIQLIQNHFVDEYDPTIEDSYRKQVVIDG
NRAS              M------------------------TEYKLVVVGAGG------VGKSALTIQLIQNHFVDEYDPTIEDSYRKQVVIDG
ANHP_459_5        MQP----------------------RREYHIVVLGA-------AQFVQNVWIESYDPTIEDSYRKQIEVDG
KB73344_288_17    MSQ----------------------REYHIVVLGSGG------VGKSCLTAQFVQNVWIESYDPTIEDSYRKVLEVDG
CM004463          MAS----------------------KFLREYKLVVVGGGG---VGKSCLTIQLIQSHFVDEYDPTIEDSYRKQCVIDE
KV42800_485_5     MSRS----AAQA-------------SFLREYKLVVVGGGGMSLVSRVGKSALTIQFIQSHFVDEYDPTIEDSYRKQCVIDD
AACS_391_8        MPEVMNAMYATKGGIFDVSENDKAQFLREYKLVVVGGGG-----VGKSALTIQFIQSHFVDEYDPTIEDSYRKQCIIDD
JH97138_360_5     MANN---------AASRAA----QAQFLREYKLVVVGGGG---VGKSALTIQFIQSHFVDEYDPTIEDSYRKQCVIDE
KI911109_c052     M----------------------TLYKLVVLGDGG--------VGKTALTIQLCLNHFVETYDPTIEDSYRKQVVIDQ
KE54696_c00122    MDAD--------PYLL-------KFLREYKLVVVGGG------VGKSCLTIQLIQSHFVDEYDPTIEDSYRKQCVIDE

KRAS              ETCLLDILDTAGQEEYSAMRDQYMRTGEGFLCVFAINNTKSFEDIHHYREQIKRVKDSE---------------------------
HRAS              ETCLLDILDTAGQEEYSAMRDQYMRTGEGFLCVFAINNTKSFEDIHQYREQIKRVKDSD---------------------------
NRAS              ETCLLDILDTAGQEEYSAMRDQYMRTGEGFLCVFAINNSKSFADINLYREQIKRVKDSD---------------------------
ANHP_459_5        RQCILEILDTAGTEQF--------IFSITSMSSLNELSEIREQILRIKDDD-----------------------------------
KB73344_288_17    RHVILEILDTAGTEQFK-----LIYMKTGQGFLLVFSITSESSFWELAELREQIRRIKEDS-------------------------
CM004463          EVALLDVLDTAGQEEYSAMREQYMRTGEGFLLVYSITSRQSFEEITTFQQQILRVKDKD--------------------------
KV42800_485_5     EVALLDVLDTAGQEEYGAMREQYMRTGEGFLLVYSITSRNSFEEISTFHQQILRVKDKD--------------------------
AACS_391_8        EVALLDVLDTAGQEEYGAMREQYMRTGEGFLLVYSITSRNSFEEISIFHQQILRVKDQD--------------------------
JH97138_360_5     EVALLDVLDTAGQEEYGAMREQYMRTGEGFLLVYSITARSSFEEINQFYQQILRVKDQD--------------------------
KI911109_c052     Q-SMLEVLDTAGQEEYTALRDQWIRDGEGFVLVYSITSRASFARIPKFYNQIKMVKESASSGSPAGASYLTSPINSPSGP
KE54696_c00122    EVALLDVLDTAGQEEYSAMREQYMRTGEGFLLVYSITSRQSFEEMLTFQQQILRVKDRD--------------------------
```

Boldface: KRAS residues w/ 4 Å of SOS, PDB:1BKD

FIG. 16

```
Human_ARNOSec7_Ter   LEANEGSK--------TLQRNRKMA----------MGRKKFNMDPKKGIQFLVENELLQNTP---EE---IARFLYKGEGLNKT
Human_GBF1Sec7       ----------------DPRELIEIKNKKKLLITGTEQFNQKPKKGIQFLQEKGLL-TIP---MDNTEVAQWLRENPRLDKK
ETaGSec7_NCBI        --------DPNALRQQRSRKSMIM---------KGASKFNENPKAGIAFLVAQGVIQEPENPKN---IAEFIKGTTRIDKK Human_ARNOSec7_Ter   AIGDYLGEREELNLAVLHAFVDLHEFTDLNIVQALRQFLWSFRLPGEAQKIDRMMEAFAQRYCLCNPGVFQS---TDTC--
Human_GBF1Sec7       MIGEFVSDR--KNIDLLESFVSTFSFQGLRLDEALRLYLEAFRLPGEAPVIQRLLEAFTERWMNCNGSPFAN--SDAC--
ETaGSec7_NCBI        ILGEFISKK--TNENILNEFMKLFNFAGKRIDEAIRELLGAFRLPGESALIERIVEVFAAQYM---DDAKPAGIADSTAA Human_ARNOSec7_Ter   YVLSYSVIMLNTDLHNPNVR---DK----MGLERFVAMNRGINEGG-DLPEELLRNLYDSIPNEPFKIPEDDGND
Human_GBF1Sec7       FSLAYAVIMLNTDQHNHNVR---KQNAPMTLEEFRNLKGVNGGK-DFEQDILEDMYHAIKNEEIVMPEEQT---
ETaGSec7_NCBI        FVLVYATILLNTDQHNPNFRGQKR---MTIENFAQNLRGV-NDQGDFDSNFLQEIFDSIRTHEIILPEEHD---
```

PANEL A

FIG. 19

Boldface: ARNOSec7 residues w/4 Å of Brefeldin A, PDB: 1R8Q

```
                           50
Human_ARNOSec7_Ter   LEANEGSK--------TLQRNRKMA----------MGRKKFNMDPKKGIQFLVNELLQNTP----EE----IARFLYKGEGLNKT
Human_GBF1Sec7       ----------------------DPRELIEIKNKKLLITGTEQFNQKPKKGIQFLQEKGLL-TIP---MDNTEVAQWLRENPRLDKK
ETaGSec7_NCBI        -----------DPNALRQQRSRKSMIM---------KGASKFNENPKAGIAFLVAQGVIQEPENPKN---IAEFIKGTTRIDKK Human_ARNOSec7_Ter   AIGDYLGEREELNLAVLHAPVDLREFTDLNLVQALRQFIWSFRLPGEAQKIDRMMEAFAQRYCLCNPGVFQS---TDTC--
Human_GBF1Sec7       MIGEFVSDR---KNIDLLESFVSTFSFQGLRLDEAIRLYLEAFRLPGEAPVTQRLLEAFTERWMCNGSPFAN--SDAC--
ETaGSec7_NCBI        ILGEFISKK--TNENILNEFMKLFNFAGKRIDEAIRELLGAFRLPGESALIERIVEVFAAQYM---DDAKPAGIADSTAA Human_ARNOSec7_Ter   YVLSYSVIMLNTDLHNPNVR---DK-----MGLERFVAMNRGINEGG-DLPEELLRNLYDSIRNEPFKIPEDDGND
Human_GBF1Sec7       FSLAVAVIMLNTDQHNHNVR--KQNAPMTLEEFRKNLKGVNGGK-DFEQDILEDMYHAIKNEEIVMPEEQT---
ETaGSec7_NCBI        FVLVATILLNTDQHNPNFRGQKR---MTIENFAQNLRGV-NDQGDFDSNFLQEIFDSIRTHEIILPEEHD---
```

Boldface: Matched and conserved residues

PANEL B

FIG. 19 (CONTINUED)

RasGAP ETaG Cluster (NRPS)

*Corynespora cassiicola* UM 591

*Magnaporthe oryzae* strain SV9610

Biosynthetic gene    GAP    Other/hypothetical gene

FIG. 36

HUMAN THERAPEUTIC TARGETS AND MODULATORS THEREOF

CROSS-REFERENCE TO RELATED APPLICATIONS

This application claims priority to U.S. Provisional Application No. 62/558,744, filed Sep. 14, 2017, the entirety of which is incorporated herein by reference.

BACKGROUND

Identification of so-called "druggable" targets within the human proteome has been described as "a significant challenge". See, for example, Dixon et al *Curr. Opin. Chem. Biol.* 13:549, 2009. As of 2011, reports estimated that only about 2% of human proteins had been successfully targeted by approved drugs, and furthermore that only 10-15% of human proteins are even susceptible to targeting (i.e., are "druggable"). See, for example, Stockwell *Sci. Am* 305:20, 2011.

SUMMARY

Evidence is emerging that some microbial biosynthetic gene clusters sometimes contain genes (referred to herein as "passenger" genes) that appear not to be involved in synthesis of the relevant biosynthetic products produced by the enzymes encoded by the clusters. In some cases, such passenger genes have been described as "self-protective" because they encode proteins that apparently can render the host organism resistant to the relevant biosynthetic product. For example, in some cases, genes encoding transporters of the biosynthetic products, detoxification enzymes that act on the biosynthetic products, or resistant variants of proteins whose activities are targeted by the biosynthetic products, have been reported. See, for example, Cimermancic et al *Cell* 158:412, 2014; Keller *Nat. Chem. Biol.* 11:671, 2015. Researchers have proposed that identification of such genes, and their functions, could be useful in determining the role of the biosynthetic products synthesized by the enzymes of the clusters. See, for example, Yeh et al. *ACS Chem. Biol.* 11:2275, 2016; Tang et al. *ACS Chem. Biol.* 10:2841, 2015; Regueira et al. *Appl, Environ. Microbiol.* 77:3035, 2011; Kennedy et al., *Science* 284:1368, 1999; Lowther et al., *Proc. Natl. Acad. Sci. USA* 95:12153, 1998; Abe et al, *Mol. Genet. Genomics* 268:130, 2002.

Among other things, the present disclosure offers a different perspective on non-biosynthetic genes present in biosynthetic gene clusters, or in proximity zones relative to biosynthetic genes of the clusters as described herein, and provides new insights regarding potential usefulness of certain such genes in human therapeutics. In some embodiments, the present disclosure provides technologies that utilize such insights to develop and/or improve human therapeutics.

Among other things, the present disclosure provides an insight that certain non-biosynthetic genes present in biosynthetic gene clusters, or in proximity zones relative to biosynthetic genes of the clusters, and particularly in eukaryotic (e.g., fungal, as contrasted with bacterial) biosynthetic gene clusters, may represent homologs of human genes that represent targets of therapeutic interest. The present disclosure defines parameters that characterize such non-biosynthetic genes of interest, herein referred to as "embedded target genes" or "ETaGs". The present disclosure provides technologies for identifying and/or characterizing ETaGs, databases including biosynthetic gene cluster and/or ETaG gene sequences (and optionally relevant annotations), systems for identifying and/or characterizing human target genes corresponding to ETaGs, as well as methods of making and/or using such human target genes and/or systems that contain and/or express them, etc.

The present disclosure contributes a further insight that relationship between ETaGs and their related biosynthetic gene clusters (biosynthetic gene clusters that contain biosynthetic genes in proximity zones relative to which the ETaGs are within) informs the identification, design, and/or characterization of effective modulators of the corresponding human target genes. The present disclosure provides technologies for such identification, design, and/or characterization, and also provides agents that achieve modulation of relevant human target genes, as well as methods of providing and/or using such agents.

As noted above, the present disclosure encompasses the insight that an ETaG can serve as a functional homolog (e.g., an ortholog) of a human target of medical (e.g., therapeutic) relevance. According to the present disclosure, sequences of passenger (i.e., non-biosynthetic) genes within eukaryotic (e.g., fungal) biosynthetic gene clusters, or in proximity zones relative to biosynthetic genes of the clusters, can be compared with those of human genes. Nucleic acid sequence similarity, peptide sequence similarity and/or phylogenetic relationships can be determined (e.g., quantitatively assessed and/or through evolutionary tree visualization) for the compared sequences. Alternatively or additionally, conservation of known structural and/or protein effector elements can be assessed. In some embodiments, those passenger genes with relatively high homology to human sequences and/or conserved structural and/or protein effector elements may be prioritized as ETaGs of interest as human drug targets.

In some embodiments, the present disclosure provides methods comprising steps of:

querying a set of nucleic acid sequences, each of which is found in a fungal strain and comprises a biosynthetic gene cluster; and identifying within at least one of the fungal nucleic acid sequences an embedded target gene (ETaG) sequence characterized in that it:
  is within a proximity zone relative to at least one gene in the cluster; and
  is optionally co-regulated with at least one biosynthetic gene in the cluster.

Typically, a biosynthetic gene cluster comprises one or more biosynthetic genes. In some embodiments, a biosynthetic gene cluster comprises one or more biosynthetic genes and one or more non-biosynthetic genes. In some embodiments, a non-biosynthetic gene is regulatory, e.g., transcription factors. In some embodiments, in a biosynthetic gene cluster identified by bioinformatics, a non-biosynthetic gene may be a hypothetical gene. In some embodiments, borders of biosynthetic gene clusters are defined by bioinformatics methods, for example, antiSMASH. In some embodiments, biosynthetic genes and non-biosynthetic genes are designated based on bioinformatics. In some embodiments, non-biosynthetic gene might have biosynthetic functions even though they are identified as non-biosynthetic gene by bioinformatics methods (and/or indicated as non-biosynthetic gene in the present disclosure).

In some embodiments, the present disclosure provides methods comprising steps of:

querying a set of nucleic acid sequences, each of which is found in a fungal strain and comprises a biosynthetic gene cluster; and identifying within at least one of the fungal nucleic acid sequences an embedded target gene (ETaG) sequence characterized in that it:

is within a proximity zone relative to at least one biosynthetic gene in the cluster; and is optionally co-regulated with at least one biosynthetic gene in the cluster.

In some embodiments, the present disclosure encompasses the recognition that ETaGs from eukaryotic fungi can bear more similarities to mammalian genes than, for example, their counterparts, if any, in prokaryotes such as certain bacteria. In some embodiments, fungi contain ETaGs that are more therapeutically relevant, and/or contain more therapeutically relevant ETaGs, than organisms that are evolutionarily more distant from human.

In some embodiments, the present disclosure provides methods comprising steps of:

querying a set of nucleic acid sequences, each of which is found in a fungal strain and comprises a biosynthetic gene cluster; and identifying within at least one of the fungal nucleic acid sequences an embedded target gene (ETaG) sequence characterized in that it:

is within a proximity zone relative to at least one gene in the cluster;

is homologous to an expressed mammalian nucleic acid sequence; and is optionally co-regulated with at least one biosynthetic gene in the cluster.

In some embodiments, the present disclosure provides methods comprising steps of:

querying a set of nucleic acid sequences, each of which is found in a fungal strain and comprises a biosynthetic gene cluster; and identifying within at least one of the fungal nucleic acid sequences an embedded target gene (ETaG) sequence characterized in that it:

is within a proximity zone relative to at least one biosynthetic gene in the cluster;

is homologous to an expressed mammalian nucleic acid sequence; and is optionally co-regulated with at least one biosynthetic gene in the cluster.

In some embodiments, a proximity zone is no more than 1-100, for example, no more than 1, 2, 3, 4, 5, 6, 7, 8, 9, 10, 15, 20, 30, 40, 50, 60, 70, 80, 90, or 100 kb upstream or downstream of a biosynthetic gene in a cluster. In some embodiments, a proximity zone is no more than 1-100, for example, no more than 1, 2, 3, 4, 5, 6, 7, 8, 9, or 10 kb upstream or downstream of a biosynthetic gene in a cluster. In some embodiments, an ETaG is within a biosynthetic gene cluster. In some embodiments, a proximity zone is between two biosynthetic genes of a biosynthetic gene cluster.

In some embodiments, an ETaG sequence is homologous to a mammalian nucleic acid sequence. In some embodiments, a mammalian sequence is a human nucleic acid sequence. In some embodiments, an ETaG sequence is homologous to a human nucleic acid sequence. In some embodiments, an ETaG sequence is homologous to an expressed mammalian nucleic acid sequence. In some embodiments, an ETaG sequence is homologous to an expressed human nucleic acid sequence. In some embodiments, a mammalian nucleic acid, e.g., a human nucleic acid sequence, is related to a human disease, disorder, or condition. In some embodiments, such a human nucleic acid sequence is an existing target of therapeutic interest. In some embodiments, such a human nucleic acid sequence is a novel target of therapeutic interest. In some embodiments, such a human nucleic acid sequence is a target previously considered not susceptible to targeting by, e.g., small molecules. In some embodiments, a biosynthetic product produced by enzymes encoded by the related biosynthetic gene cluster, or an analog thereof, is a modulator (e.g., an activator, an inhibitor, etc.) of a human target.

In some embodiments, an ETaG sequence is homologous to an expressed mammalian nucleic acid sequence in that its sequence, or a portion thereof, is at least 50%, 60%, 70%, 80%, or 90% identical to that of an expressed mammalian nucleic acid sequence. In some embodiments, an ETaG sequence is homologous to a mammalian nucleic acid sequence in that mRNA produced from an ETaG, or a portion thereof, is homologous to that of a mammalian nucleic acid sequence. In some embodiments, a homologous portion is at least 50, 100, 150, or 200 base pairs in length. In some embodiments, a homologous portion encodes a conserved protein, or a conserved portion of protein, such as a protein domain, a set of residues that relates to a function (e.g., interaction to another molecule (e.g., a protein, a small molecule, etc.), enzymatic activity, etc.), etc., from fungi to a mammal.

In some embodiments, an ETaG sequence is homologous to a mammalian nucleic acid sequence in that a product encoded by an ETaG, or a portion thereof, is homologous to that encoded by a mammalian nucleic acid sequence. In some embodiments, an ETaG sequence is homologous to a mammalian nucleic acid sequence in that a protein encoded by an ETaG, or a portion thereof, is homologous to that encoded by a mammalian nucleic acid sequence. In some embodiments, an ETaG sequence is homologous to a mammalian nucleic acid sequence in that a portion of a protein encoded by an ETaG is homologous to that encoded by a mammalian nucleic acid sequence.

In some embodiments, a portion of a protein is a protein domain. In some embodiments, a protein domain is an enzymatic domain. In some embodiments, a protein domain interacts with one or more agents, e.g., small molecules, lipids, carbohydrates, nucleic acids, proteins, etc.

In some embodiments, a portion of a protein is a functional and/or structural domain that defines a protein family that the protein belongs to. Amino acid resides that within specific catalytic or structural domain defining patent families can be selected based on predictive subfamily domain architecture, and optionally verified by various assays, for use in alignment analysis of homology.

In some embodiments, a portion of a protein is a set of key residues, either consecutive or not consecutive, that are important for a function of a protein. In some embodiments, a function is an enzymatic activity, and a portion of a protein is a set of residues that are required for the activity. In some embodiments, a function is an enzymatic activity, and a portion of a protein is a set of residues that interact with a substrate, an intermediate, or a product. In some embodiments, a set of residues interact with a substrate. In some embodiments, a set of residues interact with an intermediate. In some embodiments, a set of residues interact with a product.

In some embodiments, a function is an interaction with one or more agents, e.g., small molecules, lipids, carbohydrates, nucleic acids, proteins, etc., and a portion of a protein is a set of residues that are required for the interaction. In some embodiments, a set of residues each independently contact an interacting agent. For example, in some embodiments, each of the residues of a set independently contacts an interacting small molecule. In some embodiments, a protein is a kinase and an interacting small molecule is or comprises a nucleobase, and a set of residues each independently contact the nucleobase via, e.g., hydrogen bonding, electrostatic forces, van der Waals forces, aromatic stacking, etc. In some embodiments, an interacting agent is another macromolecule. In some embodiments, an interaction agent is a nucleic acid. In some embodiments, a set of residues are those that contact an interacting nucleic acid, for example, those in transcription factors. In some embodiments, a set of residues are those that contact an interacting protein.

In some embodiments, a portion of a protein is or comprises an essential structural element of protein effector recruitment and/or binding, for example, based on tertiary protein structures of human targets.

Portions of proteins, such as protein domains, sets of residues responsible for biological functions, etc., can be conserved from species to species, for example, in some embodiments from fungi to human as illustrated in the present disclosure.

In some embodiments, protein homology is measured based on exact identity, e.g., the same amino acid residues at given positions. In some embodiments, homology is measured based on one or more properties, e.g., amino acid residues bearing one or more identical or similar properties (e.g., polar, non-polar, hydrophobic, hydrophilic, size, acidic, basic, aromatic, etc.). Exemplary methods for assessing homology are widely known in the art and can be utilized in accordance with the present disclosure, for example, MUSCLE, TCoffee, ClustalW, etc.

In some embodiments, a protein encoded by an ETaG, or a portion thereof (e.g., those described in the present disclosure), is at least 50%, 60%, 70%, 80%, 85%, 90%, 91%, 92%, 93%, 94%, 95%, 96%, 97%, 98%, or 99%, or 100% (when 100% it is identical) homologous to that encoded by a mammalian nucleic acid sequence. In some embodiments, a protein encoded by an ETaG, or a portion thereof, is at least 50%, 60%, 70%, 80%, 85%, 90%, 91%, 92%, 93%, 94%, 95%, 96%, 97%, 98%, or 99%, or 100% homologous to that encoded by an expressed mammalian nucleic acid sequence.

In some embodiments, an ETaG is co-regulated with at least one biosynthetic gene in the biosynthetic gene cluster. In some embodiments, an ETaG is co-regulated with two or more genes in the biosynthetic gene cluster. In some embodiments, an ETaG is co-regulated with the biosynthetic gene cluster in that expression of the ETaG is increased, or turned on, when a biosynthetic product produced by the enzymes encoded by the biosynthetic gene cluster (a biosynthetic product of the biosynthetic gene cluster) is produced. In some embodiments, an ETaG is co-regulated with the biosynthetic gene cluster in that expression of the ETaG is increased, or turned on, when level of a biosynthetic product of the biosynthetic gene cluster is increased.

In some embodiments, an ETaG gene sequence is optionally more than about 10%, 20%, 30%, 40%, 50%, 60%, 70%, 80%, 85%, 90%, 95%, or 99% homologous to one or more gene sequences in the same genome. In some embodiments, an ETaG gene sequence is optionally more than about 10%, 20%, 30%, 40%, 50%, 60%, 70%, 80%, 85%, 90%, 95%, or 99% homologous to 2, 3, 4, 5, 6, 7, 8, 9 or more gene sequences in the same genome. In some embodiments, the homology is more than 10%. In some embodiments, the homology is more than 20%. In some embodiments, the homology is more than 30%. In some embodiments, the homology is more than 40%. In some embodiments, the homology is more than 50%. In some embodiments, the homology is more than 60%. In some embodiments, the homology is more than 70%. In some embodiments, the homology is more than 80%. In some embodiments, the homology is more than 90%. Certain examples are presented in the Figures.

In some embodiments, an ETaG gene sequence is optionally no more than about 10%, 20%, 30%, 40%, 50%, 60%, 70%, 80%, 85%, 90%, 95%, or 99% identical to any expressed gene sequence in at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% fungal nucleic acid sequence in the set that is from a different fungal strain and comprises a homologous biosynthetic gene cluster. In some embodiments, an ETaG gene sequence is optionally no more than about 10%, 20%, 30%, 40%, 50%, 60%, 70%, 80%, 85%, 90%, 95%, or 99% identical to at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% fungal gene sequence that is within a proximity zone relative to a biosynthetic gene of a homologous biosynthetic gene cluster from a different fungal strain. In some embodiments, an ETaG gene sequence is optionally no more than about 10%, 20%, 30%, 40%, 50%, 60%, 70%, 80%, 85%, 90%, 95%, or 99% identical to at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% fungal gene sequence that is within a proximity zone relative to a biosynthetic gene of a homologous biosynthetic gene cluster from a different fungal strain. In some embodiments, an ETaG gene sequence is optionally no more than about 10%, 20%, 30%, 40%, 50%, 60%, 70%, 80%, 85%, 90%, 95%, or 99% identical to any expressed gene sequence in any fungal nucleic acid sequence in the set that is from a different fungal strain and comprises a homologous biosynthetic gene cluster. In some embodiments, an ETaG gene sequence is optionally no more than about 10%, 20%, 30%, 40%, 50%, 60%, 70%, 80%, 85%, 90%, 95%, or 99% identical to any expressed gene sequence that is within a proximity zone relative to a biosynthetic gene of a homologous biosynthetic gene cluster from a different fungal strain. In some embodiments, it is no more than about 10% identical. In some embodiments, it is no more than about 20% identical. In some embodiments, it is no more than about 30% identical. In some embodiments, it is no more than about 40% identical. In some embodiments, it is no more than about 50% identical. In some embodiments, it is no more than about 60% identical. In some embodiments, it is no more than about 70% identical. In some embodiments, it is no more than about 80% identical. In some embodiments, it is no more than about 90% identical.

In some embodiments, a human target gene and/or a product thereof is susceptible to modulation by a biosynthetic product, or an analog thereof, of a biosynthetic gene cluster, wherein the human target gene has its homologous ETaGs within the biosynthetic gene cluster or in a proximity zone relative to a biosynthetic gene of the cluster. In some embodiments, a protein encoded by a human target gene is susceptible to modulation by a biosynthetic product, or an analog thereof, of a biosynthetic gene cluster, wherein the human target gene has its homologous ETaGs within the biosynthetic gene cluster or in a proximity zone relative to a biosynthetic gene of the cluster. Thus, in some embodiments, the present disclosure not only provides novel human target, but also provides methods and agents for modulating such human targets.

In some embodiments, the present disclosure provides technologies, e.g., methods, databases, systems, etc., for identifying ETaGs and/or their medical relevance, e.g., their therapeutic relevance. In some embodiments, the present disclosures provide databases, optionally with various annotations, that are structured for efficient identification, search, use, etc. of ETaGs, related biosynthetic gene clusters, related biosynthetic products and/or analogs thereof of the biosynthetic gene clusters, the related homologous mammalian nucleic acid sequences (e.g., human genes), etc. Among other things, the present disclosure provides databases and/or sequences structured to improve computing efficiency and/or accuracy for, e.g., ETaG identification.

For example, in some embodiments, a provided database was constructed so that all the biosynthetic gene clusters were identified and annotated. Nucleic acid sequences for these clusters were then computationally excised from the rest of the nucleic acid sequences in the fungal genomes and databased. The resulting database of biosynthetic gene cluster was then used for ETaG searches. Among other things, when a hit in an ETaG search was identified using such a database, the hit was an ETaG because only sequences that were in biosynthetic clusters (or proximity zones thereof) were searched. Separating biosynthetic gene cluster sequences from the whole genome sequences improves the signal to noise ratio and vastly speeds up ETaG search processes. Among other things, compared to using provided databases, searches for ETaGs in whole fungal genome sequences frequently led to false positives where identified hits were "house-keeping" gene located in the genomes but not in biosynthetic gene cluster or proximity zones thereof. In some embodiments, an identified hit, e.g., ETaG, from provided technologies (e.g., methods, databases, etc.) is not a house-keeping gene. In some embodiments, an identified hit, e.g., ETaG, from provided technologies is or comprises a sequence that shares homology with a second nucleic acid sequence (e.g., a gene) or a portion thereof in the same genome. Sequence homology for sequences in the present disclosure can be at least 20%, 30%, 40%, 50%, 60%, 70%, 75%, 80%, 85%, 90%, 91%, 92%, 93%, 94%, 95%, 96%, 97%, 98%, 99% or 99.5%. In some embodiments, the homology is at least 50%; in some embodiments, at least 60%; in some embodiments, at least 70%; in some embodiments, at least 75%; in some embodiments, at least 80%; in some embodiments, at least 85%; in some embodiments, at least 90%; and in some embodiments, at least 95%. A portion of a sequence of the present disclosure can comprise at least 5, 6, 7, 8, 9, 10, 15, 20, 25, 30, 35, 40, 45, 50, 60, 70, 80, 90, 100, 150, 200, 250, 300, 350, 400, 450, 500, 600, 700, 800, 900 or 1000 amino acid residues for a protein sequence or nucleobases for a nucleic acid sequence. In some embodiments, a portion of a nucleic acid sequence is at least 10, 15, 20, 25, 30, 35, 40, 45, 50, 60, 70, 80, 90, 100, 150, 200, 250, 300, 350, 400, 450, 500, 600, 700, 800, 900 or 1000 nucleobases in length. In some embodiments, the length is at least 20 nucleobases. In some embodiments, the length is at least 30 nucleobases. In some embodiments, the length is at least 40 nucleobases. In some embodiments, the length is at least 50 nucleobases. In some embodiments, the length is at least 100 nucleobases. In some embodiments, the length is at least 150 nucleobases. In some embodiments, the length is at least 200 nucleobases. In some embodiments, the length is at least 300 nucleobases. In some embodiments, the length is at least 400 nucleobases. In some embodiments, the length is at least 500 nucleobases. In some embodiments, an identified hit, e.g., ETaG, from provided technologies is or comprises a sequence that encodes a product, e.g., a protein, that shares homology (e.g., at least 50%, 60%, 70%, 75%, 80%, 85%, 90%, 91%, 92%, 93%, 94%, 95%, 96%, 97%, 98%, 99% or 99.5%) with a product, or a portion thereof (e.g., a set of key residues of a protein, a protein domain, etc., as described in the present disclosure), encoded by a second nucleic acid sequence (e.g., gene) in the same genome. As described herein, homology/similarities can be assessed using a variety of technologies as appreciated by those skilled in the art. In some embodiments, a second nucleic acid sequence is or comprises a house-keeping gene. In some embodiments, a second nucleic acid sequence is shared among two or more species. In some embodiments, an ETaG while homologous to a second nucleic acid sequence differs from the second nucleic acid sequence in that the ETaG encodes a product (e.g., a protein) that provides resistance to a product of its corresponding biosynthetic cluster (e.g., a small molecule) while the second nucleic acid sequence does not.

In some embodiments, the present disclosure provides a system comprising:

one or more non-transitory machine-readable storage media storing data representing a set of nucleic acid sequences, each of which is found in a fungal strain and comprises a biosynthetic gene cluster.

In some embodiments, the present disclosure provides a system comprising:

one or more non-transitory machine-readable storage media storing data representing a set of nucleic acid sequences, each of which is or comprises a ETaG sequence.

In some embodiments, at least 10, 20, 50, 100, 200, or 500, or at least 5%, 10%, 20%, 30%, 40%, 50%, 60%, 70%, 80%, 90%, or 95%, or all, of the nucleic acid sequences of a set comprise ETaGs, which are indexed and/or annotated. In some embodiments, provided systems can greatly improve computing efficiency, as it is structured to greatly reduce the amount of data to be processed. For example, instead of processing all genomic or biosynthetic gene cluster sequence data of one or more (in some cases, hundreds or thousands or even more) fungi genomes to search for an ETaG, provided systems can search only genes indexed/marked as ETaGs, thereby saving time and cost used for processing sequences not indexed as ETaGs. Additionally and alternatively, an ETaG can be independently annotated with information such as its related biosynthetic gene cluster (which contains a biosynthetic gene the proximity zone relative to which the ETaG is within), structures of the biosynthetic products of the related biosynthetic gene cluster, and/or human homologs of the ETaG, etc. In some embodiments, at least 10, 20, 50, 100, 200, or 500, or at least 5%, 10%, 20%, 30%, 40%, 50%, 60%, 70%, 80%, 90%, or 95%, or all, of ETaGs of a set are independently annotated, with at least one of the following: a related biosynthetic gene cluster, and a human homolog of the ETaG. In some embodiments, at least 10, 20, 50, 100, 200, or 500, or at least 5%, 10%, 20%, 30%, 40%, 50%, 60%, 70%, 80%, 90%, or 95%, or all, of ETaGs of a set are independently annotated, with at least one of the following: a related biosynthetic gene cluster, a biosynthetic product of the related biosynthetic gene cluster, and a human homolog of the ETaG. In some embodiments, by structuring sequence data with ETaG index and annotation, provided systems can provide a number of advantages. For example, in some embodiments, provided systems provide fast access to ETaGs with useful related information, for example, their related biosynthetic gene clusters and human homologs, and vice versa, while maintaining data size and cost low.

In some embodiments, provided methods and systems are useful for human target identification and/or characterization, as, among other things, provided methods and systems provide connections between biosynthetic gene clusters, ETaGs, and human target genes. In some embodiments, the present disclosure provides insights particularly into targets that were considered undruggable prior to the present disclosure, by providing their homologous ETaGs in fungi and the related biosynthetic gene clusters. In some embodiments, the present disclosure greatly improves drugability of targets that were considered undruggable prior to the present disclosure, in some cases, essentially converting them into druggable targets, by, for example, their homologous ETaGs in fungi, the related biosynthetic gene clusters, the biosynthetic products of the related biosynthetic gene clusters (which can be directly used as modulators, and/or whose analogs can be used as modulators, of the human targets).

In some embodiments, the present disclosure provides methods for identifying and/or characterizing a human target of a biosynthetic product of a biosynthetic gene cluster, or an analog of the product.

In some embodiments, the present disclosure provides methods comprising:
identifying a human homolog of an ETaG that is within a proximity zone relative to at least one gene of a biosynthetic gene cluster, or is within a proximity zone relative to at least one gene of a second biosynthetic gene cluster which second biosynthetic gene cluster encodes enzymes that produce the biosynthetic product that is produced by the enzymes encoded by the biosynthetic gene cluster; and
optionally assaying an effect of the biosynthetic product produced by the enzymes encoded by the biosynthetic gene cluster, or an analog of the product, on the human target.

In some embodiments, the present disclosure provides methods comprising:
identifying a human homolog of an ETaG that is within a proximity zone relative to at least one biosynthetic gene of a biosynthetic gene cluster, or is within a proximity zone relative to at least one biosynthetic gene of a second biosynthetic gene cluster which second biosynthetic gene cluster encodes enzymes that produce the biosynthetic product that is produced by the enzymes encoded by the biosynthetic gene cluster; and
optionally assaying an effect of the biosynthetic product produced by the enzymes encoded by the biosynthetic gene cluster, or an analog of the product, on the human target.

In some embodiments, the present disclosure provides methods comprising:
identifying a human homolog of an ETaG that is within a proximity zone relative to at least one gene of a biosynthetic gene cluster; and
optionally assaying an effect of the biosynthetic product produced by the enzymes encoded by the biosynthetic gene cluster, or an analog of the product, on the human target.

In some embodiments, the present disclosure provides methods comprising:
identifying a human homolog of an ETaG that is within a proximity zone relative to at least one biosynthetic gene of a biosynthetic gene cluster; and
optionally assaying an effect of the biosynthetic product produced by the enzymes encoded by the biosynthetic gene cluster, or an analog of the product, on the human target.

In some embodiments, for biosynthetic gene clusters comprising no biosynthetic genes the proximity zones relative to which contain ETaGs, the mammalian targets, e.g., human targets, of the products (and/or analogs thereof) of such biosynthetic gene clusters can be identified through an ETaG that is in a proximity zone relative to a biosynthetic gene of a second biosynthetic gene cluster that encodes the enzymes producing the same biosynthetic product. In some embodiments, the second biosynthetic gene cluster is in a different organism. In some embodiments, the second biosynthetic gene cluster is in a different fungi strain.

In some embodiments, the present disclosure provides methods for identifying and/or characterizing a human target of a biosynthetic product of a biosynthetic gene cluster, or an analog of the product, comprising:
identifying a human homolog of an ETaG that is within a proximity zone relative to at least one biosynthetic gene of a second biosynthetic gene cluster which second biosynthetic gene cluster encodes enzymes that produce the same biosynthetic product that is produced by the enzymes encoded by the biosynthetic gene cluster; and
optionally assaying an effect of the biosynthetic product produced by the enzymes encoded by the biosynthetic gene cluster, or an analog of the product, on the human target.

In some embodiments, provided technologies are useful for assessing interactions of human targets with compounds. In some embodiments, the present disclosure provides methods for accessing interaction of a human target with a compound, comprising:
comparing nucleic acid sequence of the human target, or the nucleic acid sequence that encodes the human target, with a set of nucleic acid sequences which comprise one or more ETaGs.

In some embodiments, homology with ETaGs (nucleic acid level or protein level, including portions thereof) directs to the related biosynthetic gene clusters of the ETaGs and the biosynthetic products thereof. In some embodiments, such connection between biosynthetic products and human targets indicates interaction and/or modulation of the human targets or products encoded thereby. In some embodiments, such biosynthetic products interact with and/or modulate the human targets or products encoded thereby.

In some embodiments, provided technologies are useful for designing and/or providing modulators for human targets, as, among other things, provided technologies provide connections between biosynthetic gene clusters, ETaGs, and human target genes.

In some embodiments, the present disclosure provides a compound, which compound is a product of enzymes encoded by a biosynthetic gene cluster, wherein, within a proximity zone relative to at least one gene in the biosynthetic gene cluster, exists an ETaG that:
is homologous to the human target, or a nucleic acid sequence that encodes the human target; and
is optionally co-regulated with at least one biosynthetic gene in the cluster.

In some embodiments, a provided compound is a product of enzymes encoded by a provided biosynthetic gene cluster. In some embodiments, a provided compound is an analog of a product of enzymes encoded by a provided biosynthetic gene cluster. In some embodiments, a provided biosynthetic gene cluster comprises one or more biosynthetic genes presented in one of FIGS. 5-12 and 20-39. In some embodiments, a provided biosynthetic gene cluster is one of FIGS. 5-12 and 20-39. In some embodiments, a provided compound is a product of enzymes encoded by a provided biosynthetic gene cluster presented in one of FIGS. 5-12 and 20-39. In some embodiments, a provided compound is a product of a provided biosynthetic gene cluster presented in one of FIGS. 5-12 and 20-39, or a biosynthetic gene cluster comprising one or more biosynthetic genes presented in one of FIGS. 5-12 and 20-39. In some embodiments, a provided compound is a product of a provided biosynthetic gene cluster presented in one of FIGS. 5-12 and 20-39. In some embodiments, a provided compound is a product of a provided biosynthetic gene cluster comprising one or more biosynthetic genes presented in one of FIGS. 5-12 and 20-39. In some embodiments, a provided compound is an analog of a product of enzymes encoded by a provided biosynthetic gene cluster presented in one of FIGS. 5-12 and 20-39. In some embodiments, a provided compound is an analog of a product of a provided biosynthetic gene cluster comprising one or more biosynthetic genes presented in one of FIGS. 5-12 and 20-39. In some embodiments, a provided compound modulates a function of a human target. In some embodiments, the present disclosure provides pharmaceutical compositions of provided compounds. In some embodiments, the present disclosure provides pharmaceutical compositions comprising a provided compound or a pharmaceutically acceptable salt thereof. In some embodiments, the present disclosure provides pharmaceutical compositions comprising a provided compound or a pharmaceutically acceptable salt thereof, and a pharmaceutically acceptable carrier. In some embodiments, a provided compound in a provided composition is an analog of a product of enzymes encoded by the biosynthetic gene cluster or a salt thereof. In some embodiments, a provided compound in a provided composition is an unnatural salt of a product of enzymes encoded by the biosynthetic gene cluster.

In some embodiments, the present disclosure provides methods for identifying and/or characterizing a modulator of a human target, comprising:

providing a product or an analog thereof, which product is produced by enzymes encoded by a biosynthetic gene cluster, wherein, within a proximity zone relative to at least one gene in the biosynthetic gene cluster, exists an ETaG that:

is homologous to the human target, or a nucleic acid sequence that encodes the human target; and is optionally co-regulated with at least one biosynthetic gene in the cluster.

In some embodiments, the present disclosure provides methods for identifying and/or characterizing a modulator of a human target, comprising:

providing a product or an analog thereof, which product is produced by enzymes encoded by a biosynthetic gene cluster, wherein, within a proximity zone relative to at least one biosynthetic gene in the biosynthetic gene cluster, exists an ETaG that:

is homologous to the human target, or a nucleic acid sequence that encodes the human target; and is optionally co-regulated with at least one biosynthetic gene in the cluster.

In some embodiments, the present disclosure provides methods for modulating a human target, comprising:

providing a product or an analog thereof, which product is produced by enzymes encoded by a biosynthetic gene cluster, wherein, within a proximity zone relative to at least one gene in the biosynthetic gene cluster, exists an ETaG that:

is homologous to the human target, or a nucleic acid sequence that encodes the human target; and is optionally co-regulated with at least one biosynthetic gene in the cluster.

In some embodiments, the present disclosure provides methods for modulating a human target, comprising:

providing a product or an analog thereof, which product is produced by enzymes encoded by a biosynthetic gene cluster, wherein, within a proximity zone relative to at least one biosynthetic gene in the biosynthetic gene cluster, exists an ETaG that:

is homologous to the human target, or a nucleic acid sequence that encodes the human target; and is optionally co-regulated with at least one biosynthetic gene in the cluster.

In some embodiments, the present disclosure provides methods for treating a condition, disorder or disease associated with a human target, comprising administering to a subject susceptible to or suffering therefrom a biosynthetic product or an analog thereof, wherein:

the biosynthetic product is of a biosynthetic gene cluster, wherein, within a proximity zone relative to at least one gene in the biosynthetic gene cluster, exists an ETaG that:

is homologous to the human target, or a nucleic acid sequence that encodes the human target; and is optionally co-regulated with at least one biosynthetic gene in the cluster.

In some embodiments, the present disclosure provides methods for treating a condition, disorder or disease associated with a human target, comprising administering to a subject susceptible to or suffering therefrom a biosynthetic product or an analog thereof, wherein:

the biosynthetic product is of a biosynthetic gene cluster, wherein, within a proximity zone relative to at least one biosynthetic gene in the biosynthetic gene cluster, exists an ETaG that:

is homologous to the human target, or a nucleic acid sequence that encodes the human target; and is optionally co-regulated with at least one biosynthetic gene in the cluster.

In some embodiments, a human target is a Ras protein. In some embodiments, a human target comprises a RasGEF domain. In some embodiments, a human target comprise a RasGAP domain.

In some embodiments, an ETaG is identified by a provided method.

In some embodiments, a product (e.g., a biosynthetic product) is produced by a fungi. In some embodiments, a product is acyclic. In some embodiments, a product is a polyketide. In some embodiments, a product is a terpene compound. In some embodiments, a product is non-ribosomally synthesized.

In some embodiments, an analog a substance that shares one or more particular structural features, elements, components, or moieties with a reference substance. Typically, an analog shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance. In some embodiments, an analog of a substance is the substance being substituted at one or more of its substitutable positions.

In some embodiments, an analog of a product comprises the structural core of a product. In some embodiments, a biosynthetic product is cyclic, e.g., monocyclic, bicyclic, or polycyclic, and the structural core of the product is or comprises the monocyclic, bicyclic, or polycyclic ring system. In some embodiments, a product is or comprises a polypeptide, and a structural core is the backbone of the polypeptide. In some embodiments, a product is or comprises a polyketide, and a structural core is the backbone of the polyketide.

In some embodiments, an analog is a substituted biosynthetic product. In some embodiments, an analog is or comprises the structural core substituted with one or more substituents as described herein.

In some embodiments, the present disclosure provides compositions of biosynthetic products, or analogs thereof, of provided biosynthetic gene clusters wherein an ETaG exists within the proximity zone relative to at least one gene of the biosynthetic gene cluster. In some embodiments, a provided composition is a pharmaceutical composition. In some embodiments, a provided pharmaceutical composition comprises a pharmaceutically acceptable salt of a biosynthetic product, or an analog thereof, of a provided biosynthetic gene cluster wherein an ETaG exists within the proximity zone relative to at least one gene of the biosynthetic gene cluster, and a pharmaceutically acceptable carrier.

In some embodiments, two events or entities are associated with one another if the presence, level and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population).

In some embodiments, a disease is cancer. In some embodiments, a disease is an infectious disease. In some embodiments, a disease is a heart disease. In some embodiments, a disease is associated with level of a lipid, protein, human metabolite, etc.

BRIEF DESCRIPTION OF THE DRAWING

FIG. 13 depicts alignments of human Ras genes and certain identified Ras ETaGs. As shown, the human Ras genes and the presented ETaGs share the same amino acid residues at many locations of the KRAS nucleotide binding residues.

FIG. 14 depicts alignments of human Ras genes and certain identified Ras ETaGs. As shown, the human Ras genes and the presented ETaGs share the same amino acid residues at many locations of the KRAS residues that are within 4 Å of BRAF.

FIG. 15 depicts alignments of human Ras genes and certain identified Ras ETaGs. As shown, the human Ras genes and the presented ETaGs share the same amino acid residues at many locations of the KRAS residues that are within 4 Å of rasGAP.

FIG. 16 depicts alignments of human Ras genes and certain identified Ras ETaGs. As shown, the human Ras genes and the presented ETaGs share the same amino acid residues at many locations of the KRAS residues that are within 4 Å of SOS.

FIG. 19 depicts sequence alignment of Sec7. (A) Example Brefeldin A interacting Residues. (B) Example sequence alignment.

FIG. 36 depicts example biosynthetic gene clusters related to RasGAP, e.g., from *Corynespora cassiicola* UM 591 and *Magnaporthe oryzae* strain SV9610. Illustrated RasGAP homologs are indicated in black.

DETAILED DESCRIPTION OF CERTAIN EMBODIMENTS

1. Definitions

Figure 1:
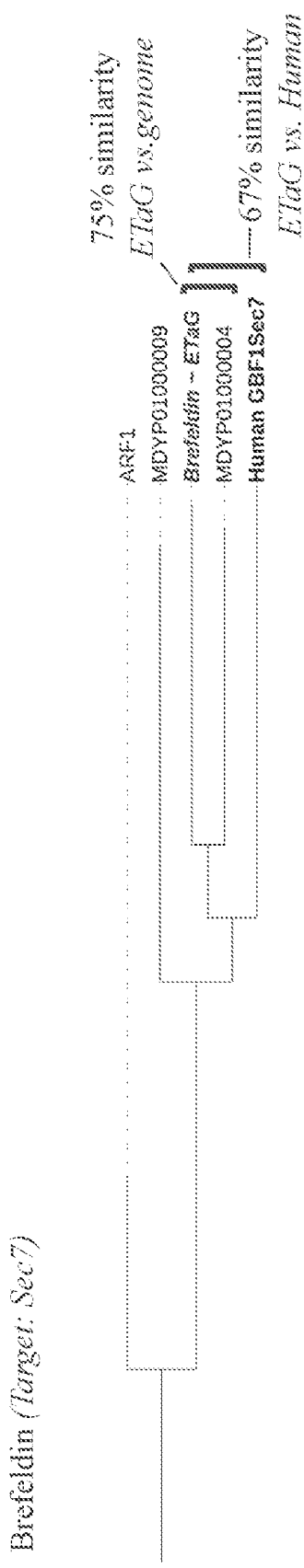
FIG. 1 depicts a Brefeldin A ETaG identified in *Penicillium vulpinum* IBT 29486. The example ETaG identified is the Sec7 guanine-nucleotide-exchange-factor superfamily (pfam01369). Sequence similarity is of the Sec7 domain calculated using MUSCLE alignment algorithm.
Figure 2:
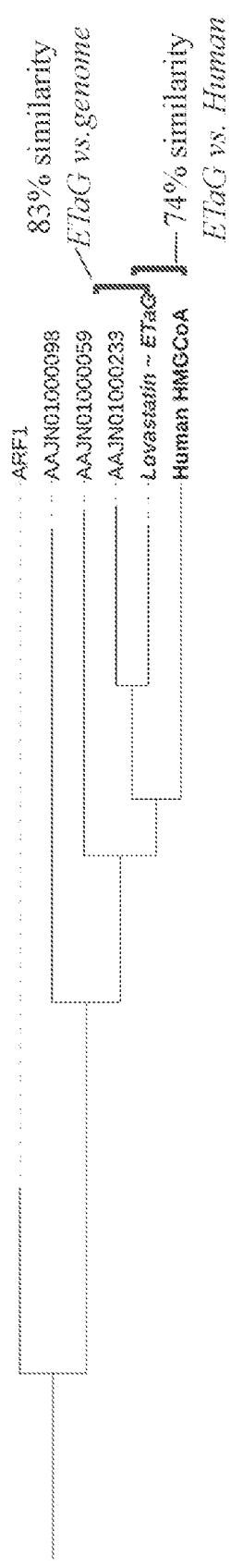
FIG. 2 depicts a Lovastatin ETaG identified in *Aspergillus terreus* ATCC 20542. The example ETaG identified is hydroxymethylglutaryl-coenzyme A reductase (HMG-CoA; pfam00368). Sequence similarity is of the HMG-CoA domain calculated using MUSCLE alignment algorithm.
Figure 3:
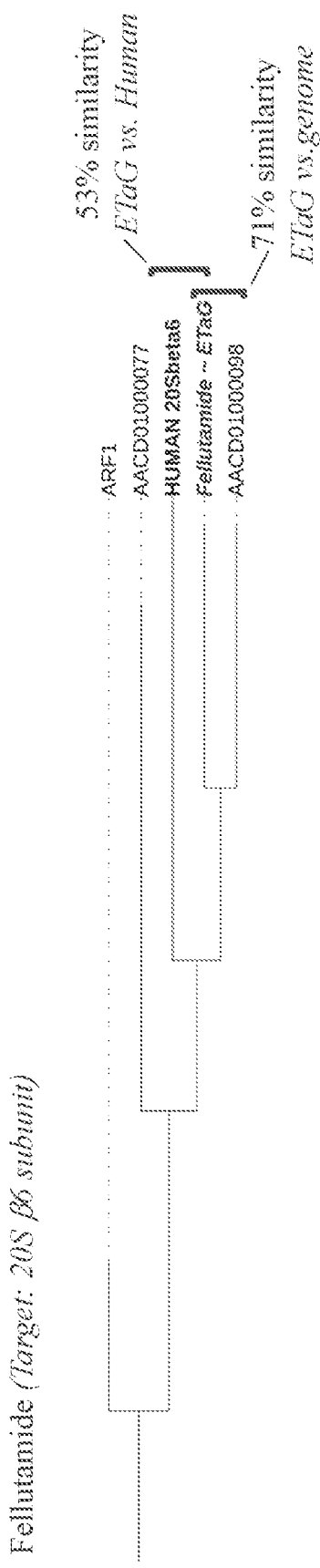
FIG. 3 depicts a Fellutamide ETaG identified in *Aspergillus nidulans* FGSC A4. The example ETaG identified is proteasome 20S beta-subunit (pfam00227). Sequence similarity is of the 20S beta-calculated using MUSCLE alignment algorithm.
Figure 4:
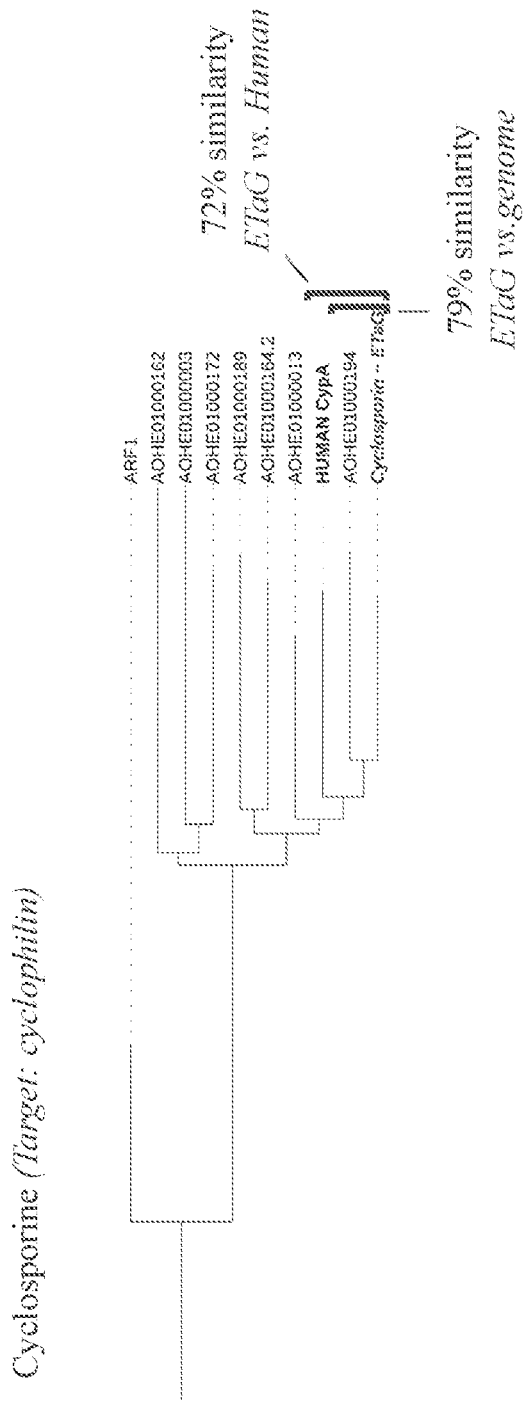
FIG. 4 depicts a Cyclosporine ETaG identified in *Tolypocladium inflatum* NRRL 8044. The example ETaG identified is the cyclophilin type peptidyl-prolyl cis-trans isomerase (pfam00160). Sequence similarity is of the cyclophilin domain calculated using MUSCLE alignment algorithm.

As used herein, the following definitions shall apply unless otherwise indicated. For purposes of this disclosure, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001.

Aliphatic: As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation, or combinations thereof. Unless otherwise specified, aliphatic groups contain 1-100 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Aryl: The term "aryl" used alone or as part of a larger moiety as in "aralkyl," "aralkoxy," or "aryloxyalkyl," refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" may be used interchangeably with the term "aryl ring." In certain embodiments of the present disclosure, "aryl" refers to an aromatic ring system which includes, but not limited to, phenyl, biphenyl, naphthyl, binaphthyl, anthracyl and the like, which may bear one or more substituents. In some embodiments, also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like, where a radical or point of attachment is on an aryl ring.

Cycloaliphatic: The term "cycloaliphatic," as used herein, refers to saturated or partially unsaturated aliphatic monocyclic, bicyclic, or polycyclic ring systems having, e.g., from 3 to 30, members, wherein the aliphatic ring system is optionally substituted. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic" may also include aliphatic rings that are fused to one or more aromatic or nonaromatic rings, such as decahydronaphthyl or tetrahydronaphthyl, where a radical or point of attachment is on an aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, or a $C_9$-$C_{16}$ tricyclic hydrocarbon that is completely saturated or that contains one or more units of unsaturation, but which is not aromatic.

Halogen: The term "halogen" means F, Cl, Br, or I.

Heteroaliphatic: The term "heteroaliphatic" is given its ordinary meaning in the art and refers to aliphatic groups as described herein in which one or more carbon atoms are replaced with one or more heteroatoms (e.g., oxygen, nitrogen, sulfur, silicon, phosphorus, and the like).

Heteroalkyl: The term "heteroalkyl" is given its ordinary meaning in the art and refers to alkyl groups as described herein in which one or more carbon atoms is replaced with a heteroatom (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

Heteroaryl: The terms "heteroaryl" and "heteroar-," used alone or as part of a larger moiety, e.g., "heteroaralkyl," or "heteroaralkoxy," refer to monocyclic, bicyclic or polycyclic ring systems having, for example, a total of five to thirty, ring members, wherein at least one ring in the system is aromatic and at least one aromatic ring atom is a heteroatom. In some embodiments, a heteroatom is nitrogen, oxygen or sulfur. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where a radical or point of attachment is on a heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

Heteroatom: The term "heteroatom" means an atom that is not carbon or hydrogen. In some embodiments, a heteroatom is oxygen, sulfur, nitrogen, phosphorus, boron or silicon (including any oxidized form of nitrogen, sulfur, phosphorus, or silicon; the quaternized form of any basic nitrogen or a substitutable nitrogen of a heterocyclic ring (for example, N as in 3,4-dihydro-2H-pyrrolyl), NH (as in pyrrolidinyl) or $NR^+$ (as in N-substituted pyrrolidinyl); etc.). In some embodiments, a heteroatom is boron, nitrogen, oxygen, silicon, sulfur, or phosphorus. In some embodiments, a heteroatom is nitrogen, oxygen, silicon, sulfur, or phosphorus. In some embodiments, a heteroatom is nitrogen, oxygen, sulfur, or phosphorus. In some embodiments, a heteroatom is nitrogen, oxygen or sulfur.

Heterocyclyl: As used herein, the terms "heterocycle," "heterocyclyl," "heterocyclic radical," and "heterocyclic ring" are used interchangeably and refer to a monocyclic, bicyclic or polycyclic ring moiety (e.g., 3-30 membered) that is saturated or partially unsaturated and has one or more heteroatom ring atoms. In some embodiments, a heteroatom is boron, nitrogen, oxygen, silicon, sulfur, or phosphorus. In some embodiments, a heteroatom is nitrogen, oxygen, silicon, sulfur, or phosphorus. In some embodiments, a heteroatom is nitrogen, oxygen, sulfur, or phosphorus. In some embodiments, a heteroatom is nitrogen, oxygen or sulfur. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where a radical or point of attachment is on a heteroaliphatic ring. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

Partially unsaturated: As used herein, the term "partially unsaturated" refers to a moiety that includes at least one double or triple bond. The term "partially unsaturated" is intended to encompass groups having multiple sites of unsaturation, but is not intended to include aryl or heteroaryl moieties.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known. For example, S. M. Berge, et al. describes pharmaceutically acceptable salts in detail in J. Pharmaceutical Sciences, 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other known methods such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, pharmaceutically acceptable salts include, but are not limited to, nontoxic base addition salts, such as those formed by acidic groups of provided compounds (e.g., phosphate linkage groups of oligonucleotides, phosphorothioate linkage groups of oligonucleotides, etc.) with bases. Representative alkali or alkaline earth metal salts include salts of sodium, lithium, potassium, calcium, magnesium, and the like. In some embodiments, pharmaceutically acceptable salts are ammonium salts (e.g., —N(R)$_3^+$). In some embodiments, pharmaceutically acceptable salts are sodium salts. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Protecting Group: The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 5th ed.; John Wiley and Sons: Hoboken, N.J., 2014). Exemplary protecting groups (and associated protected moieties) are described in detail below.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates, allyl ethers, ethers, silyl ethers, alkyl ethers, arylalkyl ethers, and alkoxyalkyl ethers. Examples of suitable esters include formates, acetates, propionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenyl sulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5] azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Substitution: As described herein, compounds of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. In some embodiments, example substituents are described below.

Suitable monovalent substituents are halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)N(R°)$_2$; —N(R°)C(S)N(R°)$_2$; —(CH$_2$)$_{0-4}$N(R°)C(O)OR°; —N(R°)N(R°)C(O)R°; —N(R°)N(R°)C(O)N(R°)$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSi(R°)$_3$; —(CH$_2$)$_{0-4}$OC(O)R°; —OC(O)(CH$_2$)$_{0-4}$SR°, —SC(S)SR°; —(CH$_2$)$_{0-4}$SC(O)R°; —(CH$_2$)$_{0-4}$C(O)N(R°)$_2$; —C(S)N(R°)$_2$; —C(S)SR°; —SC(S)SR°, —(CH$_2$)$_{0-4}$OC(O)N(R°)$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$N(R°)$_2$; —(CH$_2$)$_{0-4}$S(O)R°; —N(R°)S(O)$_2$N(R°)$_2$; —N(R°)S(O)$_2$R°; —N(OR°)R°; —C(NH)N(R°)$_2$; —Si(R°)$_3$; —OSi(R°)$_3$; —P(R°)$_2$; —P(OR°)$_2$; —OP(R°)$_2$; —OP(OR°)$_2$; —N(R°)P(R°)$_2$; —B(R°)$_2$; —OB(R°)$_2$; —P(O)(R°)$_2$; —OP(O)(R°)$_2$; —N(R°)P(O)(R°)$_2$; —(C$_{1-4}$ straight or branched alkylene)O—N(R°)$_2$; or —(C$_{1-4}$ straight or branched alkylene)C(O)O—N(R°)$_2$; wherein each R° may be substituted as defined below and is independently hydrogen, C$_{1-20}$ aliphatic, C$_{1-20}$ heteroaliphatic having 1-5 heteroatoms independently selected from nitrogen, oxygen, sulfur, silicon and phosphorus, —CH$_2$—(C$_{6-14}$ aryl), —O(CH$_2$)$_{0-1}$(C$_{6-14}$ aryl), —CH$_2$-

(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of R°, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on R° (or the ring formed by taking two independent occurrences of R° together with their intervening atoms), are independently halogen, —(CH$_2$)$_{0-2}$R$^•$, -(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR, —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•$$_2$, —NO$_2$, —SiR$^•$$_3$, —OSiR$^•$$_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents are the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* are halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•$$_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

In some embodiments, suitable substituents on a substitutable nitrogen are —R$^†$, —NR$^†$$_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†$$_2$, —C(S)NR$^†$$_2$, —C(NH)NR$^†$$_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•$$_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Unsaturated: The term "unsaturated" as used herein, means that a moiety has one or more units of unsaturation.

Unless otherwise specified, salts, such as pharmaceutically acceptable acid or base addition salts, stereoisomeric forms, and tautomeric forms, of provided compound are included.

2. Detailed Description of Certain Embodiments

Among other things, the present disclosure encompasses the recognition that many products produced by enzymes encoded by fungi biosynthetic gene clusters may be employed to develop therapeutics toward human targets to treat various diseases. The present disclosure recognizes that one challenge of using the fungi products is to identifying their human targets. In some embodiments, the present disclosure provides technologies for efficient identification of human targets of biosynthetic products produced by enzymes encoded by fungi biosynthetic gene clusters. In some embodiments, a provided technology identifies embedded target genes (ETaGs) in proximity zones of biosynthetic genes of biosynthetic gene clusters, and optionally further identifies human targets of biosynthetic products produced by enzymes encoded by the biosynthetic gene clusters by comparing the ETaG sequences with human nucleic acid sequences, particularly expressed human nucleic acid sequences, including human genes encoding proteins. As readily appreciated by those skilled in the art, the connection between the biosynthetic products from biosynthetic gene clusters, ETaGs, and human targets, once established, can be utilized in various methods. For example, one may start from a biosynthetic product produced by the enzymes encoded by a biosynthetic gene cluster, to an ETaG within proximity zones of a biosynthetic gene of the biosynthetic gene cluster, and then to a human target that is homologous to the ETaG. Once the human target is identified, one can prioritize it (even if it was previously considered undruggable), and develop modulators of the human target using the biosynthetic product, including optional further optimization of the biosynthetic product, for medical use, e.g., by preparing and assaying analogs of the product, using many methods available to those skilled in the art. One may also start from a human target of therapeutic interest, to an ETaG homologous to the human target, then to a biosynthetic gene cluster that contains a biosynthetic gene a proximity zone relative to which contains the ETaG. Once the biosynthetic gene cluster is identified, the biosynthetic product produced by the enzymes encoded by the biosynthetic gene cluster can be characterized and assayed for modulation of the human target or a product thereof. The biosynthetic product can be used as a lead for optimization using a number of methods in the art in accordance with the present disclosure to provide agents useful for many medical, e.g. therapeutics purposes.

Without the intention to be limited by any theory, in some embodiments, the present disclosure encompasses the recognition that ETaGs from eukaryotes and/or products encoded thereby may bear more similarities to mammalian genes and/or products encoded thereby than, for example, their counterparts, in any, in prokaryotes such as bacteria; in some embodiments, eukaryotic ETaGs can be more therapeutically relevant. In some embodiments, ETaGs in fungi may be particularly useful for developing human therapeutics in view of the relative closeness of fungi with mammalians in a phylogenetic tree.

In some embodiments, the present disclosure provides technologies for identifying and/or characterizing ETaGs, which are non-biosynthetic genes in that they are not necessarily involved in synthesis of the products produced by the enzymes encoded by the biosynthetic gene clusters that contain the ETaGs, or the proximity zones relative to whose genes, in some embodiments, biosynthetic genes, contain the ETaGs (enzymes encoded by the biosynthetic gene cluster can produce the biosynthetic product without the ETaG). In some embodiments, ETaGs are not required for the synthesis of the products produced by the enzymes encoded by the biosynthetic gene clusters that contain the ETaGs, or the proximity zones relative to whose genes, in some embodiments, biosynthetic genes, contain the ETaGs (enzymes encoded by the biosynthetic gene cluster can produce the biosynthetic product without the ETaG). In some embodiments, ETaGs are not involved in synthesis of the products produced by the enzymes encoded by the biosynthetic gene clusters that contain the ETaGs, or the proximity zones relative to whose genes, in some embodiments, biosynthetic genes, contain the ETaGs (enzymes encoded by the biosynthetic gene cluster can produce the biosynthetic product without the ETaG). In some embodiments, ETaGs are homologous or comprise sequences that are homologous to human genes, e.g., sharing at least 50%, 55%, 60%, 65%, 70%, 75%, 80%, 85%, 90%, or 95% homology with human proteins or sequences (e.g., functional and/or structural units such as domains, functional structural features (helixes, sheets, etc.), etc.).

In some embodiments, an ETaG is co-regulated with at least one biosynthetic gene in the biosynthetic gene cluster. In some embodiments, an ETaG is co-regulated with the biosynthetic gene cluster in that the expression of the ETaG is correlated to production of the product encoded by the enzymes of the biosynthetic gene cluster. In some embodiments, an ETaG provides a self-protective function. In some embodiments, an ETaG encodes a transporter of the product produced by the enzymes of the biosynthetic gene cluster. In some embodiments, an ETaG encodes a product, e.g., a protein, that can detoxify the product produced by the enzymes of the biosynthetic gene cluster. In some embodiments, an ETaG encodes a resistant variant of a protein whose activities are targeted by the product produced by the enzymes of the biosynthetic gene cluster.

In some embodiments, the present disclosure provides methods comprising:
querying a set of nucleic acid sequences, each of which is found in a fungal strain and comprises a biosynthetic gene cluster; and
identifying within at least one of the fungal nucleic acid sequences an embedded target gene (ETaG) sequence characterized in that it:
is not involved in synthesis of the product produced by the enzymes encoded by the biosynthetic gene cluster;
is within a proximity zone relative to at least one biosynthetic gene in the biosynthetic gene cluster; and
is optionally co-regulated with at least one biosynthetic gene in the biosynthetic gene cluster.

In some embodiments, an ETaG is homologous to a mammalian nucleic acid sequence. In some embodiments, the present disclosure provides methods comprising:
querying a set of nucleic acid sequences, each of which is found in a fungal strain and comprises a biosynthetic gene cluster; and
identifying within at least one of the fungal nucleic acid sequences an embedded target gene (ETaG) sequence characterized in that it:
is not involved in synthesis of the products produced by the enzymes encoded by the biosynthetic gene cluster;
is within a proximity zone relative to at least one biosynthetic gene in the biosynthetic gene cluster;
is homologous to an expressed mammalian nucleic acid sequence; and
is optionally co-regulated with at least one biosynthetic gene in the biosynthetic gene cluster.

Proximity Zone

In some embodiments, an ETaG is typically within a proximity zone relative to at least one gene in a biosynthetic gene cluster. In some embodiments, an ETaG is within a proximity zone relative to at least one biosynthetic gene in a biosynthetic gene cluster. In some embodiments, a proximity zone is no more than 1-100 kb upstream or downstream of a gene. In some embodiments, a proximity zone is no more than 1-50 kb upstream or downstream of a gene. In some embodiments, a proximity zone is no more than 1, 2, 3, 4, 5, 6, 7, 8, 9, 10, 15, 20, 25, 30, 35, 40, 45, 50, 60, 70, 80 or 90 kb upstream or downstream of a gene. In some embodiments, a proximity zone is no more than 1 kb upstream or downstream of a gene. In some embodiments, a proximity zone is no more than 5 kb upstream or downstream of a gene. In some embodiments, a proximity zone is no more than 10 kb upstream or downstream of a gene. In some embodiments, a proximity zone is no more than 15 kb upstream or downstream of a gene. In some embodiments, a proximity zone is no more than 20 kb upstream or downstream of a gene. In some embodiments, a proximity zone is no more than 25 kb upstream or downstream of a gene. In some embodiments, a proximity zone is no more than 30 kb upstream or downstream of a gene. In some embodiments, a proximity zone is no more than 35 kb upstream or downstream of a gene. In some embodiments, a proximity zone is no more than 40 kb upstream or downstream of a gene. In some embodiments, a proximity zone is no more than 45 kb upstream or downstream of a gene. In some embodiments, a proximity zone is no more than 50 kb upstream or downstream of a gene.

In some embodiments, an ETaG is within a biosynthetic gene cluster. In some embodiments, an ETaG is not within a region defined by the first and last genes of a biosynthetic gene cluster, but within a proximity zone relative to the first or last gene of a biosynthetic gene cluster.

Homology

In some embodiments, an ETaG is homologous to an expressed mammalian nucleic acid sequence. In some embodiments, a mammalian nucleic acid sequence is an expressed mammalian nucleic sequence. In some embodiments, a mammalian nucleic acid sequence is a mammalian gene. In some embodiments, a mammalian nucleic acid sequence is an expressed mammalian gene. In some embodiments, a mammalian nucleic acid is a human nucleic acid sequence. In some embodiments, a human nucleic acid sequence is an expressed human nucleic acid sequence. In some embodiments, a human nucleic acid sequence is a human gene. In some embodiments, a human nucleic acid sequence is an expressed human gene. In some embodiments, a human nucleic acid sequence is, or encodes a product which is, an existing target of therapeutic interest. In some embodiments, a human nucleic acid sequence is, or encodes a product which is, a novel target of therapeutic interest. In some embodiments, a human nucleic acid sequence is, or encodes a product which is, a target considered undruggable prior to the present disclosure. In some embodiments, a human nucleic acid sequence is, or encodes a product which is, a target considered undruggable by small molecules prior to the present disclosure. In some embodiments, the present disclosure provides unexpected findings that targets traditionally considered undruggable can be effectively modulated or targeted by small molecules which are the biosynthetic products, or analogs of the biosynthetic products, produced by the enzymes encoded by biosynthetic gene clusters, which biosynthetic gene clusters contain biosynthetic genes the proximity zones relative to which contain ETaGs (or portions thereof, or products encoded thereby and/or portions thereof) that are homologous to the targets.

In some embodiments, the present disclosure provides methods comprising: querying a set of nucleic acid sequences, each of which is found in a fungal strain and comprises a biosynthetic gene cluster; and identifying within at least one of the fungal nucleic acid sequences an embedded target gene (ETaG) characterized in that it:
   is not involved in synthesis of the products produced by the enzymes encoded by the biosynthetic gene cluster;
   is within a proximity zone relative to at least one biosynthetic gene in the biosynthetic gene cluster;
   is homologous to an expressed human nucleic acid sequence; and
   is optionally co-regulated with at least one biosynthetic gene in the biosynthetic gene cluster.

In some embodiments, an ETaG and a nucleic acid sequence shares nucleic acid sequence homology. In some embodiments, an ETaG sequence is homologous to another nucleic acid sequence (e.g., an expressed human nucleic acid sequence) in that the ETaG nucleic acid sequence or a portion thereof shares similarity on the level of nucleic acid base sequences with another nucleic acid sequence or a portion thereof. In some embodiments, the sequence of an ETaG shares nucleic acid base sequence similarity with another nucleic acid sequence. In some embodiments, a portion of the sequence of an ETaG shares nucleic acid base sequence similarity with a portion of another nucleic acid sequence.

In some embodiments, homologous portions are at least 50, 100, 150, 200, 300, 400, 500, 600, 70, 800, 900, or 1000 base pairs in length. In some embodiments, the length is at least 50 base pairs. In some embodiments, the length is at least 100 base pairs. In some embodiments, the length is at least 150 base pairs. In some embodiments, the length is at least 200 base pairs. In some embodiments, the length is at least 300 base pairs. In some embodiments, the length is at least 400 base pairs. In some embodiments, the length is at least 500 base pairs.

In some embodiments, homologous portions encode amino acid residues that are of certain structural and/or functional units of encoded proteins. For example, in some embodiments, a homologous portion may encode a protein domain that is characteristic of the family of the encoded protein, that is enzymatically active, that is responsible for interactions with an effector, etc., as described in the present disclosure.

Methods for assessing similarity/homology of nucleic acid sequences are widely known in the art and can be used in accordance with the present disclosure.

In some embodiments, an ETaG and a nucleic acid sequence shares homology in their encoded products, e.g., proteins. In some embodiments, an ETaG and a nucleic acid sequence are homologous in that a product encoded by the ETaG or a portion thereof shares similarity with a product encoded by the nucleic acid sequence or a portion thereof. In some embodiments, an encoded product is a protein. In some embodiments, products encoded by an ETaG and a nucleic acid sequence share similarity across their full length. In some embodiments, products encoded by an ETaG and a nucleic acid sequence share similarity at certain portions.

In some embodiments, an ETaG and a nucleic acid are homologous in that a protein encoded by the ETaG or a portion thereof shares similarity with a protein encoded by the nucleic acid or a portion thereof. Proteins encoded by an ETaG and a nucleic acid sequence can share similarity either at the level of their full lengths or portions. In some embodiments, all amino acid residues in a homologous portion are consecutive. In some embodiments, amino acid residues in a homologous portion are not all consecutive.

In some embodiments, a portion of a protein is a protein domain. In some embodiments, the protein domain forms a structure that is characteristic of the protein family. In some embodiments, the protein domain performs a characteristic function. For example, in some embodiments, a protein domain has an enzymatic function. In some embodiments, such a function is shared by the protein encoded by the ETaG and the protein encoded by the homologous nucleic acid sequence, e.g., a human gene. In some embodiments, a characteristic function is non-enzymatic. In some embodiments, a characteristic function is interaction with other entities, e.g., small molecules, nucleic acids, proteins, etc.

In some embodiments, a portion of a protein is a set of amino acid residues, either consecutive or not consecutive, that are important for a function of a protein. In some embodiments, a function is an enzymatic activity. In some embodiments, a portion of a protein is a set of residues that are required for the activity. In some embodiments, a portion is a set of residues that interact with a substrate, an intermediate, a product, or a co-factor. In some embodiments, a portion is a set of residues that interact with a substrate. In some embodiments, a portion is a set of residues that interact with an intermediate. In some embodiments, a portion is a set of residues that interact with a product. In some embodiments, a portion is a set of residues that interact with a co-factor.

In some embodiments, a function is an interaction with another entity. In some embodiments, an entity is a small molecule. In some embodiments, an entity is a lipid. In some embodiments, an entity is a carbohydrate. In some embodiments, an entity is a nucleic acid. In some embodiments, an entity is a protein. In some embodiments, a portion is a set of amino acid residues that contact with an interacting agent. For example, FIG. 13 illustrates a portion (a set of amino acid) that interact with nucleotide for Ras proteins and their homologous ETaGs, and FIGS. 14-16 illustrates portions that involved in protein-protein interactions.

In some embodiments, interaction of an amino acid residue with an interacting entity can be assessed by hydrogen bonding, electrostatic forces, van der Waals forces, aromatic stacking, etc. In some embodiments, interaction can be assessed by the distance of an amino acid residue to an interacting entity (for example, 4 Å as used in certain cases).

In some embodiments, a similarity is that two structures have a Calpha backbone rmsd (root mean square deviation) within 1, 2, 3, 4, 5, 6, 7, 8, 9, 10, 15, 20, 30, 40, or 50 square angstroms and have the same overall fold or core domain. In some embodiments, a Calpha backbone rmsd is within In some embodiments, a portion of a protein is or comprises a structural element that is essential for protein effector recruitment. In some embodiments, such a portion can be selected based on structural and/or activity data of a protein encoded by a nucleic acid sequence that is homologous to an ETaG, for example, a human gene which encodes a protein that is homologous to an ETaG.

In some embodiments, a portion of a protein comprises at least 2-200, 2-100, 2-50, 2-40, 2-30, 2-20, 2-15, 2-10, 3-200, 3-100, 3-50, 3-40, 3-30, 3-20, 3-15, 3-10, 4-200, 4-100, 4-50, 4-40, 4-30, 4-20, 4-15, 4-10, 5-200, 5-100, 5-50, 5-40, 5-30, 5-20, 5-15, or 5-10 amino acid residues. In some embodiments, a portion of a protein comprises at least 2, 3, 4, 5, 6, 7, 8, 9, 10, 11, 12, 13, 14, 15, 20, 25, 30, 40, 50, 60, 70, 80, 90, 100, or 150 amino acid residues. In some embodiments, a portion comprises at least 2 amino acid residues. In some embodiments, a portion comprises at least 3 amino acid residues. In some embodiments, a portion comprises at least 4 amino acid residues. In some embodiments, a portion comprises at least 5 amino acid residues. In some embodiments, a portion comprises at least 6 amino acid residues. In some embodiments, a portion comprises at least 7 amino acid residues. In some embodiments, a portion comprises at least 8 amino acid residues. In some embodiments, a portion comprises at least 9 amino acid residues. In some embodiments, a portion comprises at least 10 amino acid residues. In some embodiments, a portion comprises at least 15 amino acid residues. In some embodiments, a portion comprises at least 20 amino acid residues. In some embodiments, a portion comprises at least 25 amino acid residues. In some embodiments, a portion comprises at least 30 amino acid residues.

Similarity of nucleic acid sequences and protein sequences can be assessed by a number of methods, including those known in the art, in accordance with the present disclosure. For example, MUSCLE for protein sequences. In some embodiments, similarity is measured based on exact identity, e.g., the same amino acid residues at given position. In some embodiments, similarity is measured based on one or more common properties, e.g., amino acid residues bearing one or more identical or similar properties (e.g., acidic, basic, aromatic, etc.).

In some embodiments, an ETaG is homologous to a nucleic acid sequence (e.g., an expressed human nucleic acid sequence) in that the similarity between the ETaG and the nucleic acid base sequences is no less than a level based on the nucleic acid sequences of the ETaG and the nucleic acid sequence, or portions thereof, or the proteins encoded by the ETaG and the nucleic acid sequences or portions thereof, as described herein. In some embodiments, an ETaG is homologous to a nucleic acid sequence in that the similarity between the ETaG and the nucleic acid sequences is no less than a level based on the nucleic acid base sequences of the ETaG and the nucleic acid sequence, or portions thereof. In some embodiments, an ETaG is homologous to a nucleic acid sequence in that the similarity between the ETaG and the nucleic acid sequences is no less than a level based on proteins encoded by the ETaG and the nucleic acid sequences or portions thereof. In some embodiments, a level is at least 10%-99%. In some embodiments, a level is at least 10%, 20%, 30%, 40%, 50%, 60%, 70%, 80%, 85%, 90%, 91%, 92%, 93%, 94%, 95%, 96%, 97%, 98%, or 99%. In some embodiments, a level is at least 10%. In some embodiments, a level is at least 20%. In some embodiments, a level is at least 30%. In some embodiments, a level is at least 40%. In some embodiments, a level is at least 50%. In some embodiments, a level is at least 60%. In some embodiments, a level is at least 70%. In some embodiments, a level is at least 80%. In some embodiments, a level is at least 90%. In some embodiments, a level is 100%. In some embodiments, a level is lower than 100%. In some embodiments, a level is no more than 90%, 91%, 92%, 93%, 94%, 95%, 96%, 97%, 98%, or 99%.

In some embodiments, an ETaG is homologous to a nucleic acid sequence in that a protein encoded by the ETaG or a portion thereof has a 3-dimensional structure that is similar to that of a protein encoded by the nucleic acid sequence. In some embodiments, similarity is assessed by Calpha backbone rmsd (root mean square deviation), e.g., within 1-100, e.g., 5, 10, 20, 30, 40, 50 square angstroms. In some embodiments, sequences share similarity have Calpha backbone rmsd no more than 10 square angstroms, and also have the same overall fold or core domain. In some embodiments, structural similarity is assessed by interactions with another entity, e.g., small molecules, nucleic acids, proteins, etc. In some embodiments, structural similarity is assessed by small molecule binding. In some embodiments, a protein encoded by an embedded target gene or a portion thereof has a 3-dimensional structure that is similar to a protein encoded by a nucleic acid sequence in that a small molecule binding to a protein encoded by an embedded target gene or a portion thereof also binds to a protein encoded by nucleic acid sequence or a portion thereof. In some embodiments, a binding has a Kd of no more than 1-100 (e.g., 1, 2, 3, 4, 5, 6, 7, 8, 9, 10, 20, 30, 40, 50, 60, 70, 80, 90, 100) M.

Co-Regulation

In some embodiments, an ETaG is co-regulated with at least one biosynthetic gene in a biosynthetic gene cluster that contains a biosynthetic gene a proximity zone relative to which contains the ETaG. In some embodiments, an ETaG is co-regulated with a biosynthetic gene cluster that contains a biosynthetic gene a proximity zone relative to which contains the ETaG. In some embodiments, an ETaG is co-regulated with a biosynthetic gene cluster in that expression of the ETaG, and/or production of a product encoded by the ETaG, e.g., a protein, is correlated with production of a biosynthetic product produced by the enzymes encoded by the biosynthetic gene cluster. In some embodiments, production of a product encoded by the ETaG, e.g., a protein overlaps timewise with production of a biosynthetic product by the enzymes encoded by the biosynthetic gene cluster. In some embodiments, an ETaG is co-regulated with the biosynthetic gene cluster in that expression of the ETaG is increased, or turned on, when a biosynthetic product produced by the enzymes encoded by the biosynthetic gene cluster is produced. In some embodiments, an ETaG is co-regulated with the biosynthetic gene cluster in that expression of the ETaG is increased, or turned on, when level of a biosynthetic product produced by the enzymes encoded by the biosynthetic gene cluster is produced is increased.

In some embodiments, an ETaG provides advantages to its hosting organism, e.g., fungi, when the biosynthetic product produced by the enzymes encoded by the co-regulated biosynthetic gene cluster is produced. For example, in some embodiments, a protein encoded by an ETaG contributes to transportation of the biosynthetic product out of the cells producing the product. In some embodiments, a protein encoded by an ETaG detoxifies the biosynthetic product so that the biosynthetic product does not harm the organism producing the biosynthetic product but impacts growth or survival of other organisms.

In some embodiments, the present disclosure provides various methods for identifying ETaGs. For example, in some embodiments, a set of homologous biosynthetic gene clusters, e.g., biosynthetic gene clusters whose encoded enzymes produce the same biosynthetic products (based on prediction (e.g., sequence based prediction) and/or identification of the products), typically from different fungi strains, are compared. Non-biosynthetic genes present in only one or a few biosynthetic gene clusters (within the biosynthetic gene cluster or within the proximity zones relative to biosynthetic genes of the biosynthetic gene clusters) but are absent from the majority of biosynthetic gene clusters in the set are identified as ETaG candidates and are optionally further compared with mammalian, e.g., human, nucleic acid sequences to identify the homologous mammalian nucleic acid sequences. In some embodiments, such a method can be used to identify ETaGs on genomic scales, e.g., from sequences of many (e.g., hundreds, thousands, or even more) genomes as illustrated in the Examples. Identified ETaGs can be prioritized based on therapeutic importance of their mammalian homologs, particularly human homologs. In some embodiments, as illustrated in the Figures, an organism comprising an ETaG comprises one or more homologous genes of the ETaG.

In some embodiments, an ETaG is present at no more than 1%, 5%, or 10% of biosynthetic gene clusters of a set. In some embodiments, an ETaG is present at no more than 1%, 5%, or 10% of homologous biosynthetic gene clusters of a set. In some embodiments, an ETaG is present at no more than 1%, 5%, or 10% of biosynthetic gene clusters of a set, which biosynthetic gene clusters encode enzymes that produce the same biosynthetic product. In some embodiments, the percentage is less than 1%. In some embodiments, the percentage is less than 5%. In some embodiments, the percentage is less than 10%.

In some embodiments, the present disclosure provides methods that are particularly effective and efficient for identifying homologous ETaGs for human nucleic acid encoding targets of therapeutic interest by querying provided sets of nucleic acid sequences comprising biosynthetic gene clusters and/or ETaGs within proximity zones relative to biosynthetic genes of the biosynthetic gene clusters.

In some embodiments, the present disclosure provides sets of nucleic acid sequences as described herein. In some embodiments, the present disclosure provides a set of nucleic acid sequences, each of which is found in a fungal stain and comprises a biosynthetic gene cluster. In some embodiments, the present disclosure provides a set of nucleic acid sequences, each of which is found in a fungal stain and comprises an ETaG. In some embodiments, the present disclosure provides a set of nucleic acid sequences, each of which is found in a fungal stain and comprises a biosynthetic gene cluster and an ETaG that is within a proximity zone relative to a biosynthetic gene of the biosynthetic gene cluster. In some embodiments, nucleic acid sequences comprising biosynthetic gene clusters include no more sequences beyond the proximity zones relative to biosynthetic genes of the biosynthetic gene clusters and the sequences of the biosynthetic gene clusters. In some embodiments, the present disclosure provides database comprising provided sets of nucleic acid sequences.

In some embodiments, biosynthetic gene clusters of provided technologies comprise biosynthetic genes encoding enzymes that can participate in synthesis of compounds sharing at least one common chemical attribute. In some embodiments, a common chemical attribute is a cyclic core structure. In some embodiments, a common chemical attribute is a macrocyclic core structure. In some embodiments, a common chemical attribute is a shared acyclic backbone. In some embodiments, a common chemical attribute is that the compounds all belong to a certain category, e.g., non-ribosomal peptides (NPRS), terpenes, isoprenes, alkaloids, etc. In some embodiments, by identifying individual ETaGs for biosynthetic gene clusters, the present disclosure can differentiate compounds sharing common chemical attributes, even though they may be structurally similar.

Provided sets can be of various size and/or diversity. In some embodiments, it is desirable to have more sequences from more species to increase the number of ETaGs and biosynthetic gene clusters. In some embodiments, a set comprises at least 100, 200, 300, 400, 500, 1,000, 1,500, 2,000, 3,000, 5,000, 10,000, 20,000, 50,000, 100,000, 500,000, 1,000,000, 1,500,000 or 2,000,000 nucleic acid sequences comprising biosynthetic gene clusters. In some embodiments, a set comprises at least 100, 200, 300, 400, 500, 1,000, 1,500, 2,000, 3,000, 5,000, 10,000, 50,000, 100,000, 500,000, 1,000,000, 1,500,000 or 2,000,000 biosynthetic gene clusters. In some embodiments, a set comprises at least 100, 200, 300, 400, 500, 1,000, 1,500, 2,000, 3,000, 5,000, 10,000, 50,000, 100,000, 500,000, 1,000,000, 1,500,000 or 2,000,000 biosynthetic gene clusters related to ETaGs (biosynthetic gene clusters containing biosynthetic genes proximity zones relative to which contain ETaGs). In some embodiments, a set comprises at least 100, 200, 300, 400, 500, 1,000, 1,500, 2,000, 3,000, 5,000, 10,000, 50,000, 100,000, 500,000, 1,000,000, 1,500,000 or 2,000,000 ETaGs. In some embodiments, sequences of a provided set are from at least 100, 200, 300, 400, 500, 1,000, 1,500, 2,000, 3,000, 5,000, 10,000, 20,000, 50,000, 100,000 genomes from different species, e.g., different fungi species.

Among other things, provided databases and/or provided sets are so structured to particularly improve efficiencies for, e.g., identifying ETaGs, identifying ETaGs related to given biosynthetic gene clusters, identifying biosynthetic gene clusters related to given ETaGs, identifying ETaGs homologous to given mammalian nucleic acid sequences (e.g., human genes), identifying biosynthetic gene clusters related to given mammalian nucleic acid sequences (e.g., human genes; optionally through related ETaGs), identifying mammalian nucleic acid sequences (e.g., human genes) homologous to given ETaGs, human genes) homologous to given biosynthetic gene clusters (optionally through related ETaGs), identifying mammalian nucleic acid sequences (e.g., human genes) related to given products (and/or analogs thereof) produced by the enzymes encoded by biosynthetic gene clusters (optionally through related ETaGs and biosynthetic gene clusters), identifying products (and/or analogs thereof) produced by the enzymes encoded by biosynthetic gene clusters related to given mammalian nucleic acid sequences (e.g., human genes; optionally through related biosynthetic gene clusters and ETaGs), etc.

Figure 17:
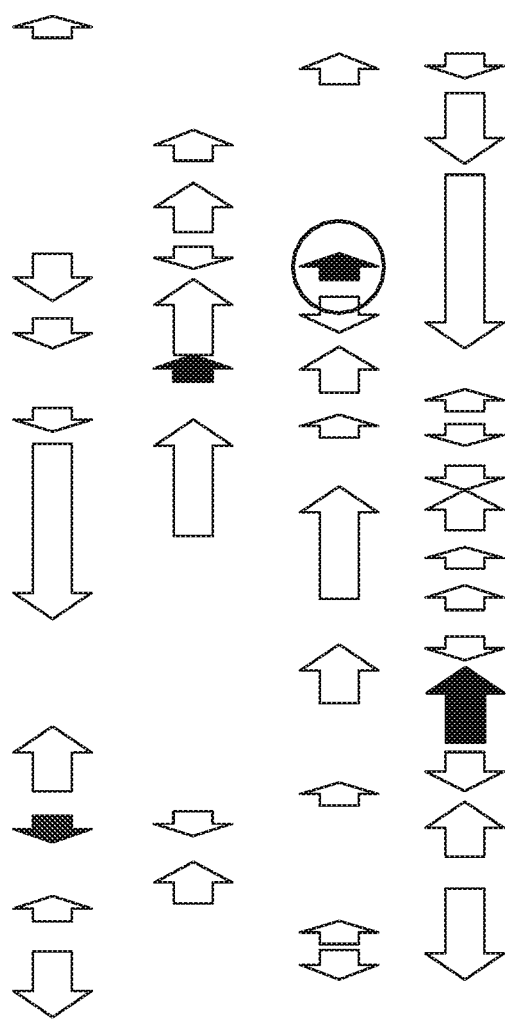
FIG. 17 depicts example sequences wherein ETaGs are indexed/marked (dark color).

For example, in some embodiments, ETaGs in provided sets and/or databases are indexed/marked for searching. For example, FIG. 17 (Applicant notes that provided sets and databases can contain hundreds, thousands or millions of sequences) depicts example sequences from provided sets and/or database wherein ETaGs are specifically indexed/marked (dark color). Among other things, such structural features can greatly improve, for example, query efficiency: instead of searching tens, hundreds, or thousands of genomes for ETaGs homologous to human gene of interests, one can instead using provided technologies to focus searches on indexed/marked ETaGs (for example, skipping non-biosynthetic gene cluster sequences and/or non-ETaG sequences (e.g., empty arrows and sequences in between in FIG. 17)) to quickly locate a hit (for example, the circled ETaG in FIG. 17), thereby saving time and resources for searching a vast majority of unrelated genomic information.

Additionally and alternatively, provided sets of sequences and databases are structured such that ETaGs can be independently annotated with information such as their related biosynthetic gene clusters (a related biosynthetic gene cluster of an ETaG is a biosynthetic gene cluster that contains a biosynthetic gene a proximity zone relative to which the ETaG is in), products produced by the enzymes encoded by the related biosynthetic gene clusters and analogs thereof, their homologous mammalian nucleic acid sequences (e.g., human genes), etc. Similarly, biosynthetic gene clusters can be independently annotated with information such as their related ETaGs (a related ETaG of a biosynthetic gene cluster is an etg within a proximity zone relative to a biosynthetic gene of the biosynthetic gene cluster), biosynthetic products produced by the enzymes encoded by the biosynthetic gene clusters and analogs thereof, homologous mammalian nucleic acid sequences of their related ETaGs and products encoded thereby, etc. By structuring sequence data with indexes and annotations, provided sets and databases can provide a number of advantages. For example, in some embodiments, provided systems provide fast access to ETaGs with useful related information, for example, their related biosynthetic gene clusters and human homologs, and vice versa, while maintaining data size and query cost low.

In some embodiments, at least 10, 20, 50, 100, 200, 500, 1,000, 2,000, 2,500, 5,000, or 10,000, or at least 5%, 10%, 20%, 30%, 40%, 50%, 60%, 70%, 80%, 90%, or 95%, or all, of ETaGs of a set are independently annotated. In some embodiments, at least 10, 20, 50, 100, 200, 500, 1,000, 2,000, 2,500, 5,000, or 10,000, or at least 5%, 10%, 20%, 30%, 40%, 50%, 60%, 70%, 80%, 90%, or 95%, or all, of ETaGs of a set are independently annotated with their related biosynthetic gene clusters and homologous mammalian nucleic acid sequences. In some embodiments, at least 10, 20, 50, 100, 200, 500, 1,000, 2,000, 2,500, 5,000, or 10,000, or at least 5%, 10%, 20%, 30%, 40%, 50%, 60%, 70%, 80%, 90%, or 95%, or all, of biosynthetic gene clusters of a set are independently annotated. In some embodiments, at least 10, 20, 50, 100, 200, 500, 1,000, 2,000, 2,500, 5,000, or 10,000, or at least 5%, 10%, 20%, 30%, 40%, 50%, 60%, 70%, 80%, 90%, or 95%, or all, of biosynthetic gene clusters of a set are independently annotated with their related ETaGs.

In some embodiments, provided sets of sequences and/or databases are embodied in a computer readable medium. In some embodiments, the present disclosure provides systems comprising one or more non-transitory machine-readable storage media storing data representing provided sets of sequences and/or databases. Non-transitory machine-readable storage media suitable for embodying provided data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks. Among other things, provided systems can be particularly efficient due to provided sets and databases having particular structures described herein.

In some embodiments, the present disclosure provides computer systems that can perform provided technologies. In some embodiments, the present disclosure provides computer systems adapted to perform provided methods. In some embodiments, the present disclosure provides computer systems adapted to query provided sets of sequences. In some embodiments, the present disclosure provides computer systems adapted to query provided databases. In some embodiments, the present disclosure provides computer systems adapted to access provided databases.

Computer systems that may be used to implement all or part of provided technologies may include various forms of digital computers. Examples of digital computers include, but are not limited to, laptops, desktops, workstations, personal digital assistants, servers, blade servers, mainframes, smart televisions and other appropriate computers. Mobile devices may be used to implement all or part of provided technologies. Mobile devices include, but are not limited to, tablet computing devices, personal digital assistants, cellular telephones, smartphones, digital cameras, digital glasses and other portable computing devices. The computing devices described herein, their connections and relationships, and their functions, are meant to be examples only, and are not meant to limit implementations of the technology.

All or part of technologies described herein and their various modifications can be implemented, at least in part, via a computer program product, e.g., a computer program tangibly embodied in one or more information carriers, e.g., in one or more tangible machine-readable storage media, for execution by, or to control the operation of, data processing apparatus, e.g., a programmable processor, a computer, or multiple computers.

A computer program for provided technologies can be written in any form of programming language, including compiled or interpreted languages, and it can be deployed in any form, including as a stand-alone program or as a module, part, subroutine, or other unit suitable for use in a computing environment. A computer program can be deployed to be executed on one computer or on multiple computers at one site or distributed across multiple sites and interconnected by a network.

Actions, e.g., associated with implementing programs and technologies, can be performed by one or more programmable processors executing one or more computer programs to perform provided technologies. All or part of the processes can be implemented as, special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks. Non-transitory machine-readable storage media suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

Each computing device, such as a tablet computer, may include a hard drive for storing data and computer programs, and a processing device (e.g., a microprocessor) and memory (e.g., RAM) for executing computer programs. Each computing device may include an image capture device, such as a still camera or video camera. The image capture device may be built-in or simply accessible to the computing device.

Each computing device may include a graphics system, including a display screen. A display screen, such as an LCD or a CRT (Cathode Ray Tube) displays, to a user, images that are generated by the graphics system of the computing device. As is well known, display on a computer display (e.g., a monitor) physically transforms the computer display. For example, if the computer display is LCD-based, the orientation of liquid crystals can be changed by the application of biasing voltages in a physical transformation that is visually apparent to the user. As another example, if the computer display is a CRT, the state of a fluorescent screen can be changed by the impact of electrons in a physical transformation that is also visually apparent. Each display screen may be touch-sensitive, allowing a user to enter information onto the display screen via a virtual keyboard. On some computing devices, such as a desktop or smartphone, a physical QWERTY keyboard and scroll wheel may be provided for entering information onto the display screen. Each computing device, and computer programs executed thereon, may also be configured to accept voice commands, and to perform functions in response to such commands.

Among other things, provided technologies (methods, sets, databases, systems, etc.) establish connections among biosynthetic gene clusters, products produced by the enzymes encoded by the biosynthetic gene clusters, ETaGs, homologous mammalian nucleic acid sequences, e.g., human genes, of ETaGs, etc. Provided technologies can thus, in some embodiments, be particularly powerful for identifying and/or characterizing human targets of products produced by the enzymes encoded by the biosynthetic gene clusters. Provided technologies can also be particularly powerful for identifying and developing modulators for human targets. For example, in some embodiments, to develop therapeutics for a human target, an ETaG of the human target (or nucleic acid sequences encoding the human target) can be quickly identified using provided technologies, together with information of its related biosynthetic gene clusters and/or biosynthetic products produced by the enzymes of the biosynthetic gene cluster. Products of the related biosynthetic gene cluster can be further characterized and if necessary, analogs thereof can be prepared, characterized, and assayed to develop therapeutics with improved properties. Provided technologies can be particularly useful for human targets that are challenging to target, and/or considered undruggable prior to the present disclosure.

In some embodiments, the present disclosure provides methods for assessing compounds using identified ETaGs and products encoded thereby. In some embodiments, the present disclosure provides a method comprising:

contacting at least one test compound with a gene product encoded by an embedded target gene of a fungal nucleic acid sequence, which embedded target gene is characterized in that it:
is not required for or is not involved in the biosynthesis of the product of the biosynthetic gene cluster;
is within a proximity zone relative to at least one biosynthetic gene in the cluster;
is homologous to an mammalian nucleic acid sequence; and
is optionally co-regulated with at least one biosynthetic gene in the cluster; and determining that:
level or activity of the gene product is altered when the test compound is present as compared with when it is absent; or
level or activity of the gene product is comparable to that observed when a reference agent having a known effect on the level or activity is present.

In some embodiments, the present disclosure provides methods for identifying and/or characterizing a mammalian, e.g., human, target of a product produced by enzymes encoded by a biosynthetic gene cluster, or an analog of the product, comprising:
identifying a human homolog of an ETaG that is within a proximity zone relative to at least one biosynthetic gene of the biosynthetic gene cluster, or is within a proximity zone relative to at least one biosynthetic gene of a second biosynthetic gene cluster which second biosynthetic gene cluster encodes enzymes that produce the same biosynthetic product that is produced by enzymes encoded by the biosynthetic gene cluster; and
optionally assaying an effect of the product produced by enzymes encoded by a biosynthetic gene cluster, or an analog of the product, on the target.

In some embodiments, the present disclosure provides methods for assessing compounds using products encoded by mammalian, e.g., human, nucleic acid sequences that are homologous to ETaGs. In some embodiments, the present disclosure provides a method comprising:

contacting at least one test compound with a gene product encoded by a mammalian nucleic acid sequence, which is homologous to an embedded target gene characterized in that the embedded target gene:
is not required for or is not involved in the biosynthesis of the product of the biosynthetic gene cluster;
is within a proximity zone relative to at least one biosynthetic gene in the cluster;
is homologous to the mammalian nucleic acid sequence; and
is optionally co-regulated with at least one biosynthetic gene in the cluster; and determining that:
level or activity of the gene product is altered when the test compound is present as compared with when it is absent; or
level or activity of the gene product is comparable to that observed when a reference agent having a known effect on the level or activity is present.

In some embodiments, the present disclosure provides methods for identifying and/or characterizing a mammalian, e.g., human, target of a product produced by enzymes encoded by a biosynthetic gene cluster, or an analog of the product, comprising: identifying a human homolog of an ETaG that is within a proximity zone relative to at least one biosynthetic gene of the biosynthetic gene cluster; and optionally assaying an effect of the product produced by enzymes encoded by a biosynthetic gene cluster, or an analog of the product, on the target.

In some embodiments, provided methods and systems are useful for assessing interactions of human targets with compounds. In some embodiments, the present disclosure provides methods for accessing interaction of a human target with a compound, comprising:
comparing nucleic acid sequence of the human target, or the nucleic acid sequence that encodes the human target, with a set of nucleic acid sequences which comprise one or more ETaGs.

In some embodiments, a compound produced by the enzymes of a biosynthetic gene cluster interacts with a target encoded by a mammalian, e.g., human, nucleic sequence that is homologous to an ETaG related to the biosynthetic gene cluster.

In some embodiments, provided technologies are particularly useful for designing and/or providing modulators for human targets, as, among other things, provided technologies provide connections among biosynthetic gene clusters, ETaGs, and human target genes.

In some embodiments, the present disclosure provides methods for identifying and/or characterizing a modulator of a human target, comprising:

providing a product or an analog thereof, which product is produced by the enzymes encoded by a biosynthetic gene cluster, wherein, within a proximity zone relative to at least one biosynthetic gene in the biosynthetic gene cluster, exists an ETaG that:

is homologous to the human target, or a nucleic acid sequence that encodes the human target; and is optionally co-regulated with at least one biosynthetic gene in the cluster.

In some embodiments, a human target is a Ras protein. In some embodiments, a Ras protein is a HRas protein. In some embodiments, a Ras protein is a KRas protein. In some embodiments, a Ras protein is a NRas protein. In some embodiments, a human target is a protein comprising a RasGEF domain. In some embodiments, a protein is KNDC1, PLCE1, RALGDS, RALGPS1, RALGPS2, RAPGEF1, RAPGEF2, RAPGEF3, RAPGEF4, RAPGEF5, RAPGEF6, RAPGEFL1, RASGEF1A, RASGEF1B, RASGEF1C, RASGRF1, RASGRF2, RASGRP1, RASGRP2, RASGRP3, RASGRP4, RGL1, RGL2, RGL3, RGL4/RGR, SOS1, SOS2, or human guanine nucleotide exchange factor. In some embodiments, a protein is SOS1. In some embodiments, a protein is human guanine nucleotide exchange factor. In some embodiments, a human target is a protein comprising a RasGAP domain. In some embodiments, a protein is DAB2IP, GAPVD1, IQGAP1, IQGAP2, IQGAP3, NF1, RASA1, RASA2, RASA3, RASA4, RASAL1, RASAL2, or SYNGAP1. In some embodiments, a protein is protein p120. In some embodiments, a protein is human guanine nucleotide activating factor.

In some embodiments, the present disclosure provides a method for identifying and/or characterizing a modulator for a human Ras protein, comprising:

preparing an analog of a compound produced by the enzymes encoded by a biosynthetic gene cluster;

wherein, within a proximity zone relative to at least one biosynthetic gene in the biosynthetic gene cluster, exists an ETaG that:

is homologous to the human Ras protein, a RasGEF domain, or a RasGAP domain, or a nucleic acid sequence that encodes the human Ras protein, a RasGEF domain, or a RasGAP domain; and is optionally co-regulated with at least one biosynthetic gene in the cluster.

In some embodiments, a protein comprising the RasGEF domain modulates one or more functions of the human Ras protein. In some embodiments, a protein comprising the RasGAP domain modulates one or more functions of the human Ras protein.

In some embodiments, the present disclosure provides a method for identifying and/or characterizing a modulator for a human Ras protein, comprising:

preparing an analog of a compound produced by the enzymes encoded by a biosynthetic gene cluster;

wherein, within a proximity zone relative to at least one biosynthetic gene in the biosynthetic gene cluster, exists an ETaG that:

is homologous to the human Ras protein, or a nucleic acid sequence that encodes the human Ras protein; and is optionally co-regulated with at least one biosynthetic gene in the cluster.

In some embodiments, the present disclosure provides a method for identifying and/or characterizing a modulator for a protein comprising a RasGEF domain, comprising:

preparing an analog of a compound produced by the enzymes encoded by a biosynthetic gene cluster;

wherein, within a proximity zone relative to at least one biosynthetic gene in the biosynthetic gene cluster, exists an ETaG that:

is homologous to the RasGEF domain, or a nucleic acid sequence that encodes the RasGEF domain; and is optionally co-regulated with at least one biosynthetic gene in the cluster.

In some embodiments, the present disclosure provides a method for identifying and/or characterizing a modulator for a protein comprising a RasGAP domain, comprising:

preparing an analog of a compound produced by the enzymes encoded by a biosynthetic gene cluster;

wherein, within a proximity zone relative to at least one biosynthetic gene in the biosynthetic gene cluster, exists an ETaG that:

is homologous to the RasGAP domain, or a nucleic acid sequence that encodes the RasGAP domain; and is optionally co-regulated with at least one biosynthetic gene in the cluster.

In some embodiments, a biosynthetic gene cluster is an example biosynthetic gene cluster, or a biosynthetic gene cluster comprising one or more biosynthetic genes, illustrated in one of the Figures together with an ETaG homologous to a Ras protein, e.g., FIGS. 5-12, and 20-27. In some embodiments, a biosynthetic gene cluster is an example biosynthetic gene cluster illustrated in one of the Figures together with an ETaG homologous to a Ras protein, e.g., FIGS. 5-12, and 20-27. In some embodiments, a biosynthetic gene cluster is an example biosynthetic gene cluster, or a biosynthetic gene cluster comprising one or more biosynthetic genes, illustrated in one of the Figures together with an ETaG homologous to a RasGEF domain, e.g., FIGS. 28-33, and 35. In some embodiments, a biosynthetic gene cluster is an example biosynthetic gene cluster illustrated in one of the Figures together with an ETaG homologous to a RasGEF domain, e.g., FIGS. 28-33, and 35. In some embodiments, a biosynthetic gene cluster is an example biosynthetic gene cluster, or a biosynthetic gene cluster comprising one or more biosynthetic genes, illustrated in one of the Figures together with an ETaG homologous to a RasGEF domain, e.g., FIGS. 34, and 36-39. In some embodiments, a biosynthetic gene cluster is an example biosynthetic gene cluster illustrated in one of the Figures together with an ETaG homologous to a RasGEF domain, e.g., FIGS. 34, and 36-39. Example ETaG sequences are presented in the present disclosure, and, among other things, can be utilized to locate and identify biosynthetic gene clusters, biosynthetic genes, etc.

In some embodiments, the present disclosure provides methods for modulating a human target, comprising:

providing a product or an analog thereof, which product is produced by the enzymes encoded by a biosynthetic gene cluster, wherein, within a proximity zone relative to at least one biosynthetic gene in the biosynthetic gene cluster, exists an ETaG that:

is homologous to the human target, or a nucleic acid sequence that encodes the human target; and is optionally co-regulated with at least one biosynthetic gene in the cluster.

In some embodiments, the present disclosure provides methods for modulating a Ras protein, comprising:

providing a product or an analog thereof, which product is produced by the enzymes encoded by a biosynthetic gene cluster of one of FIGS. 5-12, and 20-27.

In some embodiments, the present disclosure provides methods for modulating a RasGEF protein, comprising:

providing a product or an analog thereof, which product is produced by the enzymes encoded by a biosynthetic gene cluster of one of FIGS. 28-33, and 35.

In some embodiments, the present disclosure provides methods for modulating a RasGAP protein, comprising:

providing a product or an analog thereof, which product is produced by the enzymes encoded by a biosynthetic gene cluster of one of FIGS. 34, and 36-39.

In some embodiments, an ETaG is identified by a provided method.

In some embodiments, a product is produced by enzymes encoded by a biosynthetic gene cluster is a secondary metabolite produced by the biosynthetic gene cluster.

In some embodiments, an analog of a product comprises the structural core of a product. In some embodiments, a product is cyclic, e.g., monocyclic, bicyclic, or polycyclic. In some embodiments, the structural core of the product is or comprises the monocyclic, bicyclic, or polycyclic ring system. In some embodiments, the structural core of the product comprises one ring of the bicyclic or polycyclic ring system of the product.

In some embodiments, a product is linear, and the structural core is its backbone. In some embodiments, a product is or comprises a polypeptide, and a structural core is the backbone of the polypeptide. In some embodiments, a product is or comprises a polyketide, and a structural core is the backbone of the polyketide.

In some embodiments, an analog is the product substituted with one or more suitable substituents as described herein. In some embodiments, an analog is the structural core substituted with one or more suitable substituents as described herein.

Among other things, the present disclosure provides the following Example Embodiments:

1. A method comprising steps of:

querying a set of nucleic acid sequences, each of which is found in a fungal strain and comprises a biosynthetic gene cluster; and identifying within at least one of the fungal nucleic acid sequences an embedded target gene (ETaG) sequence characterized in that it:

is not required for or is not involved in the biosynthesis of the product of the biosynthetic gene cluster;

is within a proximity zone relative to at least one gene in the cluster;

is homologous to an mammalian nucleic acid sequence; and is optionally co-regulated with at least one biosynthetic gene in the cluster.

2. The method of embodiment 1, wherein the ETaG sequence is within a proximity zone relative to at least one biosynthetic gene in the cluster.

3. The method of any one of the preceding embodiments, wherein a nucleic acid sequence comprising a biosynthetic gene cluster contains no more sequences beyond the nucleic acid sequences of the proximity zones relative to the biosynthetic genes of the biosynthetic gene cluster and the nucleic acid sequence of the biosynthetic gene cluster.

4. The method of any one of the preceding embodiments, wherein a proximity zone is no more than 1, 2, 3, 4, 5, 6, 7, 8, 9, 10, 20, 30, 40, 50, 60, 70, 80, 90, or 100 kb upstream or downstream of a biosynthetic gene in the cluster.

5. The method of any one of the preceding embodiments, wherein a proximity zone is no more than 50 kb upstream or downstream of a biosynthetic gene in the cluster.

6. The method of any one of the preceding embodiments, wherein a proximity zone is no more than 40 kb upstream or downstream of a biosynthetic gene in the cluster.

7. The method of any one of the preceding embodiments, wherein a proximity zone is no more than 30 kb upstream or downstream of a biosynthetic gene in the cluster.

8. The method of any one of the preceding embodiments, wherein a proximity zone is no more than 20 kb upstream or downstream of a biosynthetic gene in the cluster.

9. The method of any one of the preceding embodiments, wherein a proximity zone is no more than 10 kb upstream or downstream of a biosynthetic gene in the cluster.

10. The method of any one of the preceding embodiments, wherein a proximity zone is a region between two biosynthetic genes of a biosynthetic gene cluster.

11. The method of any one of the preceding embodiments, wherein the mammalian nucleic acid sequence is an expressed sequence.

12. The method of any one of the preceding embodiments, wherein the mammalian nucleic acid sequence is a gene.

13. The method of any one of the preceding embodiments, wherein the mammalian nucleic acid sequence is a human nucleic acid sequence.

14. The method of any one of the preceding embodiments, wherein an embedded target gene sequence is homologous to an expressed mammalian nucleic acid sequence in that its base sequence or a portion thereof is at least 50%, 60%, 70%, 80%, or 90% identical to that of an mammalian nucleic acid sequence.

15. The method of embodiment 14, wherein the sequence or a portion thereof is at least 50, 100, 150, or 200 base pairs in length.

16. The method of any one of embodiments 1-13, wherein an embedded target gene sequence is homologous to an expressed mammalian nucleic acid sequence in that a product encoded by an embedded target gene or a portion thereof is homologous to that of a mammalian nucleic acid sequence or a portion thereof.

17. The method of embodiment 16, wherein the product is a protein.

18. The method of embodiment 16, wherein the protein encoded by an embedded target gene or a portion thereof is at least 50%, 60%, 70%, 80%, or 90% similarity to that encoded by a mammalian nucleic acid sequence or a portion thereof.

19. The method of embodiment 16, wherein the protein encoded by an embedded target gene or a portion thereof has a 3-dimensional structure that is similar to that of a protein encoded by a mammalian nucleic acid sequence or a portion thereof.

20. The method of embodiment 19, wherein the portion of a protein encoded by an embedded target gene has a 3-dimensional structure that is similar to that of a protein encoded by a mammalian nucleic acid sequence.

21. The method of any one of embodiments 19-20, wherein the similarity is that the structures have a Calpha backbone rmsd (root mean square deviation) within 10 square angstroms and have the same overall fold or core domain.

22. The method of any one of embodiments 19-20, wherein a protein encoded by an embedded target gene or a portion thereof has a 3-dimensional structure that is similar to a protein encoded by a mammalian nucleic acid sequence in that a small molecule binding to a protein encoded by an embedded target gene or a portion thereof also binds to a protein encoded by mammalian nucleic acid sequence or a portion thereof.
23. The method of embodiment 22, wherein the binding of the small molecule to the proteins encoded by the embedded target gene and the mammalian nucleic acid sequence or portions thereof has a Kd no more 100 µM, 50 µM, 10 µM, 5 µM or 1 µM.
24. The method of any one of embodiments 22-23, wherein the small molecule is produced by a fungi.
25. The method of embodiment 24, wherein the small molecule is acyclic.
26. The method of embodiment 24, wherein the small molecule is cyclic.
27. The method of any one of embodiments 24-26, wherein the small molecule is a secondary metabolite molecule produced by a fungi.
28. The method of any one of embodiments 24-27, wherein the small molecule is non-ribosomally synthesized.
29. The method of any one of embodiments 24-28, wherein the small molecule is a biosynthetic product a biosynthetic gene cluster.
30. The method of embodiment 16, wherein a portion of the protein encoded by an embedded target gene is at least 50%, 60%, 70%, 80%, or 90% similarity to a portion of the protein encoded by an expressed mammalian nucleic acid sequence.
31. The method of embodiment 30, wherein the portion of the protein is a protein domain.
32. The method of any one of embodiments 30-31, wherein the portion of the protein is a set of amino acid residues necessary for a function.
33. The method of embodiment 32, wherein the function is an enzymatic function.
34. The method of embodiment 33, wherein the set of amino acid residues contact a substrate.
35. The method of embodiment 33, wherein the set of amino acid residues contact an intermediate.
36. The method of embodiment 33, wherein the set of amino acid residues contact a product.
37. The method of embodiment 32, wherein the function is an interaction with another entity.
38. The method of embodiment 37, wherein the entity is a small molecule.
39. The method of embodiment 37, wherein the entity is a lipid.
40. The method of embodiment 37, wherein the entity is a carbohydrate.
41. The method of embodiment 37, wherein the entity is a nucleic acid.
42. The method of embodiment 37, wherein the entity is a protein.
43. The method of any one of embodiments 32-42, wherein each of the residues of the set is within 4 Å of the entity.
44. The method of any one of the preceding embodiments, wherein the embedded target gene is co-regulated with at least one gene in the cluster.
45. The method of any one of the preceding embodiments, wherein the embedded target gene is absent from 80%, 90%, 95%, or 100% of all fungal nucleic acid sequences in the set that are from a different fungal strain and comprises a homologous or identical biosynthetic gene cluster.
46. The method of any one of the preceding embodiments, wherein the set comprises at least 100, 1,000, 5,000, 10,000, 50,000, 100,000, 500,000, 1,000,000, 1,500,000, 2,000,000 or 2,500,000 distinct fungi nucleic acid sequences.
47. The method of any one of the preceding embodiments, wherein the set comprises nucleic acid sequences from at least 100, 500, 1,000, 5,000, 10,000, 15,000, 20,000, 22,000, 25,000 or 30,000 distinct fungal strains.
48. The method of any one of the preceding embodiments, wherein the ETaG sequence is not a house-keeping gene.
49. The method of any one of the preceding embodiments, wherein the ETaG sequence is or comprises a sequence that is homologous to a second nucleic acid sequence or a portion thereof in the same genome.
50. The method of any one of the preceding embodiments, wherein the ETaG sequence is or comprises a sequence that encodes a product that is homologous to a product or a portion thereof encoded by a second nucleic acid sequence in the same genome.
51. The method of embodiment 49 or 50, wherein the homology is at least 50%, 60%, 70%, 75%, 80%, 85%, 90%, 91%, 92%, 93%, 94%, 95%, 96%, 97%, 98%, 99% or 99.5%.
52. The method of embodiment 49, wherein the homology is at least 70%.
53. The method of embodiment 49, wherein the homology is at least 80%.
54. The method of embodiment 49, wherein the homology is at least 90%.
55. The method of any one of embodiments 48-54, wherein the second nucleic acid sequence is or comprises a house-keeping gene.
56. The method of any one of embodiments 48-55, wherein the ETaG sequences encode a product that provides resistance to a product of the biosynthetic gene cluster while the second nucleic acid sequence does not.
57. The method of embodiment 56, wherein the ETaG sequences encode a protein that provides resistance to a small molecule product of the biosynthetic gene cluster while proteins encoded by the second nucleic acid sequence do not.
58. The method of any one of the preceding embodiments, wherein nucleic acid sequences within the set comprise biosynthetic gene clusters whose biosynthetic genes encode enzymes that participate in synthesis of compounds sharing at least one common chemical attribute.
59. The method of any one of the preceding embodiments, wherein the nucleic acid sequences are from multiple fungi strains.
60. The method of any one of the preceding embodiments, wherein the common chemical attribute is or comprises a cyclic system.
61. The method of any one of the preceding embodiments, wherein the common chemical attribute is or comprises a macrocycle.
62. The method of any one of embodiments 52-61, wherein the common chemical attribute is or comprises an acyclic backbone.
63. The method of any one of embodiments 52-62, wherein compounds sharing at least one common chemical attribute are polyketides.
64. The method of any one of embodiments 52-62, wherein compounds sharing at least one common chemical attribute are non-ribosomal peptides.
65. The method of any one of embodiments 52-62, wherein compounds sharing at least one common chemical attribute are alkaloids.

66. The method of any one of embodiments 52-62, wherein compounds sharing at least one common chemical attribute are terpenes/isoprenes.

67. A method comprising steps of:
contacting at least one test compound with a gene product encoded by an embedded target gene of a fungal nucleic acid sequence, which embedded target gene (ETaG) is characterized in that it:
is not required for or is not involved in the biosynthesis of the product of the biosynthetic gene cluster;
is within a proximity zone relative to at least one biosynthetic gene in the cluster;
is homologous to an mammalian nucleic acid sequence; and
is optionally co-regulated with at least one biosynthetic gene in the cluster; and determining that:
level or activity of the gene product is altered when the test compound is present as compared with when it is absent; or
level or activity of the gene product is comparable to that observed when a reference agent having a known effect on the level or activity is present.

68. The method of embodiment 67, wherein the ETaG is an ETaG as described in any one of embodiments 1-66.

69. The method of embodiment 67 or 68, wherein the mammalian nucleic acid sequence is a human Ras sequence.

70. The method of embodiment 69, wherein the mammalian nucleic acid sequence is a KRas, HRas, or NRas sequence.

71. The method of embodiment 67 or 68, wherein the mammalian nucleic acid sequence is a sequence encoding a RasGEF domain.

72. The method of embodiment 67 or 68, wherein the mammalian nucleic acid sequence is a sequence encoding a RasGAP domain.

73. The method of any one of embodiments 66-72, wherein the ETaG is an ETaG in one of FIGS. 1-39.

74. The method of any one of embodiments 66-73, wherein the biosynthetic gene cluster is a biosynthetic gene cluster in one of FIGS. 1-39.

75. The method of any one of embodiments 66-74, wherein the test compound is a biosynthetic product of the biosynthetic gene cluster or an analog thereof.

76. A method comprising steps of:
contacting at least one test compound with a gene product encoded by an expressed mammalian nucleic acid sequence, which sequence is the expressed mammalian nucleic acid sequence to which the embedded target gene sequence of any one of embodiments 1-75 is homologous.

77. The method of embodiment 76, wherein the mammalian nucleic acid sequence is a human Ras sequence.

78. The method of embodiment 77, wherein the mammalian nucleic acid sequence is a KRas, HRas, or NRas sequence.

79. The method of embodiment 76 or 77, wherein the mammalian nucleic acid sequence is a sequence encoding a RasGEF domain.

80. The method of embodiment 76 or 77, wherein the mammalian nucleic acid sequence is a sequence encoding a RasGAP domain.

81. The method of any one of embodiments 76-80, wherein the ETaG is an ETaG in one of FIGS. 1-39.

82. The method of any one of embodiments 76-81, wherein the biosynthetic gene cluster is a biosynthetic gene cluster in one of FIGS. 1-39.

83. The method of any one of embodiments 76-82, wherein the test compound is a biosynthetic product of the biosynthetic gene cluster or an analog thereof.

84. A method comprising:
identifying a human homolog of an ETaG that is within a proximity zone relative to at least one biosynthetic gene of the biosynthetic gene cluster; and
optionally assaying an effect of the product produced by enzymes encoded by a biosynthetic gene cluster, or an analog of the product, on the human homolog.

85. The method of embodiment 77, wherein the ETaG is an ETaG as described in any one of embodiments 1-66.

86. A method for identifying and/or characterizing a modulator of a human target, comprising:
providing a product or an analog thereof, which product is produced by the enzymes encoded by a biosynthetic gene cluster, wherein, within a proximity zone relative to at least one gene in the biosynthetic gene cluster, exists an ETaG that:
is homologous to the human target, or a nucleic acid sequence that encodes the human target; and
is optionally co-regulated with at least one biosynthetic gene in the cluster.

87. The method of embodiment 86, wherein the ETaG is an ETaG as described in any one of embodiments 1-83.

88. The method of embodiment 86, wherein the human target is a Ras protein.

89. The method of embodiment 88, wherein the human target is a KRas, HRas, or NRas.

90. The method of embodiment 86, wherein the human target comprises a RasGEF domain.

91. The method of embodiment 86, wherein the human target comprises a RasGAP domain.

92. The method of any one of embodiments 86-91, wherein the ETaG is an ETaG in one of FIGS. 1-39.

93. The method of any one of embodiments 86-92, wherein the biosynthetic gene cluster is a biosynthetic gene cluster in one of FIGS. 1-39.

94. A method for modulating a human target, comprising:
providing a product or an analog thereof, which product is produced by the enzymes encoded by a biosynthetic gene cluster, wherein, within a proximity zone relative to at least one biosynthetic gene in the biosynthetic gene cluster, exists an ETaG that:
is homologous to the human target, or a nucleic acid sequence that encodes the human target; and
is optionally co-regulated with at least one biosynthetic gene in the cluster.

95. The method of embodiment 94, wherein the human target is a Ras protein.

96. The method of embodiment 94, wherein the human target is a KRas, HRas, or NRas.

97. The method of embodiment 94, wherein the human target comprises a RasGEF domain.

98. The method of embodiment 94, wherein the human target comprises a RasGAP domain.

99. The method of any one of embodiments 94-98, wherein the ETaG is an ETaG in one of FIGS. 1-39.

100. The method of any one of embodiments 94-99, wherein the biosynthetic gene cluster is a biosynthetic gene cluster in one of FIGS. 1-39.

101. The method of embodiment 94, wherein the ETaG is an ETaG as described in any one of embodiments 1-93.

102. A database comprising:
a set of nucleic acid sequences, each of which is found in a fungal strain and comprises a biosynthetic gene cluster;
wherein the set of nucleic acid sequences are embodied in a computer readable medium.

103. The database of embodiment 102, wherein one or more embedded target genes of any one of embodiments 1-101 are indexed.

104. A system comprising:
one or more non-transitory machine-readable storage media storing data representing a set of nucleic acid sequences, each of which is found in a fungal strain and comprises a biosynthetic gene cluster.
105. A system comprising:
one or more non-transitory machine-readable storage media storing data representing a set of nucleic acid sequences, each of which is or comprises a ETaG sequence.
106. The system of embodiment 105, wherein one or more embedded target genes of any one of embodiments 1-101 are indexed.
107. A computer system, adapted to perform a method of any one of embodiments 1-101.
108. A computer system, adapted to access a database of any one of embodiments 95-103.

EXEMPLIFICATION

Non-limiting examples of provided technologies are described below.

Example 1. Construction of Example Databases and their Example Uses

Around 2,000 reported fungi genomes were processed to identify potential biosynthetic gene clusters, using, for example, antiSMASH, and approximately 70,000 identified biosynthetic gene clusters were added to a database. Human targets of interest were used to query the initial database. For example, protein sequence of human Sec7 was used to BLAST search against the initial library to identify ETaGs. Alternatively and additionally, the biosynthetic gene clusters can be compared among themselves. For example, in one process, non-biosynthetic genes present at one or some biosynthetic gene clusters (within a proximity zone relative to at least one biosynthetic gene of the biosynthetic gene clusters) but are absent from most other homologous biosynthetic gene clusters for the same biosynthetic product are identified as potential ETaGs, and are further confirmed by analyzing whether they have homologous mammalian nucleic acid sequences (e.g., human genes) at nucleic acid level and/or, preferably, protein level. Identified ETaGs can be indexed/marked and annotated. The database is searchable by either nucleotide sequence (e.g., BLASTN; tBLASTx) or protein sequence (e.g., tBLASTn).

Results from a BLAST query of a human target were, in some embodiments, listed in order of strength of sequence homology, indicating all putative hits within the database. DNA sequences of all hit biosynthetic gene clusters were then inspected to verify that one or more open reading frame (gene) homologs of the target protein was within the predicted confines of the biosynthetic gene clusters.

In some embodiments, GenBank-formatted sequence files (*.gbk) of each biosynthetic cluster were assembled and curated, from which the ETaG protein sequence was obtained through prediction algorithms, e.g., those comprising antiSMASH and/or methods. The protein families (pfam) function of open reading frames can be predicted by, e.g., antiSMASH, and the nucleotide distance between each identified ETaG and its nearest biosynthetic enzyme predicted by antisSMASH can be determined. In some embodiments, the closer a predicted ETaG is to a biosynthetic enzyme, the higher the likelihood that this open reading frame encodes a legitimate ETaG.

Applicant has successfully identified many biosynthetic gene clusters with related ETaGs beyond the several bona fide ETaG-containing biosynthetic gene clusters (biosynthetic gene clusters for cyclosporine, fellutamide, lovastatin, mycophenolic acid, and brefeldin).

In some embodiments, the present disclosure encompasses the recognition that an ETaG can serve as a functional homolog (an ortholog) of a putative human target protein. In some embodiments, protein sequences of putative ETaG hits were compared to the sequence of human target orthologs. For example, in a project to find ETaGs of human Protein A, n biosynthetic gene clusters were found containing a putative Protein A homolog, and all of the n predicted ETaG proteins were aligned with the human Protein A. In some embodiments, only amino acids within the specific catalytic or structural domain defining the pfam boundaries of the ETaG/target (e.g., based on predictive subfamily domain architecture) were used in an alignment analysis. The ETaG sequences were directly compared to their human counterparts by aligning all ETaGs and human target protein(s), with their phylogenetic relationships yielding quantitative correlative data (e.g. peptide sequence similarity and/or evolutionary tree visualization). Additional analysis can include conservation/similarity of essential structural elements of protein effector recruitment/binding, for example, based on the examination of the tertiary protein structure of the human target. For example, in some embodiments, aligned sequences were compared to the PDB crystal structure corresponding to the target protein residues within 4 Angstrom of the corresponding engaging proteins. Without the intention to be limited by any theory, in cases where these structural motifs are conserved within fungal ETaGs, it may indicate an increased probability that the metabolite produced by the ETaG-related biosynthetic gene cluster is an effector of both fungal and human target proteins, and the metabolite produced can be a drug candidate, or a lead for drug development, toward the human target. In some embodiments, the above analyses were used to prioritize ETaGs and their related biosynthetic gene clusters, and metabolites produced from the biosynthetic gene clusters, with respect to targeting human targets.

Example 2. Modulators for Human Targets—Sec7

Among other things, the present disclosure provides technologies for identifying modulators for human targets. In some embodiments, a human sequence is utilized to query a provided database to identify biosynthetic gene clusters in whose proximity zone exists a homolog of the human sequence.

For example, among other things, the present disclosure provides biosynthetic gene clusters whose biosynthetic products may modulate Sec7 functions. To identify modulators for human Sec7 domain, Sec7 protein sequence was used to query a database, e.g., the database provided in Example 1. An example Sec7-homologous ETaG was identified in *Penicillium vulpinum* IBT 29486 with a related biosynthetic gene cluster—the ETaG is in a proximity zone relative to one of the biosynthetic genes of the biosynthetic gene cluster. See FIG. 1, FIG. 18 and FIG. 19. Among other things, the identified biosynthetic gene cluster shares homology with the biosynthetic gene cluster for Brefeldin A in *Eupenicillium brefeldianum*, and was expected to produce Brefeldin A. Therefore, Brefeldin A was identified as a candidate modulator, and/or a lead compound for modulators, of Sec7. If desired, the result can be optionally validated by expressing the biosynthetic gene cluster of *Penicillium vulpinum* IBT 29486 and isolating and characterizing its product, and then assaying functions of the product against Sec7 using a number of methods available in the art in accordance with the present disclosure. As it has been reported that Brefeldin A targets Sec7 domain of human GBF1, this example illustrates that provided technologies can be successfully utilized to identify modulators of human targets.

Example 3. ETaGs of Lovastatin, Fellutamide, and Cyclosporine

Provided technologies can be utilized to identify ETaGs for various entities. For example, as demonstrated herein, provided technologies can be used efficiently to identify EtaGs related to Lovastatin, Fellutamide, and Cyclosporine. Example results were presented in FIGS. 2-4.

Example 4. Modulators for Human Targets—Ras

Among other things, the present disclosure provides biosynthetic gene clusters whose biosynthetic products may modulate one or more functions of Ras proteins, and/or proteins that comprise RasGEFdomain (e.g., KNDC1, PLCE1, RALGDS, RALGPS1, RALGPS2, RAPGEF1, RAPGEF2, RAPGEF3, RAPGEF4, RAPGEF5, RAPGEF6, RAPGEFL1, RASGEF1A, RASGEF1B, RASGEF1C, RASGRF1, RASGRF2, RASGRP1, RASGRP2, RASGRP3, RASGRP4, RGL1, RGL2, RGL3, RGL4/RGR, SOS1, SOS2, etc.) and/or RasGAP domain (DAB2IP, GAPVD1, IQGAP1, IQGAP2, IQGAP3, NF1, RASA1, RASA2, RASA3, RASA4, RASAL1, RASAL2, SYNGAP1; etc.). Ras proteins, e.g., HRas, KRas, and NRas, are connected to many human cancers but are notoriously difficult targets for drug discovery. Among other things, the present disclosure provides technologies for developing Ras modulators, including Ras inhibitors.

Human Ras sequences were used to query provided databases, e.g., the database of Example 1. 8 example ETaGs were identified from different strains with various levels of sequence similarity to the human Ras proteins. The related biosynthetic gene clusters encode enzymes to produce different types of compounds. See FIGS. 5-12 and FIGS. 20-27. Identified ETaGs encoding proteins can be highly homologous to human Ras proteins. For example, see FIG. 13 for similarity of nucleotide binding residues, FIG. 14 for BRAF interacting residues, FIG. 15 for rasGAP interacting residues, and FIG. 16 for SOS interacting residues.

Similarly, biosynthetic gene clusters whose biosynthetic products may modulate RasGEF and RasGAP domains are identified. As demonstrated herein, example identified biosynthetic gene clusters can contain genes and/or modules that involve in synthesis of various types of moieties/products, e.g., terpene, PKS, NRPS, etc. For example identified biosynthetic gene clusters and RasGEF and RasGAP homologs, see FIGS. 28-39.

Figure 5:
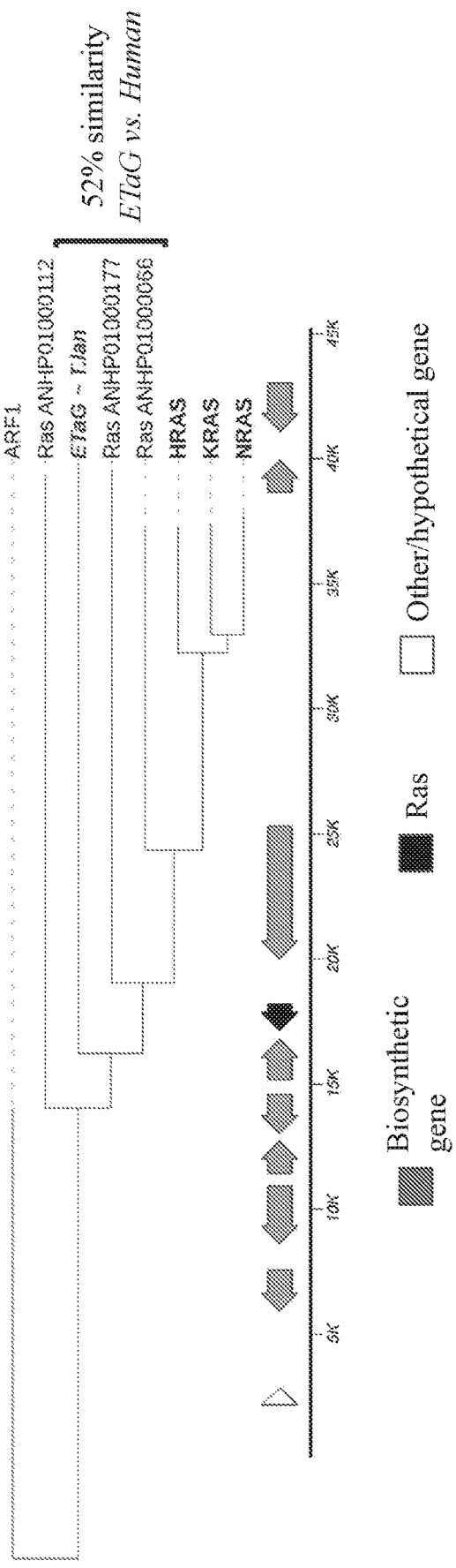
FIG. 5 depicts a Ras ETaG identified in *Thermomyces lanuginosus* ATCC 200065 (public). The example ETaG identified is from the Ras family (pfam00071). Sequence similarity is of Ras domain calculated using MUSCLE alignment algorithm. The ETaG is presented below the scale.

Example identified ETaG sequences are listed below:

FIG. 5: *Thermomyces lanuginosus*. Ras ETaG sequence:

ATGCAGCCGCGGTGAGTGTTGGTCGCGCTCCTTGGCAAAGGTCAATA

CTAATTGGACACAGGCGGGAATATCATATTGTCGTCCTGGGAGCTGG

TATGTCGAGAAGAGATTCGCCACAGCCTATCAGTCGATATGTGTCCC

TAACAATGTTATACAGGAGGCGTCGGGAAGAGCTGCTTGACAGGTAT

GGACGCGATGGACTGCGGCGACAACATGCGACCGATGGCTCACTAAC

TTATCTCATAGCTCAATTTGTACAAAATGTTTGGATTGAGAGTTACG

ACCCGACAATTGAAGATTCCTATCGAAAGCAGATTGAAGTCGATGTG

AGTTCCCGTGGCATTGATGCGATTATACCACCTGCTTACGATATTCT

ATTCGCAGGGTCGACAATGCATTCTCGAGATGTACGTCTCTCTTCAG

AGCTGTCGCGGAGCTATTTCATCTTACTGATCACCGTGCAGTCTGGA

CACAGCCGGAACAGAGCAATTCAGTACGTCTTAACCTCCCAACTCCG

ATGAAAAGGACCATCCACTAACGATGACGACAGCTGCGATGAGGTAT

TACACGTCAATGCGGCGCACATGGCCAATGAAGTTGACATGACTGTC

CAGGGAAATTTACATGAAACAAGGGCAGGGATTCCTGCTAGTCTTCT

CGATCACCAGCATGTCATCGCTGAACGAGTTATCGGAAATCCGGGAG

CAGATCCTCCGCATCAAGGACGATGACAAGGTCCCTATGGTGATCGT

CGGCAACAAGTCCGATCTCGAGGAAAACCGAGCTGTGCCTCGTAGCA

AAGCGTTTGCGCTCTCGCAGAGCTGGGGCAACGCTCCTTACTACGAA

ACATCCGCTCGACGGCGAGCAAACGTCAACGAGGTCTTCATTGACCT

GTGCCGACAGATCATCCGCAAGGATCTGCAAGCTACACAGGCAAAGC

AAGCGGAAGCCAGACAAGTTAAGCGAGAGGCGACTCCTCGCAATGAC

AGGAGCAAGAAGGATAGAAAATCCACAAGGCGTCGGCATCAATGCGC

GATTATGTGA

Figure 6:
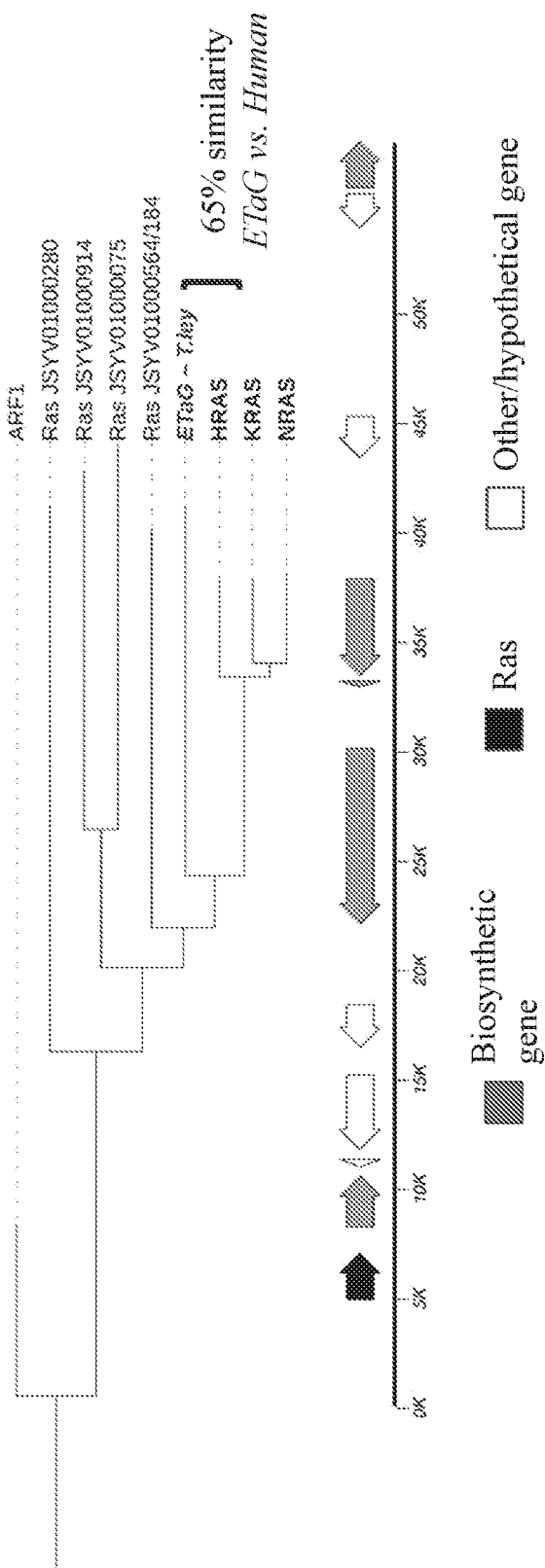
FIG. 6 depicts a Ras ETaG identified in *Talaromyces leycettanus* strain CBS 398.68. The example ETaG identified is from the Ras family (pfam00071). Sequence similarity is of Ras domain calculated using MUSCLE alignment algorithm. The ETaG is presented below the scale.

FIG. 6: *Talaromyces leycettanus* CBS 398.68. Ras ETaG sequence:

ATGCTGGAAGTGCTAGACACAGCGGGCCAGGAAGAGTACACCGCACT

GAGAGACCAGTGGATCCGCGATGGTGAAGGGTTCGTTCTCGTCTATA

GCATCACATCGCGAGCGTCGTTCGCCCGCATACCCAAGTTCTACAAT

CAGATCAAGATGGTTAAAGAATCGGCAAGCTCCGGGTCACCCGCTGG

AGCCAGCTACTTGACGTCGCCGATCAATTCTCCCTCGGGACCCCCGC

TTCCTGTGCCGGTAATGTTGGTTGGCAACAAGAGCGACAAGGCGATG

GACCGCGCCGTCTCTGCGCAGGAAGGCCAAGCTCTTGCCAAGGAGCT

GGGGTGCGAATTCGTCGAGGCTTCCGCCAAGAACTGTATCAATGTCG

AAAAGGCTTTCTACGACGTCGTGAGGATGCTTCGGCAGCAGCGACAA

CAGCAACAGGGAGGACGGGCGCAGGAGCGGCGACCCGCCGCTTTCGG

ATCAGGGCCAATGCGCGATCGGGACGCCGGTCCCGAGTACCCAAAGT

CGTTTCGTCCGGATCGATCAAGGCATCGCAATGGCCTCAAATGCGTT

ATCCTATGAGCTCCCCCCGATGAGTGTTCCGATCGGCGGATCTTTCC

AGCTTCTGACCTCCGCTTATTCATGACCGTTGCTCTCTAGAATGGAT

GGTGTCTAGCTCCGTGTTTCTCTTTCTCGGAGCGTGTGAGCGAGCTT

GAGGACAGTCGTTCCACTTGTGCCCCCTCCTATCCGCCGCAGGCCCT

TGTCGCTGCCGCTTTGCGGACCGCTCGTTTTGTCTACGTTGTACTCG

AAAGCACGGCCTCTGCTTTCGTGGAAGTCTCCCTTTATGCCAGCTTT

GGGTGCGGTGGTCGATATGCAGATACTGTGTTCTATGCTCGCTGCAT

GCGATTCAGAGGCGTCTTGATTCCCCGTGTCAGTATGGGTGTTCTC

-continued

```
GCTATTCAGGGAATCATCTGAAACCAATTTTTCTCATCCGTTCTGTT
TTTGGGAATCGGAACACGGGGGGGATGTCTGGAAATCTGGACCTATA
ACTATAGAAATGTTTCTCACCACCTTTCTCACTCAACCCTCTTGATG
AATATCCGCCCGGCGTCTTCTACTACTTCCTACCGTCTACTACCACC
AATCTCTATTCTTCTTACCACCCACCTTCTGAGCCACTTCTTACACA
TCATTCTCGTTTGGTTTGACAGCAAAGCGGGGAGAGTTCGAAGGACA
GATCCCATGCAGGATTGGAGGACGAGAGGGGAAGAGTCGAAGGGAGA
AAAATAATTAAAAAAAAGAAAGGTGCGGGGGCAGAAGGAGGCAGGTT
TGGTTGAGAGTTGCGAATCGGTCCTGTCGCAGTCAAGTCCCAAAAAA
GAAAAGATCGCAGTCGGCGCATTAGCAGGCATTTTGATACGATGATA
CCCTACAGCCGAGCTTCGAGTTTTTGTGTTCCTTTTCCTTTTTTGCA
AATGCTGATTTAAAAAAATAACAATAGAGCTACATACTGAATGTGGA
TTTTTTTGACCTCTCATCTTTTTGTTGCAGGGATGACCGCCAATTGG
TAAATTCATCCCCAGTCATAATCCGAGCGCAGGATGCATGAACTCCA
GTACCTCATCATATCGCCTGCACGTTCAAGTTCCATCAATCATTCGG
CGGCGCCTACTCTGTACGACTAAGTCTACGGAGTTTGTTCTTGTTGC
GGGGAAGGAAGCGAAAGCCACGACTCCAACAAACAAACTCAGGGTGA
ATTGAATCCTCAGTTTCTACTCTGTAGCCGAAGAGCCATCATTACCA
TTCAGGGGAAGAGCCTAAAGAGCTTGCGAGGTTGGGCTGAGCTGCTG
TGCAGTGAGCAATATATTTGGTCGATGTTTTGGATACGTTATCTGGA
ATGCGCAGATGCAGTGGTTATGCATATCCTCACGTACTCGATTCTGA
TGATTCACGGGACCATACGGAGTCGATACCGAGACTCTCGCTACAAA
CCTGTCAATTGATATCGTGTACAGAGTACCGGAGCCGAGACTGGGAA
ATAGCACAGTCTCAGTCTCAGGTAGCTATCGATCAATTTGACAAGGT
TAGAAGTATCTCGCTAGTAATTGCCAGATGATTCATTCCCGGTTGAA
AACTTTTCCATTGGCCTTCTTCGCTTAG
```

Figure 7:
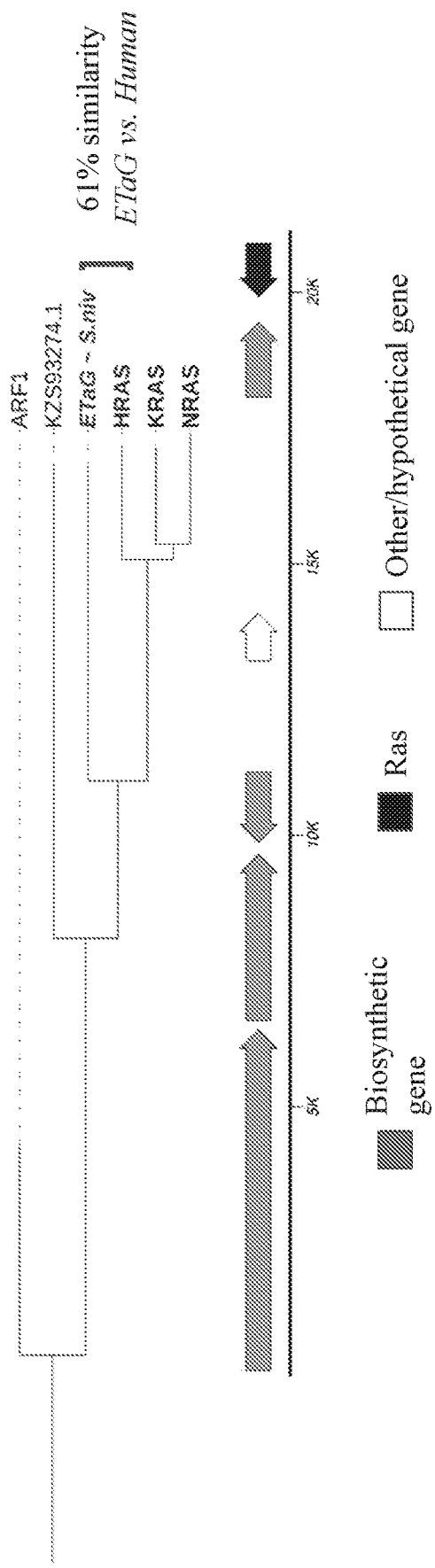
FIG. 7 depicts a Ras ETaG identified in *Sistotremastrum niveocremeum* HHB9708, or in *Sistotremastrum suecicum* HHB10207 (National Forestry Service). The example ETaG identified is from the Ras family (pfam00071). Sequence similarity is of Ras domain calculated using MUSCLE alignment algorithm. The ETaG is presented below the scale.

FIG. 7: *Sistotremastrum niveocremeum*. Ras ETaG sequence.

```
ATGTCGAGAGTGAGTATTTCTGTTTATTGCGGCTCTATCTTGATCTC
ACTCGTCGCTAGTCTGCTGCTCAGGCTTCGTTCCTTCGCGAATACAA
GCTCGTCGTCGTCGGTGGTGGTGGTATGAGCCTTGTCTCTCGTTCTC
TGCAATCAAAATCTCACTCGCTTTTCTCTTGTGCTGCCTAGGTGTTG
GCAAATCCGCTCTGACCATTCAATTCATCCAAAGTCATTTCGTTGAC
GAGTATGACCCTACTATCGAAGGTCAGCCGACCGCTAGGCAACCATT
ATCTGATCAAACAGCTCATCTCGCACTCGACAGATTCTTACAGAAAG
CAATGTGTCATCGATGATGAAGTTGCCCTTTTGGATGTGTTAGATAC
CGCTGGGCAGGAAGAATATGGGTGAGCTCGTCTCGCAGCCCGATTCC
CACGCTTATTGCTAACACGACATCGGCAGCGCAATGCGAGAACAGTA
TATGCGAACGGGAGAAGGATTCTTGCTTGTCTACTCGATAACGTCGC
GGAACTCTTTCGAAGAAATCAGCACTTTCCATCAGCAAATTCTTCGA
```

GTAAAAGACAAGGATGCGTTCCCGGTTATCGTGGTAGCCAACAAGTG
TGACCTTGAATATGAGCGACAAGTCGGCATGAACGGTGCGTTTTTAG
TGTTGTTTCAATCAACATTGTGACTCATCCTTCGTCAGAGGGCCGTG
ACCTGGCCAAGCACTTCAACTGCAAATTTATCGAGACCTCGGCGAAG
CAGCGAATCAACGTTGATGAGGCCTTTTCGAACCTTGTTCGAGAGAT
TCGCAAATTCAACAAGGTATGTAAGCCCAAACCCGACGGAACTCCCG
GCCTGATCTCTTTACAGGAACAACAGACCGGACGTCCTGCGACCATG
GCTCCGAGCGGCCCTGTGGGTGCATTCGGTGGTCCCCCCGGCATGGA
AGATGGACCTCATGACGCTGGTTGCTGCTCTGGATGTGTCGTTGTAT
AA

*Sistotremastrum suecicum*. Ras ETaG sequence:

```
ATGTCGAGAGTGAGTATTTCTGTTTATTGCGGCTCTATCTTGATCTC
ACTCGTCGCTAGTCTGCTGCTCAGGCTTCGTTCCTTCGCGAATACAA
GCTCGTCGTCGTCGGTGGTGGTGGTATGAGCCTTGTCTCTCGTTCTC
TGCAATCAAAATCTCATTCGCTTTTCTCTTGTGCTGCATAGGTGTTG
GCAAATCCGCTCTGACCATTCAATTCATCCAAAGTCATTTCGTTGAC
GAGTATGACCCTACTATCGAAGGTCAGCCGACCGCTAGGCAACCATT
ATCTGATCTAACAGCTCATCTCGCACTCGACAGATTCTTACAGAAAG
CAATGTGTCATCGATGATGAAGTTGCCCTTTTGGATGTGTTAGATAC
CGCTGGGCAGGAAGAATATGGGTGAGCTCGTCTCGCAGCCCGATTCC
CACGCTTATTGCTAACACGACATCGGCAGCGCAATGCGAGAACAGTA
TATGCGAACGGGAGAAGGATTCTTGCTTGTCTACTCGATAACGTCGC
GGAACTCTTTCGAAGAAATCAGCACTTTCCATCAGCAAATTCTTCGA
GTAAAAGACAAGGATGCATTCCCTGTTATCGTGGTAGCCAACAAGTG
TGACCTTGAATATGAGCGACAAGTTGGCATGAACGGTGCGATTCTAG
TGTTGTTTCTGTCGATATTGGGACTTATCCCCCTTCAGAGGGCCGTG
ATTTGGCCAAGCACTTCAACTGCAAATTTATCGAGACATCGGCGAAG
CAGCGAATCAACGTTGATGAGGCCTTTTCCAACCTTGTTCGAGAGAT
TCGCAAATTCAACAAGGTATGTAAGCCCAAACCCGACGGAACTCCCG
GCCTGATCTCTTTACAGGAACAACAGACCGGACGTCCTGCGACCATG
GCTCCGAGCGGCCCTGTGGGTGCATTCGGTGGTCCCCCCGGCATGGA
AGATGGACCTCATGACGCTGGTTGCTGCTCTGGATGTGTCGTTGTAT
AA
```

Figure 8:
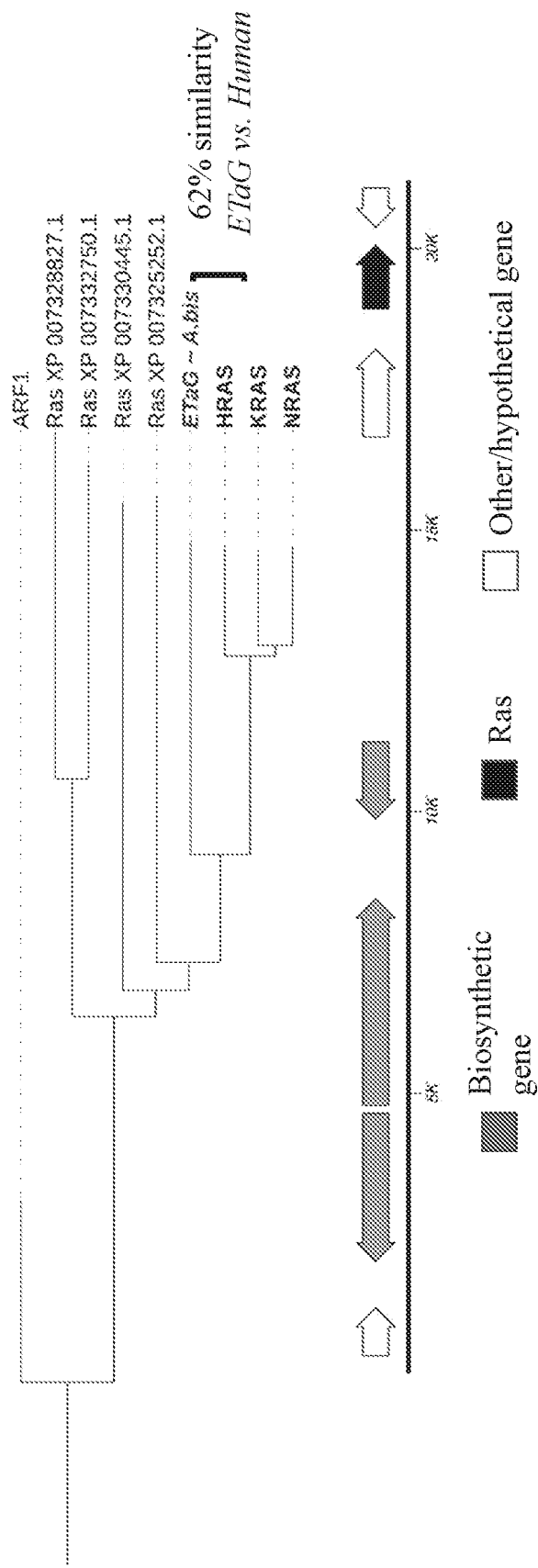
FIG. 8 depicts a Ras ETaG identified in *Agaricus bisporus* var. *burnettii* JB137-58 (Fungal Genome Stock Center). The example ETaG identified is from the Ras family (pfam00071). Sequence similarity is of Ras domain calculated using MUSCLE alignment algorithm. The ETaG is presented below the scale.

FIG. 8: *Agaricus bisporus* var. *burnettii* JB137-S8. Ras ETaG sequence.

```
ATGGCAAACAACGCTGCGTCCAGAGTATGTCCTCCCCACAAACCACC
CTCAGTTGCCTGGCTTATGCTCTATTTCAGGCTGCTCAGGCCCAGTT
CCTGAGAGAATACAAGCTCGTAGTGGTCGGAGGAGGAGGCAAGTGCT
ACCCGCCCTTACAAGCTAGCAAGTCCTAAAGTCGTGTACAGGTGTTG
GAAAATCTGCATTGACTATCCAATTCATTCAAAGCCATTTCGTGGAC
```

-continued

```
GAGTACGACCCAACTATCGAGGGTGAGCTTCTTTCTCACCAATCAAT
CCCCTTCCAGGTTATGACATTTCGGAACATTTGTGCTAACATTCTCG
TCTTAAAACAGACTCGTACAGGAAACAATGCGTCATTGATGAAGAGG
TCGCCCTTCTCGATGTCCTGGATACCGCTGGTCAAGAAGAATATGGG
TCAGTGTGCTCTCCTGAATAAATTCCGAAGCAGTCCCCGATTTTTTT
TCCTTTCGTCTCGTGATTCGACTATGAAAATGGTCTTCCACGAGGCG
AAGCTTTCATTTCCCGGCATAATTCAGTTATACGACCCTGGATCTAA
CCCTATATGTACTTATTTTCCAGTGCCATGCGGGAGCAATACATGCG
TACTGGGGAGGGATTTCTTCTCGTCTACAGCATCACCGCGCGTAGCT
CCTTTGAAGAAATCAACCAGTTTTACCAGCAAATTTTGAGGGTCAAA
GATCAAGATTCTTTCCCTGTTATTGTCGTTGCAAACAAGTGCGATTT
GGAATATGAACGCCAAGTTGGTATGAACGGTATGTTATCAAACCTTG
GAGTATATCAGGGCCCCAGTAGTGACGCAACCTACAGAGGGCCGAGA
TCTCGCGAGACATTTTGGCTGCAAATTCATCGAGACGTCTGCCAAAC
AACGAATAAACGTGGATGAAGCTTTCAGCAATCTTGTTCGTGAAATC
CGAAAATATAACAAGGTCGGTTTTCCGCATCACACGCAGAGATTTTA
CAAACTCATTGGTGCTTTTATAGGACCAACAAACAGGCCGCCCTCTC
CACGGCAGCGGTGGTGGAGCCGGCGGTTATGGTGGCAAGGACCACAA
TGACGATGGAGGTGCTGGCTGCTGCGGCGGTTGCGTTATTCTTTAA
```

Figure 9:
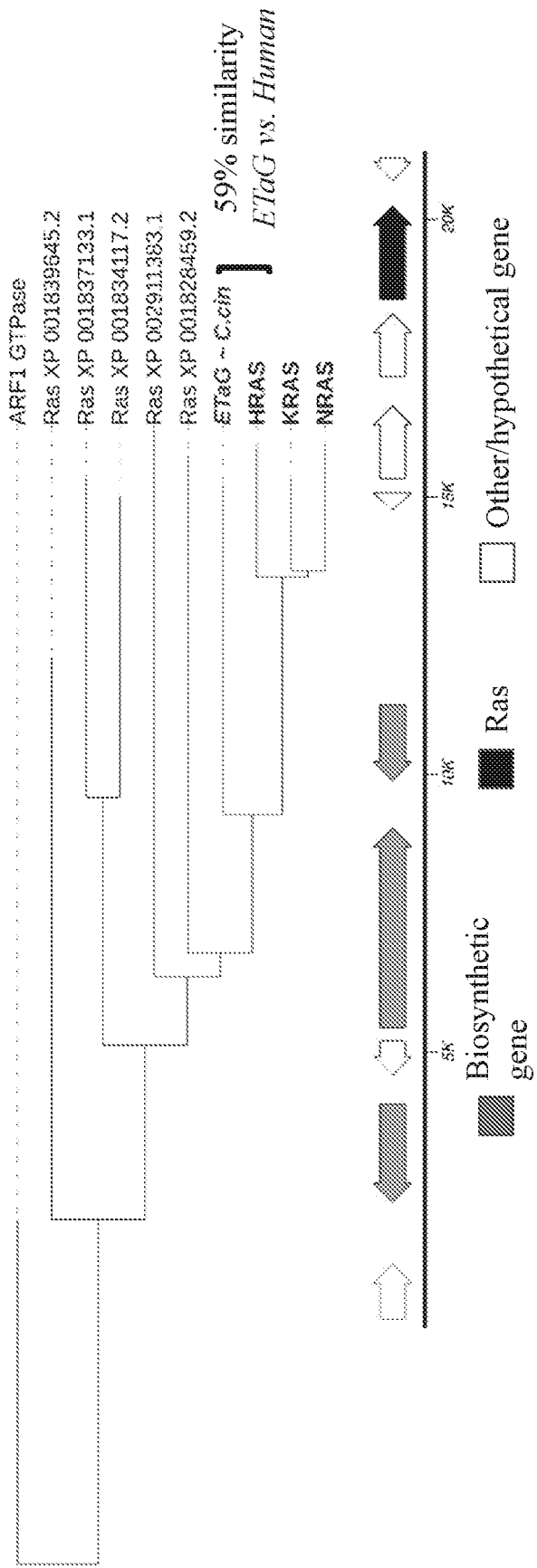
FIG. 9 depicts a Ras ETaG identified in *Coprinopsis cinerea okayama* 7#130 (Fungal Genome Stock Center). The example ETaG identified is from the Ras family (pfam00071). Sequence similarity is of Ras domain calculated using MUSCLE alignment algorithm. The ETaG is presented below the scale.

FIG. 9: *Coprinopsis cinerea okayama*. Ras ETaG sequence.

```
ATGCCTGAGGTGATGAATGCTATGTACGCCACGAAAGGCGGTATCTTCG
ACGTCAGCGAGAATGATAAGGTTTGGCGTTTGCAGTGTTTCAAAGCTGG
CCTCTGTTGTGTTGGAGAATACTCGGATGCTGATATACATATGGTTTAT
CGAATACAAGTACGCGTATAAGGAAAGCTGGGGTAGACAAGGGACTATA
GCTGGATCTTAACTCCCAGGAGGGGACGACATGAGAGAATGCGGTCTAC
AGCAATTCTGATGCTCGAAAATCCATCAGCAGAGGTCAACCTTGGGTTT
CTAGCGAAAAGAAGGGAGATAGGAAGCCCGGAATATCAAAACACGCGTC
GGATTGTGGTCCAAATTGAAAAATGACCGAGAGCCTCGAGCTCGTGTCG
CGAGATGTTTGCACTTGAGATTTAAACTCCGCTGATGATGGCCTTTGAA
GTGAGTTTGGTTACGATGTTTAGAGGAACCCAGTCGCCCCCTGCTCCCG
CTCAACTCCCTAAATACCCTTCCTGACCATCTTCTTTCTTTCCCAAATC
TTTTTCTTCTCTTTCAACAGATTTCATTTCTGAAGCATGGCTGCCAGGG
TCCGTCAAATCCCACAGTCTGCACCGTGGAACCTCAGCAAACTCACACA
GCGTCCAACAGGCTCAGTTCTTGAGGGAGTACAAGCTCGTCGTCGTAGG
TGGTGGTGGTATGTTGCACAGCTCTTAGAACGGAATGTAGTCTCACCTG
TGGTGCCCCAGGTGTTGGAAAGTCGGCCCTGACTATTCAGTTCATCCAA
TCCCACTTCGTGGATGAATATGACCCGACTATCGAAGGTCCGTATAACA
AGGCCTTCTCTCGCAAGGATGCAATAGCTTATGCTTATTCGACACAGAC
TCGTACAGAAAACAGTGCATCATCGACGACGAGGTCGCACTCCTCGACG
```

```
TTCTCGATACCGCCGGACAGGAAGAGTATGGGTGAGTACCCGCGCTGCA
CCCCTCTATTTTCCACCGAATGCTTCGTGGACAGCCCAACTTTTGATCC
TCGTATCCCATACCACCGCTTTCCTTGTTCCCGGAATCTTTGCATCACC
ACCTCTCCACCTTGCCCTCTTCTTCGGGACGTTCCGTGATTAACACACA
CCTACAGAGCCATGCGGGAGCAATACATGCGCACGGGCGAAGGCTTCCT
TCTCGTCTACTCTATCACCTCCAGAAACTCGTTTGAGGAAATCAGCATT
TTCCACCAACAAATTTTGCGAGTCAAGGACCAGGATTCCTTCCCCGTCA
TTGTTGTGGCTAACAAGTGCGATCTCGAATATGAACGTCAAGTTGGCAT
GAACGGTGTGTAGTCCATCTTTATGTCCCTTGCCGACATGACATGAACA
ACGTATTGCAGAGGGGCGTGATCTCGCCAAACACTTTGGTTGCAAATTC
ATCGAAACCTCGGCCAAGCAACGAATCAACGTCGACGAGGCATTCAGCA
ACCTCGTTCGGGAGATTCGCAAGTCAACAGGGTGAGCAATCCTCTCTTC
CAAGGTATTCTGACTAGCATTCAAACTGTCTCATGCCCCCAGGAACAAC
AAACCGGTCGTCCTGCCATCGCAGCAGGTGGAGGTGGTCCAGCCGGCTC
CTACACCCAGGACAGGCACCACGATGAGGCACCTGGATGCTGTGCCGGA
TGTGTTATTGCCTAA
```

Figure 10:
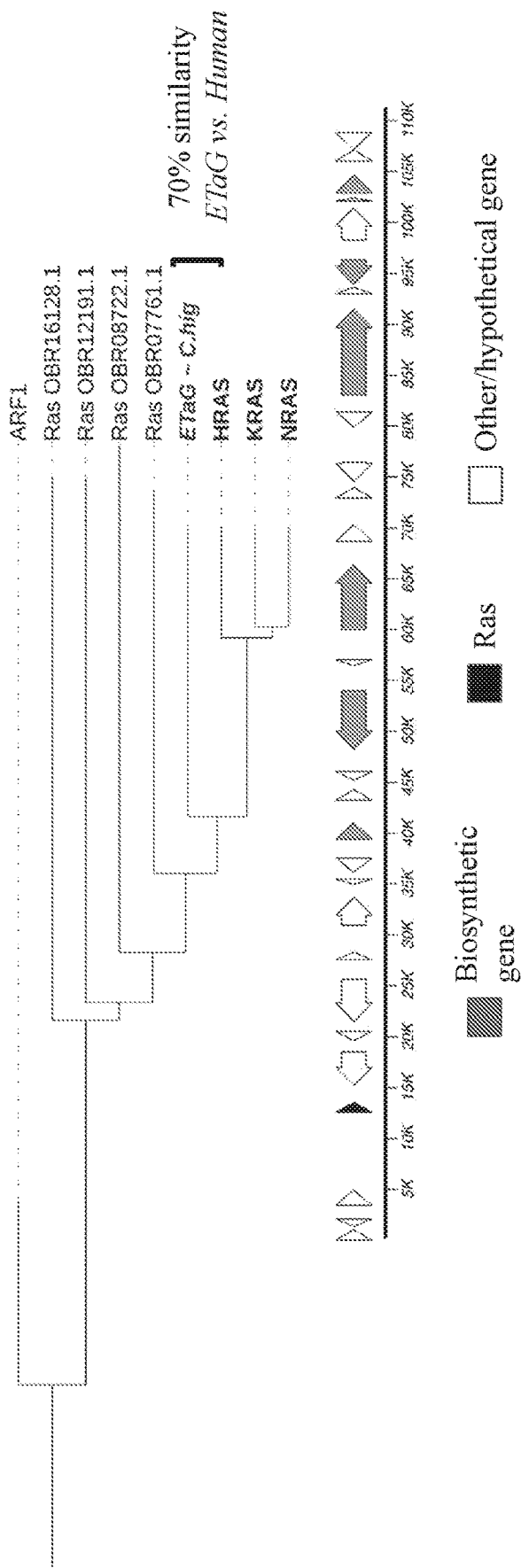
FIG. 10 depicts a Ras ETaG identified in *Colletotrichum higginsianum* IMI 349063 (CABI). The example ETaG identified is from the Ras family (pfam00071). Sequence similarity is of Ras domain calculated using MUSCLE alignment algorithm. The ETaG is presented below the scale.

FIG. 10: *Colletotrichum higginsianum*. Ras ETaG sequence.

```
ATGGCGTCCAAGGTTCGTCGTCGCCACCTCCCGTTTCCCTTCATTTCTT
TTGCCGCCTCGTCGCTCCATCGCTCCATCGCCCCATCGATCCGTTGCTA
ACCAGTTGCCATCTCGCAGTTTCTGAGGGAGTACAAGTTGGTCGTCGTC
GGCGGCGGTGGTGTCGGTAAATCCTGCTTGACCATCCAATTGATTCAGA
GCCACTTTGTCGACGAATATGACCCGACGATCGAAGGTGCGTCGTCCCG
AACTTCTTGCTCCACCGTTCGATGCGACGGCTTCGAATCAATCGCATGC
TAATGTGGATCTCACCCATTTCAGATTCCTACCGCAAGCAGTGCGTCAT
CGACGAGGAGGTCGCTCTACTCGATGTCCTCGACACGGCCGGTCAGGAG
GAGTACTCCGCCATGAGGGAGCAGTACATGAGGACGGGAGAGGGTTTCC
TTCTGGTTTACTCCATCACTTCGCGACAGAGCTTCGAGGAGATCACCAC
ATTCCAGCAGCAGATTCTGAGAGTAAAGGACAAGGACTACTTCCCCATG
GTCGTCGTCGGCAACAAGTGCGATCTGGAGAGCGAGAGAGAAGTCACAC
GACAAGGTATGATTCTGATTCCTGCTGTGCCGCGACACCGCATGAGGCG
GCTCCTTTCGAGGCCCAGGCCCGGTGTGGATTCATTGATGGAATGAAAA
GTAGCTGACATCATTCACTCGTGCGCGCTACAGAGGGAGAGGCCCTTGC
CAAGTCATTCGGCTGCAAGTTCATCGAGACGTCGGCCAAGTCTCGCATC
AACGTCGACAAGGCTTTCTATGATATTGTCCGAGAAATCCGTCGGTACA
ACCGCGAGATGCAGGGCTACTCTACCGGCAGTGGCGGCGCCTCGGGCAT
CAACGGCCCCCGAAGCCCATGGACGTCGAGAACGGCGAGCAAGAGGCA
GGCTGCTGCTCCAAGTGCGTACTAATGTGA
```

Figure 11:
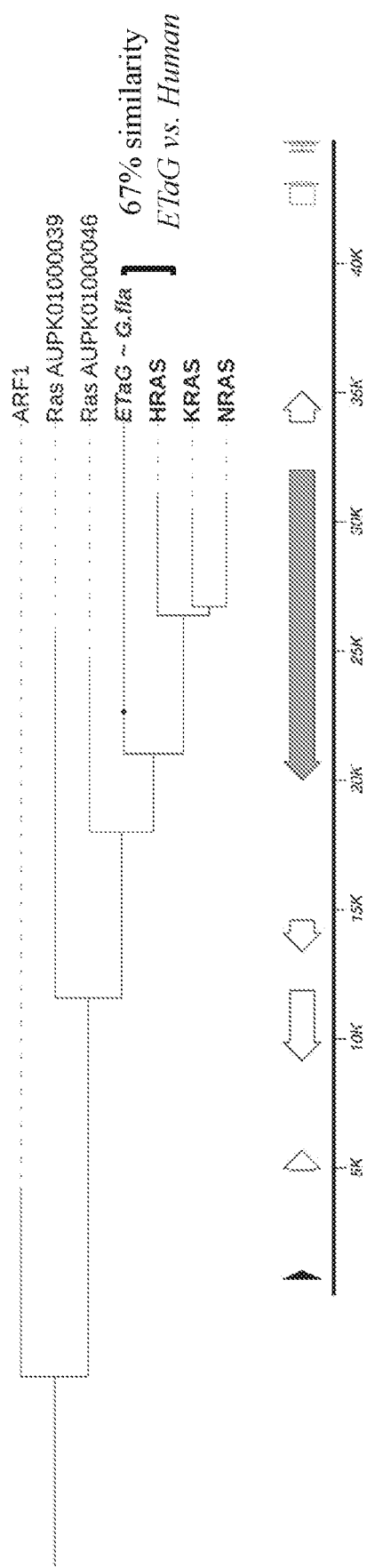
FIG. 11 depicts a Ras ETaG identified in *Gyalolechia flavorubescens* KoLRI002931. The example ETaG identified is from the Ras family (pfam00071). Sequence similarity is of Ras domain calculated using MUSCLE alignment algorithm. The ETaG is presented below the scale.

FIG. 11: *Gyalolechia flavorubescens* KoLRI002931. Ras ETaG sequence.

```
ATGGCTTCAAAGGTAAGTCCATCTGTCTCTTTAGAGTATTCTCATTGCT
CTTTGCTACCGAGCTTCTCCATGGACGCTGACCCTTACCTGCTCAAGTT
CCTACGGGAATACAAGCTCGTCGTCGTTGGCGGAGGAGGTGTGGGCAAG
TCCTGCTTGACCATCCAGCTCATCCAGAGTCACTTCGTCGACGAATACG
ATCCCACCATTGAAGGTAAATAGATTCGTCCTATCCACCCATTGCGCTT
TTACTGATCGAAGCGATTTGCAAGACTCCTACCGGAAGCAATGCGTCAT
CGACGAAGAAGTCGCCTTACTCGATGTACTAG
```

Figure 12:
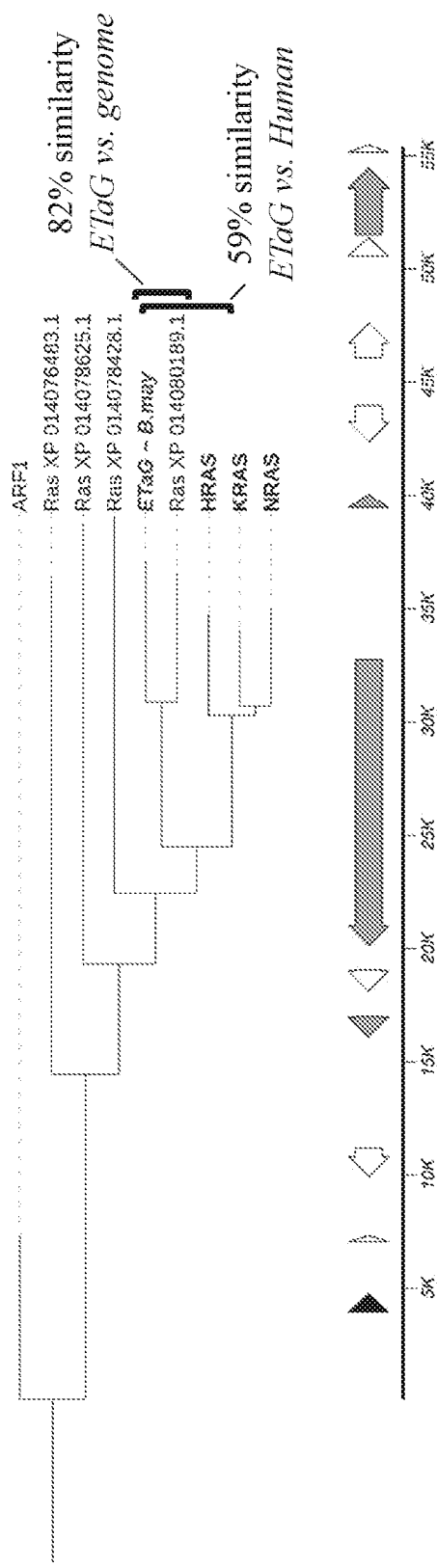
FIG. 12 depicts a Ras ETaG identified in *Bipolaris maydis* ATCC 48331. The example ETaG identified is from the Ras family (pfam00071). Sequence similarity is of Ras domain calculated using MUSCLE alignment algorithm. The ETaG is presented below the scale.

FIG. 12: *Bipolaris maydis* ATCC 48331. Ras ETaG sequence.

```
ATGTTCTTGCCTCAACTCTACTCCCTCAACCCTGCCTTGGCTGCCAAAC
ATGCTGATCCTCTTGCTCCTACAGCCCAGTTTGTGCAAAACGTGTGGAT
AGAGAGCTATGATCCCACCATCGAGGACTCGTACCGAAAGGTCCTCGAA
GTAGACGTGCGTACACGACACTCTTACTAGCCGCGTTTTTTTCACTGAC
CCACTCTCCCTCCCAGGGCCGTCATGTCATTCTCGAGATCTTGGATACT
GCCGGCACAGAGCAGTTTAGTAAGTGATTACATACATAGCCCCACCCCA
CGTGGACCCAAGACTAACACGACAATAGCTGCCATGAGGTAGAGTTTCC
TACTACCCCCTTACTCGGTAAACATCAAAACTTACACGGATGCAGAGAA
CTGTACATGAAAACGGGCCAAGGATTCCTTTTGGTCTTCAGCATCACAT
CAGAATCTTCCTTTTGGGAGCTTGCCGAGCTGCGTGAGCAGATACGACG
CATCAAGGAAGACAGCAACGTACCCATGGTTCTCATTGGCAACAAGTCG
GACCTAGAAGACGACCGTGCCGTGCCGCGCCCACGAGCATTTGCCATTT
CGCGTGAATGGAACGTTCCTTATTTCGAAACCAGTGCTCGAAGGAGAGC
CAATGTCGACGAAGCCTTTGTCGACCTCTGCAGGCAAATCATCCGCAAG
GATCAGAACGAACGAAACCGCATGGCCCCACCGGATTCCCCGAGGCCTG
GCGGTCCCAGGAGCAGAACTCACACGGGACGGCCAAAGCGCAAGGCTCA
CCGGCCCCATTGTACCATTCTTTAA
```

Figure 18:
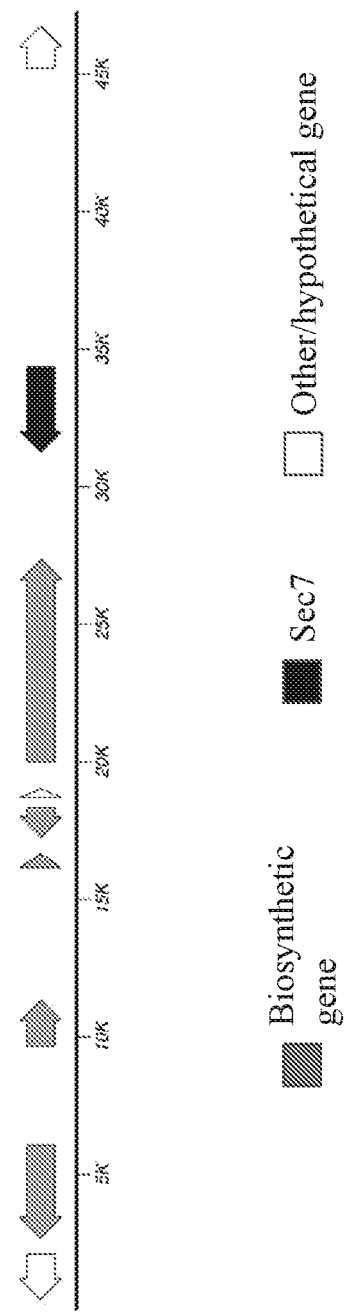
FIG. 18 depicts a biosynthetic gene cluster with Sec7 homolog in *Penicillium vulpinum* IBT 29486.

FIG. 18: *Penicillium vulpinum* IBT 29486. Sec7 ETaG sequence.

```
ATGGAAGTTGAAAGGCCGGATGGTTGGCATCATCACTGCTGACCACGAA
CAGACATCACGAAATATGACACACCTGCTCTACTACACCCCTTCCTCCA
AGTAATACGATCATCCTCAACCTCTGCTGCGATCACCTCCCTCGCTCTC
ATCGCCATCACGAAATTCCTCTCCTACAAAATAATCTCCGGTGACTCCG
CTCGGCTGGCTGAAGCCATGCAGCTCCTCTCATCAGCTCTCACGCACTG
CCGGTTCGAGGCAAGCGATTCAGCAACGGACGAAATTGTACTCCTGCAG
GTACTGAATCTCATGGAAAGCATTATCTTGAGTCCAGGAGGTGAATCTC
TCTGCAATGAGAGCGTTTCTGAGATGATGCAAACTGGACTGAGCATGTG
CTGCCAACCCAGGCTTTCGGAACTCCTACGACAGTCTGCTGAGATTGCC
ATGGTCTCTATTTGCCAATTGGTCTTCGAGCGATGGAAGCACCTAGAAG
AAGAGGTGGGCGAAGAGCTAGGGGCCTTGGATCAGGATGTCAGGGCCGA
TATGGGCACGATGAAGCTCCTTGATTCAAAAATGCAGACCTCCTTGACC
GGTCCAAACTCCAAGAATCTTAAATCTGAGGAGAAGACACGGTCTTTTG
CGAGCGTGGAGAAGCTGATCAATGAGTCCACAGGGATGACACTGCAAAA
GGGCGACGCCACAATTGATCTACCGTCAATGCACGATGAACAGGATGAA
GGCGAGGCGCTCCCAATCAAGCCATACTCCCTGACGTTGATACGAGAGC
TTCTTGTGATCCTCATCAATATACTAGATCCTGAGGACAAGAAACAAAC
AGACACAATGCGTATCACGGCACTGCGCATTCTGCATGTTGTGTTGGAA
GTAGCGGGCCCATCAATCGTCAACCATACTAGTCTAGCAACCCTGACAA
AGGACACGCTATGCCGATACTTGCTCCAATTGGTTCGCTTGGATAACAT
GAAGATTATCAGCGAGTTGCTCTGTGTGTGTGTTACTTTATTTGCAACA
TGCCGAGGTGTACTCAAGCTACAGCAGGAGCTATTCCTATCGTATGTGG
TGACCTGTGTGTTTCCGACAATGGATATTCCGCTAGAGCCTGGTATCGA
CCCTTCTCTTTACGAGGGTGTACCGCAGTCATTCAGCCTCCTCAAGCAA
TCAAAATCACAGTCACCTGCGCAAAAATCTACAAGTGGCAAATCGACGC
CCAAGTCTGCCAAGGATCGACAGAAGCTGGGACCCGAAGACAGCATAAG
GACACCCGATGCTCGTGAGGCGATATTAGAGAGCGTGAGCGCCTTGGTT
AGGATCCCCTCTTTTATGGTCGAGCTGTTCGTCAACTACGATTGCGATA
TTGATAGAAGCGACCTATGTTCGGATCTGGTTGGACTTCTTCGCGGAA
CGCTTTCCCAGACTCAGCCCAGGGGAGTACAACAAACCTCCCACCGCTA
TGTTTGGACTCTCTTCTATCCTATGTGCAATCCATTGCAGATAGACTCG
ATGATGCGCCCCTGATAGAGGGCTTCCGTGACCCCAATGCCCTACGACA
GCAGCGGTCACGTAAGAGTATGATTATGAAGGGTGCCTCGAAATTCAAT
GAGAACCCAAAGGCTGGCATCGCATTTCTAGTCGCCCAAGGGGTCATAC
AAGAGCCTGAGAATCCTAAGAACATTGCGGAGTTTATCAAAGGCACTAC
GAGAATTGACAAGAAGATCCTGGGGGAGTTTATTTCAAAGAAAACAAAC
GAAAATATATTGAACGAGTTCATGAAGCTTTTTAACTTCGCGGAAAAC
GAATTGACGAGGCTATACGCGAGTTACTGGGTGCATTCCGCCTTCCTGG
TGAGTCGGCACTTATAGAGCGAATTGTGGAGGTGTTCGCTGCACAGTAT
ATGGACGACGCCAAACCCGCAGGAATTGCAGACTCCACTGCAGCATTTG
TTCTCGTGTATGCCACCATCTTGTTAAACACAGATCAGCATAATCCCAA
TTTCAGGGGCCAGAAACGTATGACCATTGAGAACTTTGCCCAGAATCTC
AGGGGTGTTAACGATCAGGGGACTTTGATTCCAACTTCCTTCAGGAAA
TCTTTGATTCTATCCGGACACATGAGATTATCCTGCCAGAGGAGCATGA
TGATAAGCATGCCTATGATTACGCTTGGAATGAGCTGTTGATCAAGGCC
GAATCCACTTCAGACTTGGTGTCTTGCAACACCAACATTTTTGATGCGG
ATATGTTCGCGGCAACATGGAAGCCAATCGTCGGGACACTATCATATAT
GTTCATATCCGCGACTGACGACGCTGTGCTTTCAAAAATAGTAACCGGT
TTCGGCCAGTGCGGTCAGATTGCTGCGAAGTACAGACTAAGTGATGCCT
TGGATAGGATAGTAGCCTGTCTGTCGCATATCAGCACGCTTGCTCCAGA
AGTCACACCAAGCACGAGTCTCAAAATCGAGGTCCAGCATGAGAAACTT
```

-continued

```
AGTGTAATGATCTCCGAAACCGCCGTTCGATTTGGGCGTGATGACAGAG

CCCAGCTTGCAACAGTAGTGCTGTTCCGAATTCTCAATGGTAACGAGGG

TGCAATTCGGGATGGATGGGAACAGGTAAGACTTCCATCAACAAAAGCA

ATTGAGATATATAAGCTCACAGCTGTAGATTCTGCGAATATTGCTGAAT

CTTTTTATAAATTCTTTGATACCCTCCTCGTTCTCCTCAGCTCGCAAAT

CGCTTGAACTTCCATCTATCCCGCTACAAAGCCCCACTCAGATCATCAA

CAAAGATGATAGAGCAGCGGACACCAGCCTGTTTTATGCCTTTGCTTCT

TATGTTTCGAGTTTCGCGAACGGTGAGCCACCGGAACCTTCAGACGAAG

AGATTGAGAACACCTTGTGTACAATCGATACTATCAGCGCTTGTTCGTT

GGACGAAATCACATCCAACATCTTGTAAGTCATAAACCGCGTGGCTAAT

CAGGACATGAATTAACAAGACCTCTAGCGACATGTCCACAGAGGCTTTG

AGACCTCTGTTCATGGCGCTTTTGTCACGACTACCCGAAGATACATCGC

TCCACGGTATTGCAGTAA
```

Figure 20:
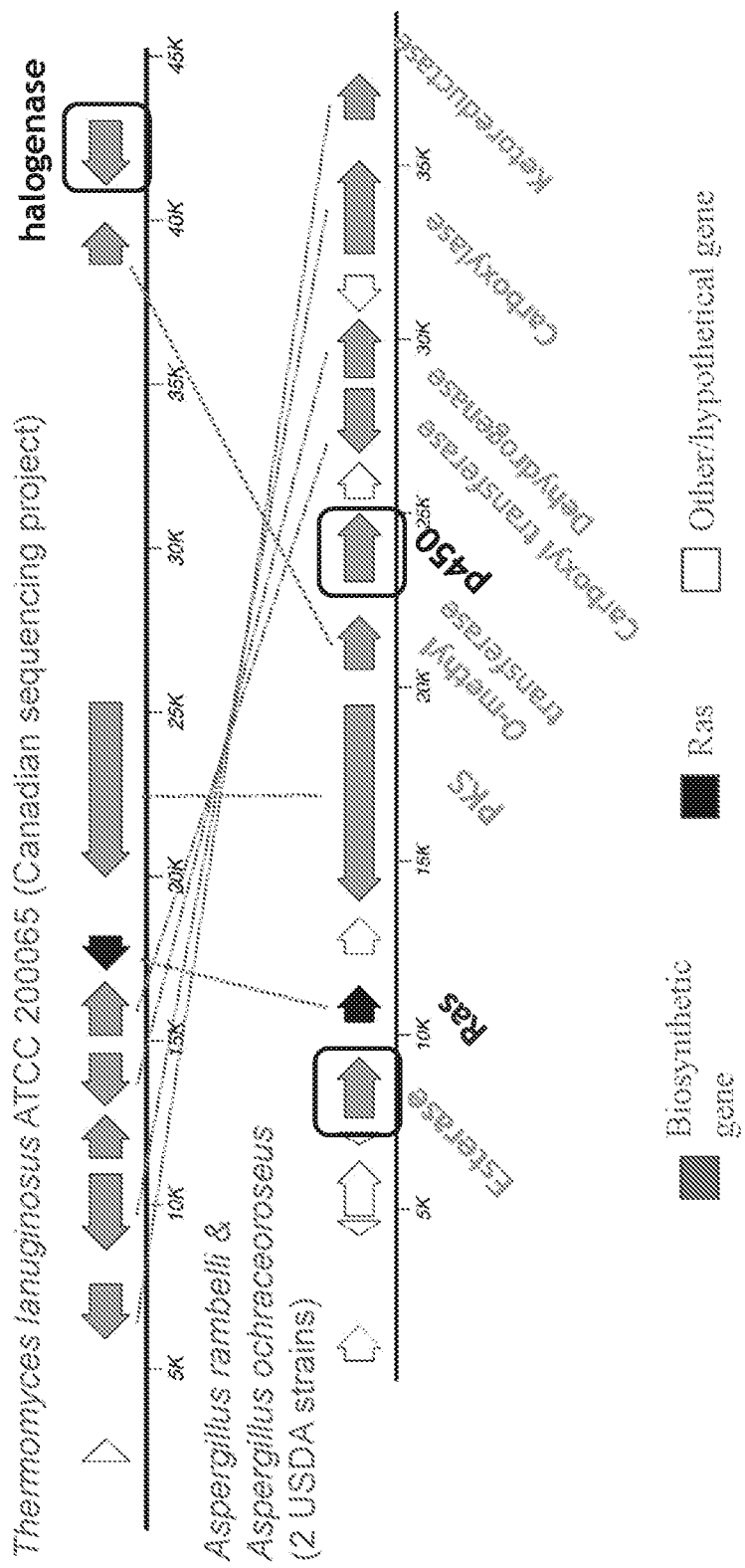
FIG. 20 depicts example biosynthetic gene clusters related to Ras, e.g., from *Thermomyces lanuginosus* ATCC 200065, *Aspergillus rambelli*, and *Aspergillus ochraceoroseus*. Illustrated Ras homologs are indicated in black.

FIG. 20: *Thermomyces lanuginosus* ATCC 200065. Ras ETaG sequence.

```
ATGCAGCCGCGGTGAGTGTTGGTCGCGCTCCTTGGCAAAGGTCAATACT

AATTGGACACAGGCGGGAATATCATATTGTCGTCCTGGGAGCTGGTATG

TCGAGAAGAGATTCGCCACAGCCTATCAGTCGATATGTGTCCCTAACAA

TGTTATACAGGAGGCGTCGGGAAGAGCTGCTTGACAGGTATGGACGCGA

TGGACTGCGGCGACAACATGCGACCGATGGCTCACTAACTTATCTCATA

GCTCAATTTGTACAAAATGTTTGGATTGAGAGTTACGACCCGACAATTG

AAGATTCCTATCGAAAGCAGATTGAAGTCGATGTGAGTTCCCGTGGCAT

TGATGCGATTATACCACCTGCTTACGATATTCTATTCGCAGGGTCGACA

ATGCATTCTCGAGATGTACGTCTCTCTTCAGAGCTGTCGCGGAGCTATT

TCATCTTACTGATCACCGTGCAGTCTGGACACAGCCGGAACAGAGCAAT

TCAGTACGTCTTAACCTCCCAACTCCGATGAAAAGGACCATCCACTAAC

GATGACGACAGCTGCGATGAGGTATTACACGTCAATGCGGCGCACATGG

CCAATGAAGTTGACATGACTGTCCAGGGAAATTTACATGAAACAAGGGC

AGGGATTCCTGCTAGTCTTCTCGATCACCAGCATGTCATCGCTGAACGA

GTTATCGGAAATCCGGGAGCAGATCCTCCGCATCAAGGACGATGACAAG

GTCCCTATGGTGATCGTCGGCAACAAGTCCGATCTCGAGGAAACCGAG

CTGTGCCTCGTAGCAAAGCGTTTGCGCTCTCGCAGAGCTGGGGCAACGC

TCCTTACTACGAAACATCCGCTCGACGGCGAGCAAACGTCAACGAGGTC

TTCATTGACCTGTGCCGACAGATCATCCGCAAGGATCTGCAAGCTACAC

AGGCAAAGCAAGCGGAAGCCAGACAAGTTAAGCGAGAGGCGACTCCTCG

CAATGACAGGAGCAAGAAGGATAGAAAATCCACAAGGCGTCGGCATCAA

TGCGCGATTATGTGA
```

*Aspergillus rambelli*. Ras ETaG sequence:

```
ATGCTGGGAATAGCGGTCACTAATAATGCCTCCTTCGGTGTGACCGGTA

GACGGGAATATCACATTGTCGTGTTGGGTGCTGGAGGAGTGGGAAAAAG

TTGTCTTACTGGTATGATTCTCGGTCGCGTCGGCTTCGTGCTTGCCTCG

GAAGGCCGTCTCTGCTCTCTAGACCAATCAGTCGCTTACTTGTGGCAGC

GCAATTTGTGCAAAACGTTTGGATTGAAAGCTATGATCCGACGATTGAA

GACTCTTATCGCAAGCATATCGAGGTAGATGTATGTTTATCCTGCTCTC

AACTTCATTCTCGGGTTCATTCTCAAGTCGCTGACATTTTCTAGGGCCG

ACAATGTATTCTGGAAATGTATGTCACAAGGAACACGGATGGTGGTTCG

GAATTGCGCTTTACGTGTAAACAAACACGGCTGGCTGACCCTTGACCTG

TCAACAGACTTGATACAGCGGGGACAGAACAATTTAGTGAGTTATCTTG

CTCTTGATGCTGGGTTTTCTCTCCACTAACGTTTTCCCAGCGGCCATGA

GGTAATGAATGCTATATCCATGGGGTCATCGGGACTCACATCTCTCAGT

TGCCAGATCTCGATCGCTAACATGTGAATCCTGCAGAGAACTATATATG

AAGCAAGGCCAGGGCTTTTTGCTTGTATTCTCTATCACTAGCATGTCGT

CTCTGAACGAGCTGTCCGAATTACGAGAACAAATTATTCGCATTAAAGA

CGACGAGAAAGTTCCCATCGTCATTGTGGGCAATAAATCGGATTTGGAG

GAAGACCGCGCAGTCCCACGTGCTCGTGCATTTGCTCTTTCTCAGAGCT

GGGGCAACGCTCCCTACTATGAAACATCGGCGCGTCGACGAGCCAATGT

TAATGAGGTCTTCATTGACCTGTGTCGACAGATTATACGGAAGGACCTC

CAGGGAAGTTCGACCAGCGATTATGATGCTGCCGCACGTAAACGCGAGG

GTCAAACCCGACAAGACCGAAAGCGAGAGAGAAAACGACAAGTGCGGCG

AAAGGGTCCTTGTGTCATTCTCTAA
```

*Aspergillus ochraceoroseus*. Ras ETaG sequence:

```
ATGCTGGGAATAGCGGTCACTAATAATGCCTCCTTCGGTGTGACCGGTA

GACGGGAATATCACATTGTCGTGTTGGGTGCTGGAGGAGTGGGAAAAAG

TTGTCTTACTGGTATGATTCTCGGTCGCGTCGGCTTCGTGCTTGCCTCG

GAAGGCCGTCTCTGCTCTCTAGACCAATCAGTCGCTTACTTGTGGCAGC

GCAATTTGTGCAAAACGTTTGGATTGAAAGCTATGATCCGACGATTGAA

GACTCTTATCGCAAGCATATCGAGGTAGATGTATGTTTATCCTGCTCTC

AACTTCATTCTCGGGTTCATTCTCAAGTCGCTGACATTTTCTAGGGCCG

ACAATGTATTCTGGAAATGTATGTCACAAGGAACACGGATGGTGGTTCG

GAATTGCGCTTTACGTGTAAACAAACACGGCTGGCTGACCCTTGACCTG

TCAACAGACTTGATACAGCGGGGACAGAACAATTTAGTGAGTTATCTTG

CTCTTGATGCTGGGTTTTCTCTCCACTAACGTTTTCCCAGCGGCCATGA

GGTAATGAATGCTATATCCATGGGGTCATCGGGACTCACATCTCTCAGT

TGCCAGATCTCGATCGCTAACATGTGAATCCTGCAGAGAACTATATATG

AAGCAAGGCCAGGGCTTTTTGCTTGTATTCTCTATCACTAGCATGTCGT

CTCTGAACGAGCTGTCCGAATTACGAGAACAAATTATTCGCATTAAAGA

CGACGAGAAAGTTCCCATCGTCATTGTGGGCAATAAATCGGATTTGGAG
```

-continued

GAAGACCGCGCAGTCCCACGTGCTCGTGCATTTGCTCTTTCTCAGAGCT

GGGGCAACGCTCCCTACTATGAAACATCGGCGCGTCGACGAGCCAATGT

TAATGAGGTCTTCATTGACCTGTGTCGACAGATTATACGGAAGGACCTC

CAGGGAAGTTCGACCAGCGATTATGATGCTGCCGCACGTAAACGCGAGG

GTCAAACCCGACAAGACCGAAAGCGAGAGAGAAAACGACAAGTGCGGCG

AAAGGGTCCTTGTGTCATTCTCTAA

Figure 21:
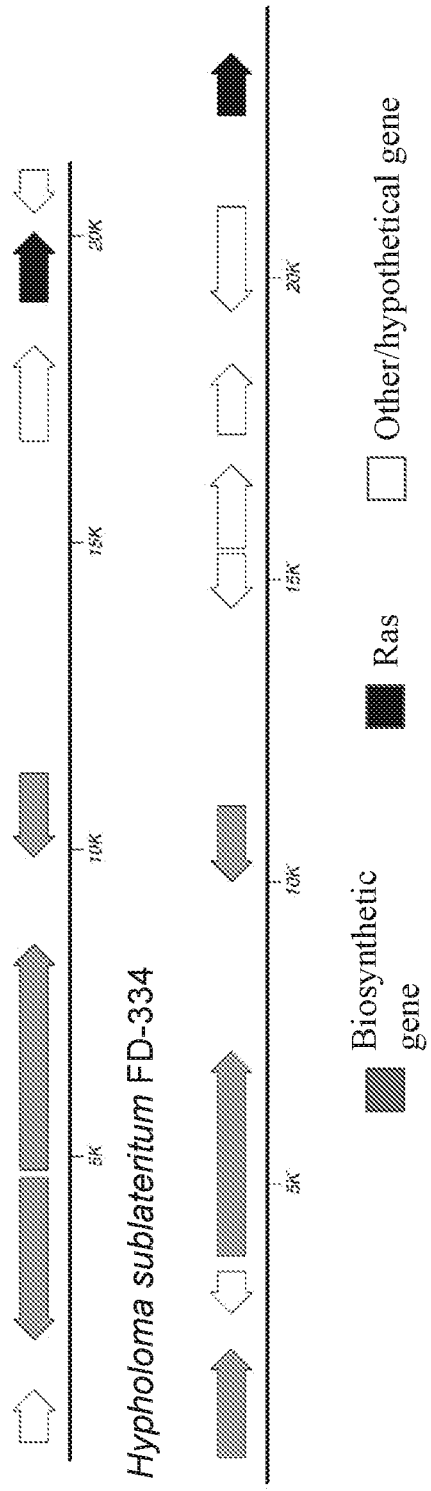
FIG. 21 depicts example biosynthetic gene clusters related to Ras, e.g., from *Agaricus bisporus* var. *burnettii* JB137-S8, *Agaricus bisporus* H97, *Coprinopsis cinerea okayama*, *Hypholoma sublateritum* FD-334. Illustrated Ras homologs are indicated in black.

FIG. 21: *Agaricus bisporus* var. *burnettii* JB137-S8. Ras ETaG sequence.

ATGGCAAACAACGCTGCGTCCAGAGTATGTCCTCCCCACAAACCACCCT

CAGTTGCCTGGCTTATGCTCTATTTCAGGCTGCTCAGGCCCAGTTCCTG

AGAGAATACAAGCTCGTAGTGGTCGGAGGAGGAGGCAAGTGCTACCCGC

CCTTACAAGCTAGCAAGTCCTAAAGTCGTGTACAGGTGTTGGAAAATCT

GCATTGACTATCCAATTCATTCAAAGCCATTTCGTGGACGAGTACGACC

CAACTATCGAGGGTGAGCTTCTTTCTCACCAATCAATCCCCTTCCAGGT

TATGACATTTCGGAACATTTGTGCTAACATTCTCGTCTTAAAACAGACT

CGTACAGGAAACAATGCGTCATTGATGAAGAGGTCGCCCTTCTCGATGT

CCTGGATACCGCTGGTCAAGAAGAATATGGGTCAGTGTGCTCTCCTGAA

TAAATTCCGAAGCAGTCCCCGATTTTTTTCCTTTCGTCTCGTGATTCG

ACTATGAAAATGGTCTTCCACGAGGCGAAGCTTTCATTTCCCGGCATAA

TTCAGTTATACGACCCTGGATCTAACCCTATATGTACTTATTTTCCAGT

GCCATGCGGGAGCAATACATGCGTACTGGGGAGGGATTTCTTCTCGTCT

ACAGCATCACCGCGCGTAGCTCCTTTGAAGAAATCAACCAGTTTTACCA

GCAAATTTTGAGGGTCAAAGATCAAGATTCTTTCCCTGTTATTGTCGTT

GCAAACAAGTGCGATTTGGAATATGAACGCCAAGTTGGTATGAACGGTA

TGTTATCAAACCTTGGAGTATATCAGGGCCCAGTAGTGACGCAACCTA

CAGAGGGCCGAGATCTCGCGAGACATTTTGGCTGCAAATTCATCGAGAC

GTCTGCCAAACAACGAATAAACGTGGATGAAGCTTTCAGCAATCTTGTT

CGTGAAATCCGAAAATATAACAAGGTCGGTTTTCCGCATCACACGCAGA

GATTTTACAAACTCATTGGTGCTTTTATAGGACCAACAAACAGGCCGCC

CTCTCCACGGCAGCGGTGGTGGAGCCGGCGGTTATGGTGGCAAGGACCA

CAATGACGATGGAGGTGCTGGCTGCTGCGGCGGTTGCGTTATTCTTTAA

*Agaricus bisporus* H97. Ras ETaG sequence.

ATGGCAAACAACGCTGCGTCCAGAGTATGTCCTCCCCACAAACCGCCCT

CAGTTTCTTGGCTTATGCTCTATTTCAGGCTGCTCAGGCCCAGTTCCTG

AGAGAATACAAGCTCGTAGTGGTCGGAGGAGGAGGCAAGTGCTACCCGC

CCTTACAAGCTAGCAAGTCCTAAAGTCGTGTACAGGTGTTGGAAAGTCT

GCATTGACTATCCAATTCATTAAAAGCCATTTCGTGGACGAGTACGACC

CAACTATTGAGGGTGAGCTTCTTTCTCACCAATCAATCCCCCTCCAGGT

TATGACATTTCGGAACATTTGTGCTAACATTCTCGTCTTAAAACAGACT

CGTACAGGAAACAATGCGTCATTGATGAAGAGGTCGCCCTTCTCGATGT

CCTGGATACTGCTGGTCAAGAAGAATATGGGTCAGTGTGCTCTCCTGAA

TAAATTCCGAAGCAGTCCCCGATTTTTTTCCTTTCGTCTCGTGATTCG

ACTATGAAAATGGTCTTCCACGAGGCGAAGCTTTCATTTCCCGGCATAA

TTCAGTTATACGACCCTGGATCTAACCCTATATGTACTTATTTTCCAGT

GCCATGCGGGAGCAATACATGCGTACTGGGGAGGGATTTCTTCTCGTCT

ACAGCATCACCGCGCGTAGCTCCTTTGAAGAAATCAACCAGTTTTACCA

GCAAATTTTGAGGGTCAAAGATCAAGATTCTTTCCCTGTTATTGTCGTT

GCAAACAAGTGCGATTTGGAATATGAACGCCAAGTTGGTATGAACGGTA

TGTTGTTAAACCTTGGAGTATATCAGGGCCCAGTAGTGACGCAACCTAC

AGAGGGCCGAGATCTCGCGAGACACTTTGGCTGCAAATTCATCGAGACG

TCTGCCAAACAACGAATAAACGTGGATGAAGCTTTCAGCAATCTTGTTC

GTGAAATCCGAAAATATAACAAGGTCGGTTTTCCACATCACACGCAGAT

TTTACAAACTCATTGGTACTTTTATAGGACCAACAAACAGGCCGCCCTC

TCCACGGCAGCGGTGGTGGAGCCGGCGGTTATGGTGGCAAGGACCACAA

TGACGATGGAGGTGCTGGCTGCTGCGGCGGTTGCGTTATTCTTTAA

*Coprinopsis cinerea okayama*. Ras ETaG sequence.

ATGCCTGAGGTGATGAATGCTATGTACGCCACGAAAGGCGGTATCTTCG

ACGTCAGCGAGAATGATAAGGTTTGGCGTTTGCAGTGTTTCAAAGCTGG

CCTCTGTTGTGTTGGAGAATACTCGGATGCTGATATACATATGGTTTAT

CGAATACAAGTACGCGTATAAGGAAAGCTGGGGTAGACAAGGGACTATA

GCTGGATCTTAACTCCCAGGAGGGGACGACATGAGAGAATGCGGTCTAC

AGCAATTCTGATGCTCGAAAATCCATCAGCAGAGGTCAACCTTGGGTTT

CTAGCGAAAAGAAGGGAGATAGGAAGCCCGGAATATCAAAACACGCGTC

GGATTGTGGTCCAAATTGAAAAATGACCGAGAGCCTCGAGCTCGTGTCG

CGAGATGTTTGCACTTGAGATTTAAACTCCGCTGATGATGGCCTTTGA

AGTGAGTTTGGTTACGATGTTTAGAGGAACCCAGTCGCCCCCTGCTCCC

GCTCAACTCCCTAAATACCCTTCCTGACCATCTTCTTTCTTTCCCAAAT

CTTTTTCTTCTCTTTCAACAGATTTCATTTCTGAAGCATGGCTGCCAGG

GTCCGTCAAATCCCACAGTCTGCACCGTGGAACCTCAGCAAACTCACAC

AGCGTCCAACAGGCTCAGTTCTTGAGGGAGTACAAGCTCGTCGTCGTAG

GTGGTGGTGGTATGTTGCACAGCTCTTAGAACGGAATGTAGTCTCACCT

GTGGTGCCCCAGGTGTTGGAAAGTCGGCCCTGACTATTCAGTTCATCCA

ATCCCACTTCGTGGATGAATATGACCCGACTATCGAAGGTCCGTATAAC

AAGGCCTTCTCTCGCAAGGATGCAATAGCTTATGCTTATTCGACACAGA

CTCGTACAGAAAACAGTGCATCATCGACGACGAGGTCGCACTCCTCGAC

GTTCTCGATACCGCCGGACAGGAAGAGTATGGGTGAGTACCCGCGCTGC

ACCCCTCTATTTTCCACCGAATGCTTCGTGGACAGCCCAACTTTTGATC

CTCGTATCCCATACCACCGCTTTCCTTGTTCCCGGAATCTTTGCATCAC

CACCCTCTCCACCTTGCCCTCTTCTTCGGGACGTTCCGTGATTAACACAC

-continued

ACCTACAGAGCCATGCGGGAGCAATACATGCGCACGGGCGAAGGCTTCC

TTCTCGTCTACTCTATCACCTCCAGAAACTCGTTTGAGGAAATCAGCAT

TTTCCACCAACAAATTTTGCGAGTCAAGGACCAGGATTCCTTCCCCGTC

ATTGTTGTGGCTAACAAGTGCGATCTCGAATATGAACGTCAAGTTGGCA

TGAACGGTGTGTAGTCCATCTTTATGTCCCTTGCCGACATGACATGAAC

AACGTATTGCAGAGGGGCGTGATCTCGCCAAACACTTTGGTTGCAAATT

CATCGAAACCTCGGCCAAGCAACGAATCAACGTCGACGAGGCATTCAGC

AACCTCGTTCGGGAGATTCGCAAGTCAACAGGGTGAGCAATCCTCTCTT

CCAAGGTATTCTGACTAGCATTCAAACTGTCTCATGCCCCCAGGAACAA

CAAACCGGTCGTCCTGCCATCGCAGCAGGTGGAGGTGGTCCAGCCGGCT

CCTACACCCAGGACAGGCACCACGATGAGGCACCTGGATGCTGTGCCGG

ATGTGTTATTGCCTAA

*Hypholoma sublateritum* FD-334. Ras ETaG sequence.

ATGGCTGCTAGGGTACGTCCCTTCACATAACTAGCCAACGTCGCGTAGC

TCATGCCCTCTCAGGCTCAGTTCTTGCGAGAATACAAGTTGGTGGTGGT

GGGCGGAGGAGGTCAGCAAATCCTGGCGCCATTTCCCGGTCTTTCTCCT

GCTCACAGTTTCCTTCAGGTGTCGGAAAGTCTGCTTTGACTATTCAGTT

CATTCAAAGCCATTTCGTTGACGAGTACGATCCCACCATCGAGGGTGAG

AGTTTCGTGCTTCCAGTGCCGCCGCGACGCTGACCGAAGTCAAGATTCG

TACCGTAAGCAATGCGTAATCGACGAGGAGGTTGCTCTCCTCGACGTTC

TGGACACTGCTGGTCAGGAGGAGTACGGGTACGTGTCTGTCTTTACCAT

TAACATTGTCCTCCCCCTGTTCTTTTTTGGCTCGCGCCTCGAGGCGCGT

TCTTGCTCTGGTGCTATTCTTATCATGGCTGTTCTCTGACGGAAATACG

TATAGTGCTATGCGCGAACAATACATGCGTACCGGCGAGGGTTTCTTGC

TCGTCTACTCCATTACATCCCGCGACTCCTTCGAGGAAATAAGCACATT

CCACCAACAGATTCTGCGGGTCAAGGACCAGGACTCGTTCCCCGTTATC

GTTGTTGCGAACAAGTGCGATTTGGAGTACGAGCGCCAGGTTGGCATGA

ATGGTACGGCAGTAGACCACCAGGCTGGAAGATGCTAATCAACTATCTC

TCTCAGAGGGCCGTGACCTTGCCAAGCACTTCGGTTGCAAGTTCATCGA

AACGTCAGCCAAGCAGCGGATCAACGTCGATGAGGCTTTCAGCAACCTT

GTTCGCGAGATTCGGAAGTATAATAAGGTTAGTACGTTATGTTATTCTA

CCTCTCCCTATCTGACAGATATTGTCCACCAGGAACAACAAACTGGTCG

CCCGGCCCTTGCCGGCAATGGAGGAAGCACTGGCGCATACGATGGGAAA

GACCAGCACGATGATACTCCTGGGTGTTGTTCCGGCTGTGTTGTCCTCT

AA

Figure 22:
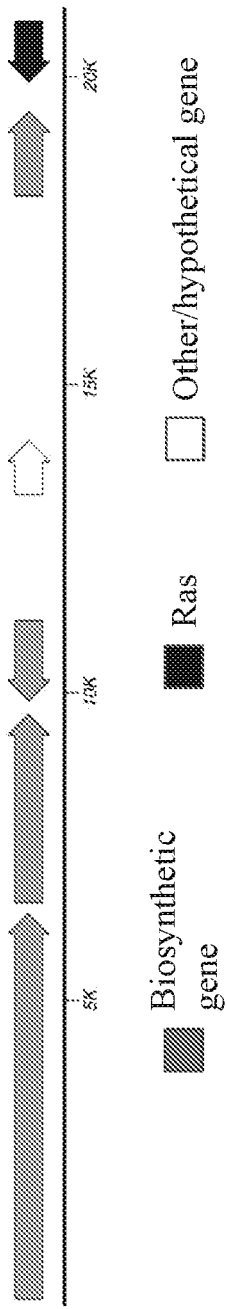
FIG. 22 depicts example biosynthetic gene clusters related to Ras, e.g., from *Sistotremastrum niveocremeum* HHB9708 and *Sistotremastrum suecicum* HHB10207. Illustrated Ras homologs are indicated in black.

FIG. 22: *Sistotremastrum niveocremeum*. Ras ETaG sequence.

ATGTCGAGAGTGAGTATTTCTGTTTATTGCGGCTCTATCTTGATCTCAC

TCGTCGCTAGTCTGCTGCTCAGGCTTCGTTCCTTCGCGAATACAAGCTC

GTCGTCGTCGGTGGTGGTGGTATGAGCCTTGTCTCTCGTTCTCTGCAAT

CAAAATCTCACTCGCTTTTCTCTTGTGCTGCCTAGGTGTTGGCAAATCC

GCTCTGACCATTCAATTCATCCAAAGTCATTTCGTTGACGAGTATGACC

CTACTATCGAAGGTCAGCCGACCGCTAGGCAACCATTATCTGATCAAAC

AGCTCATCTCGCACTCGACAGATTCTTACAGAAAGCAATGTGTCATCGA

TGATGAAGTTGCCCTTTTGGATGTGTTAGATACCGCTGGGCAGGAAGAA

TATGGGTGAGCTCGTCTCGCAGCCCGATTCCCACGCTTATTGCTAACAC

GACATCGGCAGCGCAATGCGAGAACAGTATATGCGAACGGGAGAAGGAT

TCTTGCTTGTCTACTCGATAACGTCGCGGAACTCTTTCGAAGAAATCAG

CACTTTCCATCAGCAAATTCTTCGAGTAAAAGACAAGGATGCGTTCCCG

GTTATCGTGGTAGCCAACAAGTGTGACCTTGAATATGAGCGACAAGTCG

GCATGAACGGTGCGTTTTTAGTGTTGTTTCAATCACATTGTGACTCAT

CCTTCGTCAGAGGGCCGTGACCTGGCCAAGCACTTCAACTGCAAATTTA

TCGAGACCTCGGCGAAGCAGCGAATCAACGTTGATGAGGCCTTTTCGAA

CCTTGTTCGAGAGATTCGCAAATTCAACAAGGTATGTAAGCCCAAACCC

GACGGAACTCCCGGCCTGATCTCTTTACAGGAACAACAGACCGGACGTC

CTGCGACCATGGCTCCGAGCGGCCCTGTGGGTGCATTCGGTGGTCCCCC

CGGCATGGAAGATGGACCTCATGACGCTGGTTGCTGCTCTGGATGTGTC

GTTGTATAA

*Sistotremastrum suecicum*. Ras ETaG sequence.

ATGTCGAGAGTGAGTATTTCTGTTTATTGCGGCTCTATCTTGATCTCAC

TCGTCGCTAGTCTGCTGCTCAGGCTTCGTTCCTTCGCGAATACAAGCTC

GTCGTCGTCGGTGGTGGTGGTATGAGCCTTGTCTCTCGTTCTCTGCAAT

CAAAATCTCATTCGCTTTTCTCTTGTGCTGCATAGGTGTTGGCAAATCC

GCTCTGACCATTCAATTCATCCAAAGTCATTTCGTTGACGAGTATGACC

CTACTATCGAAGGTCAGCCGACCGCTAGGCAACCATTATCTGATCTAAC

AGCTCATCTCGCACTCGACAGATTCTTACAGAAAGCAATGTGTCATCGA

TGATGAAGTTGCCCTTTTGGATGTGTTAGATACCGCTGGGCAGGAAGAA

TATGGGTGAGCTCGTCTCGCAGCCCGATTCCCACGCTTATTGCTAACAC

GACATCGGCAGCGCAATGCGAGAACAGTATATGCGAACGGGAGAAGGAT

TCTTGCTTGTCTACTCGATAACGTCGCGGAACTCTTTCGAAGAAATCAG

CACTTTCCATCAGCAAATTCTTCGAGTAAAAGACAAGGATGCATTCCCT

GTTATCGTGGTAGCCAACAAGTGTGACCTTGAATATGAGCGACAAGTTG

GCATGAACGGTGCGATTCTAGTGTTGTTTCTGTCGATATTGGGACTTAT

CCCCCTTCAGAGGGCCGTGATTTGGCCAAGCACTTCAACTGCAAATTTA

TCGAGACATCGGCGAAGCAGCGAATCAACGTTGATGAGGCCTTTTCCAA

CCTTGTTCGAGAGATTCGCAAATTCAACAAGGTATGTAAGCCCAAACCC

GACGGAACTCCCGGCCTGATCTCTTTACAGGAACAACAGACCGGACGTC

*-continued*
```
CTGCGACCATGGCTCCGAGCGGCCCTGTGGGTGCATTCGGTGGTCCCCC
CGGCATGGAAGATGGACCTCATGACGCTGGTTGCTGCTCTGGATGTGTC
GTTGTATAA
```

Figure 23:
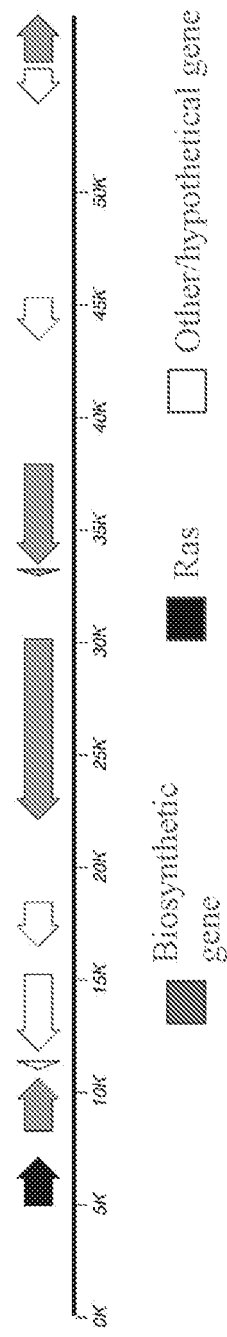
FIG. 23 depicts example biosynthetic gene clusters related to Ras, e.g., from *Talaromyces leycettanus* strain CBS 398.68. Illustrated Ras homolog is indicated in black.

FIG. 23: *Talaromyces leycettanus* CBS 398.68. Ras ETaG sequence.

```
ATGCTGGAAGTGCTAGACACAGCGGGCCAGGAAGAGTACACCGCACTGA
GAGACCAGTGGATCCGCGATGGTGAAGGGTTCGTTCTCGTCTATAGCAT
CACATCGCGAGCGTCGTTCGCCCGCATACCCAAGTTCTACAATCAGATC
AAGATGGTTAAAGAATCGGCAAGCTCCGGGTCACCCGCTGGAGCCAGCT
ACTTGACGTCGCCGATCAATTCTCCCTCGGGACCCCCGCTTCCTGTGCC
GGTAATGTTGGTTGGCAACAAGAGCGACAAGGCGATGGACCGCGCCGTC
TCTGCGCAGGAAGGCCAAGCTCTTGCCAAGGAGCTGGGGTGCGAATTCG
TCGAGGCTTCCGCCAAGAACTGTATCAATGTCGAAAAGGCTTTCTACGA
CGTCGTGAGGATGCTTCGGCAGCAGCGACAACAGCAACAGGGAGGACGG
GCGCAGGAGCGGCGACCCGCCGCTTTCGGATCAGGGCCAATGCGCGATC
GGGACGCCGGTCCCGAGTACCCAAAGTCGTTTCGTCCGGATCGATCAAG
GCATCGCAATGGCCTCAAATGCGTTATCCTATGAGCTCCCCCCGATGAG
TGTTCCGATCGGCGGATCTTTCCAGCTTCTGACCTCCGCTTATTCATGA
CCGTTGCTCTCTAGAATGGATGGTGTCTAGCTCCGTGTTTCTCTTTCTC
GGAGCGTGTGAGCGAGCTTGAGGACAGTCGTTCCACTTGTGCCCCCTCC
TATCCGCCGCAGGCCCTTGTCGCTGCCGCTTTGCGGACCGCTCGTTTTG
TCTACGTTGTACTCGAAAGCACGGCCTCTGCTTTCGTGGAAGTCTCCCT
TTATGCCAGCTTTGGGTGCGGTGGTCGATATGCAGATACTGTGTTCTAT
GCTCGCTGCATGCGATTCAGAGGCGTCTTGATTCCCCGTGTCAGTATGG
GGTGTTCTCGCTATTCAGGGAATCATCTGAAACCAATTTTTCTCATCCG
TTCTGTTTTTGGGAATCGGAACACGGGGGGGATGTCTGGAAATCTGGAC
CTATAACTATAGAAATGTTTCTCACCACCTTTCTCACTCAACCCTCTTG
ATGAATATCCGCCCGGCGTCTTCTACTACTTCCTACCGTCTACTACCAC
CAATCTCTATTCTTCTTACCACCCACCTTCTGAGCCACTTCTTACACAT
CATTCTCGTTTGGTTTGACAGCAAAGCGGGGAGAGTTCGAAGGACAGAT
CCCATGCAGGATTGGAGGACGAGAGGGGAAGAGTCGAAGGGAGAAAAAT
AATTAAAAAAAGAAAGGTGCGGGGGCAGAAGGAGGCAGGTTTGGTTGA
GAGTTGCGAATCGGTCCTGTCGCAGTCAAGTCCCAAAAAAGAAAAGATC
GCAGTCGGCGCATTAGCAGGCATTTTGATACGATGATACCCTACAGCCG
AGCTTCGAGTTTTTGTGTTCCTTTTCCTTTTTTGCAAATGCTGATTTAA
AAAAATAACAATAGAGCTACATACTGAATGTGGATTTTTTTGACCTCTC
ATCTTTTTGTTGCAGGGATGACCGCCAATTGGTAAATTCATCCCCAGTC
ATAATCCGAGCGCAGGATGCATGAACTCCAGTACCTCATCATATCGCCT
GCACGTTCAAGTTCCATCAATCATTCGGCGGCGCCTACTCTGTACGACT
AAGTCTACGGAGTTTGTTCTTGTTGCGGGGAAGGAAGCGAAAGCCACGA
```

*-continued*
```
CTCCAACAAACAAACTCAGGGTGAATTGAATCCTCAGTTTCTACTCTGT
AGCCGAAGAGCCATCATTACCATTCAGGGGAAGAGCCTAAAGAGCTTGC
GAGGTTGGGCTGAGCTGCTGTGCAGTGAGCAATATATTTGGTCGATGTT
TTGGATACGTTATCTGGAATGCGCAGATGCAGTGGTTATGCATATCCTC
ACGTACTCGATTCTGATGATTCACGGGACCATACGGAGTCGATACCGAG
ACTCTCGCTACAAACCTGTCAATTGATATCGTGTACAGAGTACCGGAGC
CGAGACTGGGAAATAGCACAGTCTCAGTCTCAGGTAGCTATCGATCAAT
TTGACAAGGTTAGAAGTATCTCGCTAGTAATTGCCAGATGATTCATTCC
CGGTTGAAAACTTTTCCATTGGCCTTCTTCGCTTAG
```

Figure 24:
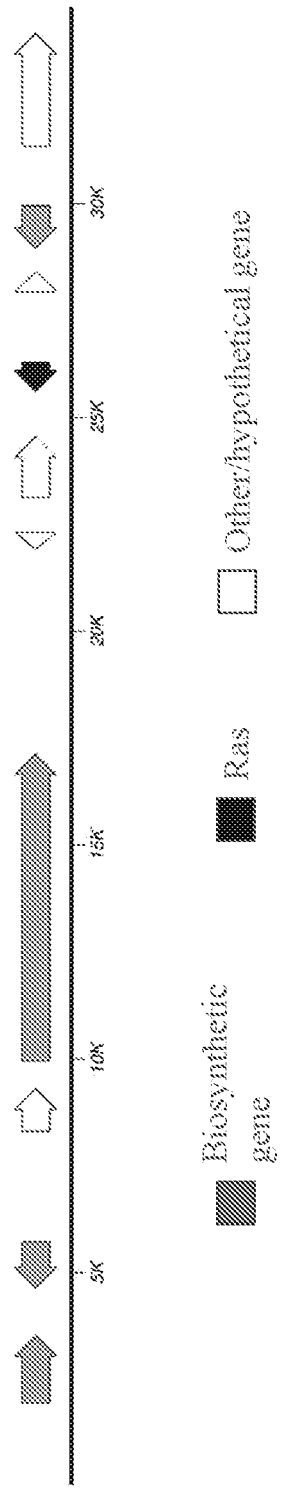
FIG. 24 depicts example biosynthetic gene clusters related to Ras, e.g., from *Thermoascus crustaceus*. Illustrated Ras homolog is indicated in black.

FIG. 24: *Thermoascus crustaceus*. Ras ETaG sequence.

```
ATGACCCAACAATCGAAGGTTGGTCACCGTTAAGCAAACCACGATGGGAG
CGTCCCGACCATGATGGCTCATTAGATCTCTTCTTCTCCAGACTCGTACC
GCAAGCAGTGTGTTATTGACGATGAGGTCGCCCTGTTGGACGTCCTGGAT
ACCGCCGGCCAGGAGGAATACTCAGCCATGCGAGAACAGTACATGAGAAC
GGGAGAGGGGTTCCTTCTGGTGTACTCTATAACTTCGCGTCAGTCGTTCG
AGGAAATCATGACCTTCCAACAACAGATCTTGCGAGTCAAGGACAAGGAT
TATTTCCCCATCATTGTCGTCGGCAACAAGTGTGATCTGGAGAAGGAGAG
AGTGGTCACGCAAGAAGGTATGTCTTTAAGCTCTCCGTCGGCTTTTGAAA
CTTGGCTGGAGTGCCTTGCTAATCACATTACCGCTTCTCAACAGAGGGTG
AGGCTCTCGCGAAGCAATTCGGCTGCAAATTCCTGGAAACCTCGGCGAAG
TCGCGTATTAATGTTGAAAACGCGTTCTACGAACTTGTGCGTGAGATCCG
CCGCTACAACAAAGAGATGTCATCCTCGTCCGGTGGCGGTGCGGGCGCGC
GCGCCCCTGAGGGCAAGATGGATGTTAATGACCCAGGCGAGAGCGCTGGC
TGCTGTGGAAAGTGCATTGTTATGTAA
```

Figure 25:
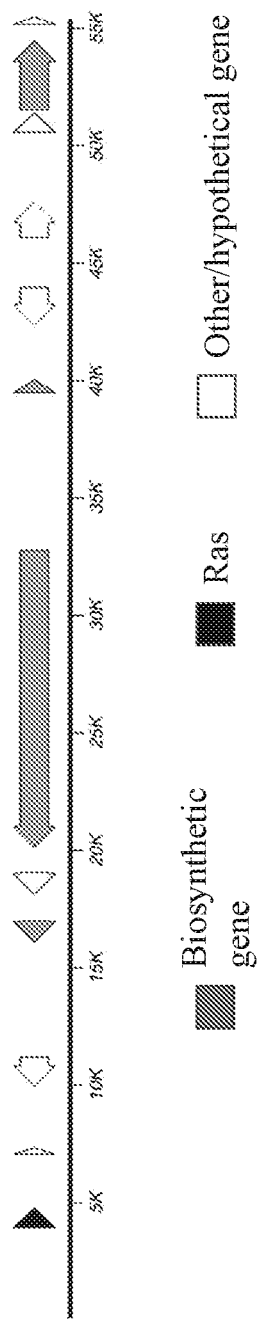
FIG. 25 depicts example biosynthetic gene clusters related to Ras, e.g., from *Bipolaris maydis* ATCC 48331. Illustrated Ras homolog is indicated in black.

FIG. 25: *Bipolaris maydis* ATCC 48331. Ras ETaG sequence.

```
ATGTTCTTGCCTCAACTCTACTCCCTCAACCCTGCCTTGGCTGCCAAACA
TGCTGATCCTCTTGCTCCTACAGCCCAGTTTGTGCAAAACGTGTGGATAG
AGAGCTATGATCCCACCATCGAGGACTCGTACCGAAAGGTCCTCGAAGTA
GACGTGCGTACACGACACTCTTACTAGCCGCGTTTTTTTCACTGACCCAC
TCTCCCTCCCAGGGCCGTCATGTCATTCTCGAGATCTTGGATACTGCCGG
CACAGAGCAGTTTAGTAAGTGATTACATACATAGCCCCACCCCACGTGGA
CCCAAGACTAACACGACAATAGCTGCCATGAGGTAGAGTTTCCTACTACC
CCCTTACTCGGTAAACATCAAAACTTACACGGATGCAGAGAACTGTACAT
GAAAACGGGCCAAGGATTCCTTTTGGTCTTCAGCATCACATCAGAATCTT
CCTTTTGGGAGCTTGCCGAGCTGCGTGAGCAGATACGACGCATCAAGGAA
GACAGCAACGTACCCATGGTTCTCATTGGCAACAAGTCGGACCTAGAAGA
CGACCGTGCCGTGCCGCGCCCACGAGCATTTGCCATTTCGCGTGAATGGA
ACGTTCCTTATTTCGAAACCAGTGCTCGAAGGAGAGCCAATGTCGACGAA
GCCTTTGTCGACCTCTGCAGGCAAATCATCCGCAAGGATCAGAACGAACG
```

-continued

AAACCGCATGGCCCCACCGGATTCCCCGAGGCCTGGCGGTCCCAGGAGCA

GAACTCACACGGGACGGCCAAAGCGCAAGGCTCACCGGCCCCATTGTACC

ATTCTTTAA

Figure 26:
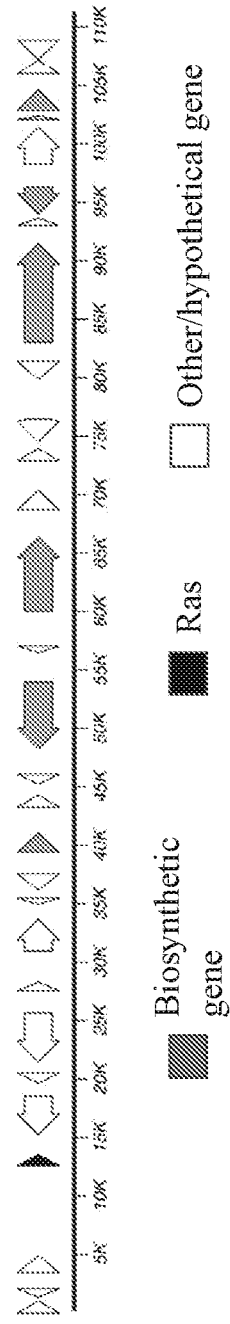
FIG. 26 depicts example biosynthetic gene clusters related to Ras, e.g., from *Colletotrichum higginsianum* IMI 349063 (CABI). Illustrated Ras homolog is indicated in black.

FIG. 26: *Colletotrichum higginsianum* IMI 349063. Ras ETaG sequence.

ATGGCGTCCAAGGTTCGTCGTCGCCACCTCCCGTTTCCCTTCATTTCTTT

TGCCGCCTCGTCGCTCCATCGCTCCATCGCCCCATCGATCCGTTGCTAAC

CAGTTGCCATCTCGCAGTTTCTGAGGGAGTACAAGTTGGTCGTCGTCGGC

GGCGGTGGTGTCGGTAAATCCTGCTTGACCATCCAATTGATTCAGAGCCA

CTTTGTCGACGAATATGACCCGACGATCGAAGGTGCGTCGTCCCGAACTT

CTTGCTCCACCGTTCGATGCGACGGCTTGAATCAATCGCATGCTAATGT

GGATCTCACCCATTTCAGATTCCTACCGCAAGCAGTGCGTCATCGACGAG

GAGGTCGCTCTACTCGATGTCCTCGACACGGCCGGTCAGGAGGAGTACTC

CGCCATGAGGGAGCAGTACATGAGGACGGGAGAGGGTTTCCTTCTGGTTT

ACTCCATCACTTCGCGACAGAGCTTCGAGGAGATCACCACATTCCAGCAG

CAGATTCTGAGAGTAAAGGACAAGGACTACTTCCCCATGGTCGTCGTCGG

CAACAAGTGCGATCTGGAGAGCGAGAGAGAAGTCACACGACAAGGTATGA

TTCTGATTCCTGCTGTGCCGCGACACCGCATGAGGCGGCTCCTTTCGAGG

CCCAGGCCCGGTGTGGATTCATTGATGGAATGAAAAGTAGCTGACATCAT

TCACTCGTGCGCGCTACAGAGGGAGAGGCCCTTGCCAAGTCATTCGGCTG

CAAGTTCATCGAGACGTCGGCCAAGTCTCGCATCAACGTCGACAAGGCTT

TCTATGATATTGTCCGAGAAATCCGTCGGTACAACCGCGAGATGCAGGGC

TACTCTACCGGCAGTGGCGGCGCCTCGGGCATCAACGGCCCCCCGAAGCC

CATGGACGTCGAGAACGGCGAGCAAGAGGCAGGCTGCTGCTCCAAGTGCG

TACTAATGTGA

Figure 27:
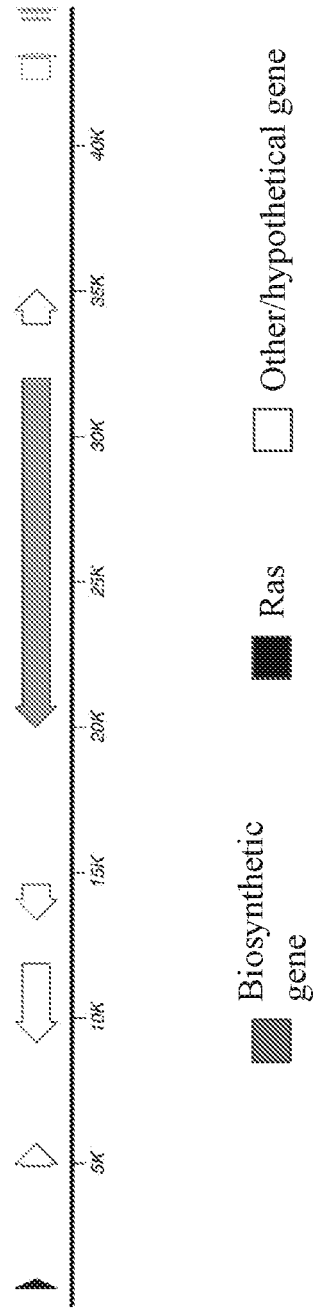
FIG. 27 depicts example biosynthetic gene clusters related to Ras, e.g., from *Gyalolechia flavorubescens*. Illustrated Ras homolog is indicated in black.

FIG. 27: *Gyalolechia flavorubescens*. Ras ETaG sequence.

ATGGCTTCAAAGGTAAGTCCATCTGTCTCTTTAGAGTATTCTCATTGCTC

TTTGCTACCGAGCTTCTCCATGGACGCTGACCCTTACCTGCTCAAGTTCC

TACGGGAATACAAGCTCGTCGTCGTTGGCGGAGGAGGTGTGGGCAAGTCC

TGCTTGACCATCCAGCTCATCCAGAGTCACTTCGTCGACGAATACGATCC

CACCATTGAAGGTAAATAGATTCGTCCTATCCACCCATTGCGCTTTTACT

GATCGAAGCGATTTGCAAGACTCCTACCGGAAGCAATGCGTCATCGACGA

AGAAGTCGCCTTACTCGATGTACTAG

Figure 28:
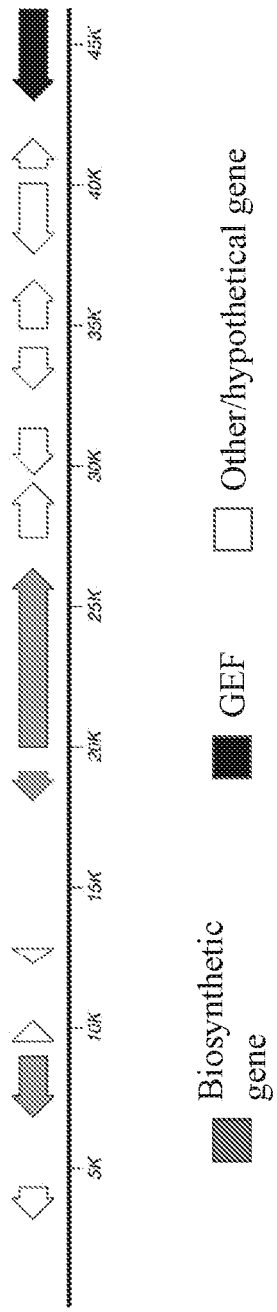
FIG. 28 depicts example biosynthetic gene clusters related to RasGEF, e.g., from *Penicillium chrysogenum* Wisconsin 54-1255 and *Lecanosticta acicola* CBS 871.95. Illustrated RasGEF homologs are indicated in black.

FIG. 28: *Lecanosticta acicola* CBS 871.95. RasGEF ETaG sequence.

ATGGAGCTCCCTTTCGAGAACCCGACCGCAACAACTGAACCAGGCCCGCG

AGATCGAAATAATTTCTTTGTCCCCGACCAGACACGGCCACCTCCAGAGC

TGATGGCGCGTGGCTTTGAGCGGGATGAGGACGAGTACGATGGATCTGCA

TCGGAGGCAGAAGGAGAGTCACTGATGTTAGGCTCGCATGACTCGATTTC

TCGCCGACGCCAGTCCGTGATGGATGGAGTATCCCCTGCCACGTCCATGG

ATTCCTTGTACGCCGCAGGATCTAAAGATTTCAAAACGCCGCAGCCGCCG

AGCAAGAGCCCGCAAAAGTCACACAGCCTCGGCGGAAACAGTACCAGCAC

ATCTGTGACCGAAAGCTTTTCCAGACCTTCTATTTCCTCCAACCCCCCTC

AACACTTTGTCGACGATGGCTTCGCACCGCCAATCACCTGGCCTTTGCTT

GTCGATAATATGCGGTACGCCGTGGAAGCCTATCGCCAGGTGCTTTTCAA

CGGTGAGCGTGCAGAGTACGTAAGAAAGGCCGAGGACATATCTGACCATC

TTCGCATGCTGCTGGCTGCTGGATCTGACACGACGGATAACCACTCTGGT

AACCCATCTATCATTTCCACAAACAAGGCGCTATATCCTTACTTCCGGGA

CATGATGTCTAAGTTCTCGAAGCTGGTTCTTTCATCACATATTGCCGCCG

CTGATTGGCCTGGTGCCGACTCGGCCAATAAATGTTTGCAGGAGGCCGAT

GGAGTTATGCAAGGCGTGTATGGCTATGTGCAAGTGGCTCAACATCAGCG

CGGCGATGCCATCCATCGCATCGTGCCTGGCTTCGTCAGCGGCAGCTCTT

CGGGTGGTAGCTGGCAGAACAACGGTGTTTCCTTGAATACTTCAGGCCCG

ACATCATTCCTCGTTCCGGATGGAGGGGACTCGCGAGTAGAGCCATCGGT

CTCTCTTGACACCGCCTTTTTGGATTCAATCGACATCCTCAGAAGATCTT

TTGTTGGTAGTATTCGGCGACTAGAAGAACGGCTGGTTATAAACCGGAAT

ATCGTTACAGTGGAGGAACATGGAGACATTGCCGATGCGATCTCAGCTGC

TGCAATCAAGGTGATTGAACAGTTCCGCCCATGGATCTCCTCGGTGGAGT

CGATGAATTTAGCTCCGTTGGGAACCAGCTTCCAGAACCCCCAGCTAGTA

GACTTCAGCTTGCAAAAGCAGAGAGTCTACGATGCTATTGGAGATTTTGT

CCTGAGCTGTCAAGCAGTCTCTGCCCCTCTGGCTGATGAGTGGGCAGAGC

TCCGTGGTAATTCTCTCGACGATCGTGTGAATGCCGTGCGAGGCATCGTT

AGACAGTTGGAGAACTATGTCTCCCAGATTGGCTTCTCATTGTCGCTGCT

CCTCGAGCAAATCCCCACCGAACCAGCATCATCTCTAAGACGGGATAGCC

GCCAAGAAGCGGAAGATGAGTCGTACAAGATAATGCATAGCCGAGGCGAG

TCCAAGGCCAAGATTGCCACAGAGTCAATCGGGATTCCGTCCTCCTACGC

TCCTGAAAAGGAAAGTGGCACAGATAAAGTACGAAGAAATATGGACAAGG

CACAACGTTTCTTTGGCCAGGCACCCCCAACGGCTATCACCCGAGAGCCA

ATCCGTGAGCCAGTCCGTGAGCCCGAAGAAACTCCCTGGTTCTTGAAAAT

GGCCCATGAAGGCGAAGTGTTCTACGATAACAAGGGAGACTTGCCCATCC

TCAAATGTGGAACACTCGCCGGATTGGTTGAACACCTCACCCGCCACGAT

AAGCTTGATGCATCCTTCAACAACACATTCCTCCTCACCTATCGCTCTTT

CACTACTGCCACCGAACTATTTGAATTGCTTGTCCAGCGGTTTAACATTC

AGCCTCCATTTGGCCTGAATCAAGATGACATGCAAATGTGGATTGACCGG

AAACAGAAGCCGATTAGATTCCGTGTCGTCAACATTCTTAAGAGCTGGTT

CGATCACTTCTGGATGGAGCCCAATGATGAACTGCACATGGATCTCCTGC

GACGTGTCCATACCTTTACCAGCGACTCCATCGCTACCACGAAGACCCCA

GGAACCCCTACATTATTGGCCGTGATCGAACAACGCTTCGAGGACAAGA

TACCACTGTTAAGCGCCTTGTTCCGACTCAGAGCACCGCCGCACCAACAC

CAATCATCCCTAAGAATATGAAGAAACTGAAGTTCCTCGACATTGATCCA

ACGGAGTTTGCTCGGCAGTTGACCATCATTGAGTCGCGCCTCTACTCCAA

AATCCGGCCCACTGAGTGTTTGAACAAGACATGGCAGAAGAAGGTCGGCC

CTGATGAGCCGGAACCATCTCCCAATGTCAAGGCCTTGATTCTTCACTCG

AACCAGCTTACCAACTGGGTCGCGGAAATGATTCTCGCCCAAGGCGATGT

TAAGAAGCGGGTTGTAGTCATCAAACACTTTGTGAACGTGGCTGATGTAT

GTGTTTACTCTGCTTGCTTGACAAATCCCGGCCTCACTAACTCAATCATA

CAGAAATGTCGCCATCTGAACAATTATTCTACCCTGACTTCCATCATCTC

GGCTCTTGGAACTGCACCCATTCATCGTCTAGGTAGAACGTGGGCCAGG

TTAGCGGACGCACGTCCGCAATTCTGGAACAGATGCGCCGGCTTATGGCT

AGTACGAAGAACTTTGGCGAATACCGAGAAACCCTGCATCTCGCTAACCC

GCCCTGTATTCCATTTTTCGGTATGCGTCACGGTCATTTCAAGCAGATTC

AAGTTGTCTTGGAGTATCTCACCCCCTTGACTCTGTAGCTAACACATCTT

AGGTGTCTATCTCACGGATTTGACCTTCATTGAAGACGGTATCCCGTCTC

TAACACCATCAGAATTGATCAACTTCAATAAGCGGGCCAAGACCGCAGAA

GTCATCCGGGATATCCAACAATACCAGAACGTGCCTTACCTTTTGCAACC

CGTCGGCGAACTTCAAGATTACATCCTCAGTAACCTCCAAGGTGCTGGCG

ATGTACATGACATGTACGACCGGAGTCTGGAGATCGAGCCTAGGGAGCGC

GAGGACGAAAAGATTGCAAGGTATGCTGAAGCCACAAGCAGAGACAAGGG

CTCCTTGTTATTTGCATCCACCGTCGCTATCTTGCGATAA

Penicillium chrysogenum Wisconsin 54-1255. RasGEF ETaG sequence.

ATGGAGCTCCCTTTCGAGAACCCGACCGCAACAACTGAACCAGGCCCGCG

AGATCGAAATAATTTCTTTGTCCCCGACCAGACACGGCCACCTCCAGAGC

TGATGGCGCGTGGCTTTGAGCGGGATGAGGACGAGTACGATGGATCTGCA

TCGGAGGCAGAAGGAGAGTCACTGATGTTAGGCTCGCATGACTCGATTTC

TCGCCGACGCCAGTCCGTGATGGATGGAGTATCCCCTGCCACGTCCATGG

ATTCCTTGTACGCCGCAGGATCTAAAGATTTCAAAACGCCGCAGCCGCCG

AGCAAGAGCCCGCAAAAGTCACACAGCCTCGGCGGAAACAGTACCAGCAC

ATCTGTGACCGAAAGCTTTTCCAGACCTTCTATTTCCTCCAACCCCCCTC

AACACTTTGTCGACGATGGCTTCGCACCGCCAATCACCTGGCCTTTGCTT

GTCGATAATATGCGGTACGCCGTGGAAGCCTATCGCCAGGTGCTTTTCAA

CGGTGAGCGTGCAGAGTACGTAAGAAAGGCCGAGGACATATCTGACCATC

TTCGCATGCTGCTGGCTGCTGGATCTGACACGACGGATAACCACTCTGGT

AACCCATCTATCATTTCCACAAACAAGGCGCTATATCCTTACTTCCGGGA

CATGATGTCTAAGTTCTCGAAGCTGGTTCTTTCATCACATATTGCCGCCG

CTGATTGGCCTGGTGCCGACTCGGCCAATAAATGTTTGCAGGAGGCCGAT

GGAGTTATGCAAGGCGTGTATGGCTATGTGCAAGTGGCTCAACATCAGCG

CGGCGATGCCATCCATCGCATCGTGCCTGGCTTCGTCAGCGGCAGCTCTT

CGGGTGGTAGCTGGCAGAACAACGGTGTTTCCTTGAATACTTCAGGCCCG

ACATCATTCCTCGTTCCGGATGGAGGGGACTCGCGAGTAGAGCCATCGGT

CTCTCTTGACACCGCCTTTTTGGATTCAATCGACATCCTCAGAAGATCTT

TTGTTGGTAGTATTCGGCGACTAGAAGAACGGCTGGTTATAAACCGGAAT

ATCGTTACAGTGGAGGAACATGGAGACATTGCCGATGCGATCTCAGCTGC

TGCAATCAAGGTGATTGAACAGTTCCGCCCATGGATCTCCTCGGTGGAGT

CGATGAATTTAGCTCCGTTGGGAACCAGCTTCCAGAACCCCCAGCTAGTA

GACTTCAGCTTGCAAAAGCAGAGAGTCTACGATGCTATTGGAGATTTTGT

CCTGAGCTGTCAAGCAGTCTCTGCCCCTCTGGCTGATGAGTGGGCAGAGC

TCCGTGGTAATTCTCTCGACGATCGTGTGAATGCCGTGCGAGGCATCGTT

AGACAGTTGGAGAACTATGTCTCCCAGATTGGCTTCTCATTGTCGCTGCT

CCTCGAGCAAATCCCCACCGAACCAGCATCATCTCTAAGACGGGATAGCC

GCCAAGAAGCGGAAGATGAGTCGTACAAGATAATGCATAGCCGAGGCGAG

TCCAAGGCCAAGATTGCCACAGAGTCAATCGGGATTCCGTCCTCCTACGC

TCCTGAAAAGGAAAGTGGCACAGATAAAGTACGAAGAAATATGGACAAGG

CACAACGTTTCTTTGGCCAGGCACCCCCAACGGCTATCACCCGAGAGCCA

ATCCGTGAGCCAGTCCGTGAGCCCGAAGAAACTCCCTGGTTCTTGAAAAT

GGCCCATGAAGGCGAAGTGTTCTACGATAACAAGGGAGACTTGCCCATCC

TCAAATGTGGAACACTCGCCGGATTGTTGAACACCTCACCCGCCACGAT

AAGCTTGATGCATCCTTCAACAACACATTCCTCCTCACCTATCGCTCTTT

CACTACTGCCACCGAACTATTTGAATTGCTTGTCCAGCGGTTTAACATTC

AGCCTCCATTTGGCCTGAATCAAGATGACATGCAAATGTGGATTGACCGG

AAACAGAAGCCGATTAGATTCCGTGTCGTCAACATTCTTAAGAGCTGGTT

CGATCACTTCTGGATGGAGCCCAATGATGAACTGCACATGGATCTCCTGC

GACGTGTCCATACCTTTACCAGCGACTCCATCGCTACCACGAAGACCCCA

GGAACCCCTACATTATTGGCCGTGATCGAACAACGACTTCGAGGACAAGA

TACCACTGTTAAGCGCCTTGTTCCGACTCAGAGCACCGCCGCACCAACAC

CAATCATCCCTAAGAATATGAAGAAACTGAAGTTCCTCGACATTGATCCA

ACGGAGTTTGCTCGGCAGTTGACCATCATTGAGTCGCGCCTCTACTCCAA

AATCCGGCCCACTGAGTGTTTGAACAAGACATGGCAGAAGAAGGTCGGCC

CTGATGAGCCGGAACCATCTCCCAATGTCAAGGCCTTGATTCTTCACTCG

AACCAGCTTACCAACTGGGTCGCGGAAATGATTCTCGCCCAAGGCGATGT

TAAGAAGCGGGTTGTAGTCATCAAACACTTTGTGAACGTGGCTGATGTAT

GTGTTTACTCTGCTTGCTTGACAAATCCCGGCCTCACTAACTCAATCATA

CAGAAATGTCGCCATCTGAACAATTATTCTACCCTGACTTCCATCATCTC

GGCTCTTGGAACTGCACCCATTCATCGTCTAGGTAGAACGTGGGCCAGG

TTAGCGGACGCACGTCCGCAATTCTGGAACAGATGCGCCGGCTTATGGCT

AGTACGAAGAACTTTGGCGAATACCGAGAAACCCTGCATCTCGCTAACCC

GCCCTGTATTCCATTTTTCGGTATGCGTCACGGTCATTTCAAGCAGATTC

AAGTTGTCTTGGAGTATCTCACCCCCTTGACTCTGTAGCTAACACATCTT

AGGTGTCTATCTCACGGATTTGACCTTCATTGAAGACGGTATCCCGTCTC

-continued

```
TAACACCATCAGAATTGATCAACTTCAATAAGCGGGCCAAGACCGCAGAA
GTCATCCGGGATATCCAACAATACCAGAACGTGCCTTACCTTTTGCAACC
CGTCGGCGAACTTCAAGATTACATCCTCAGTAACCTCCAAGGTGCTGGCG
ATGTACATGACATGTACGACCGGAGTCTGGAGATCGAGCCTAGGGAGCGC
GAGGACGAAAAGATTGCAAGGTATGCTGAAGCCACAAGCAGAGACAAGGG
CTCCTTGTTATTTGCATCCACCGTCGCTATCTTGCGATAA
```

Figure 29:
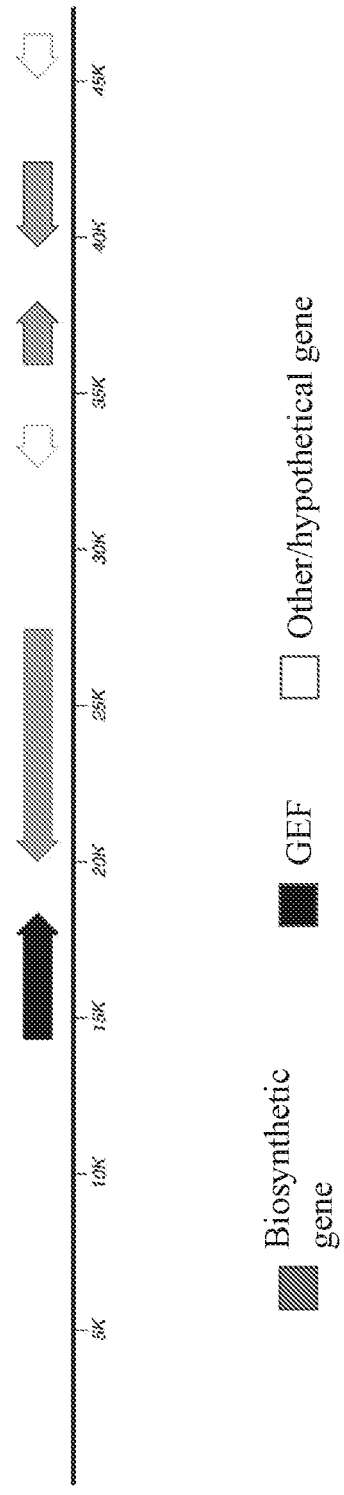
FIG. 29 depicts example biosynthetic gene clusters related to RasGEF, e.g., from *Magnaporthe oryzae* 70-15. Illustrated RasGEF homolog is indicated in black.

FIG. 29: *Magnaporthe oryzae* 70-15. RasGEF ETaG sequence.

```
ATGGTAATGCCCGGCGACCATTCCATGCAGCGGGCGAGCCTTCAAGTGGC
ACCCCTCGCCATCCGTAACAAGGGCTCCCGTCTCGGCCACGGCTCTGACA
CCGAGAACGATGCTTCTTTCACGTCAGTCTCGAGCAACAACAGTGACGCC
ACCATCACGGACTCGAGGTCCGACGCAACAAACCTCAACAAGACAACAGC
AACCACCACCACCACCACAACAACAACGACCACCACGAGCACAACCAAGA
AACCAAACGCCGCGATCGATTCGTCCAACGGCTCCCACATGAAGTCGTCG
TCGCGCAATGGCTCGCGAGAGGAACCGCTGGAGGCGGATCCGGACATGGC
TCCGCCCGTCTTCCACAACTTCTTGCGGGCCTTCTTCCACTTCAAGCCGA
GCTTCCTCATGACGGACTCGACTGTTACACTGCCGCTGGCCGAGGGCGAC
GTAATCCTGGTGCACTCGATACACACCAATGGCTGGGCAGACGGCACCCT
GCTGGCAACCGGCGCCAGAGGCTGGCTGCCGACCAACTACTGCGAACCAT
ACGGACCCGACGAACTCACGAACCTTTTGAACGCCTTGCTTAACTTTTGG
GATCTTTTGCGTAGCACGTCGGTCAACGACCACGAGATATTCAGCAACCA
GGAGTTCATGAAGGGCATAATAGCCGGCGTCCGATACCTACTGGTAGGTT
TTTGCTCTTTGTTTTTCTTTTGTCTTTTTATGACTTTGCTTAGCCCCGAG
CCTTGCGCCTGGCGTGGGATGAAAAAAAGACCAAAAAGCCCTCCGAGGC
CTGTGCGACTGACGCTGATTAATTGGGTGGCACAGGAACGCACAAACTCT
CTTACTAGAGAGGCCCCTCTCATTCAGCGCCACGAGGGCCTCAGACGCAG
CAGGAAATCGCTATTGTCCGAGCTTAGCTCGCTGGTCAAGACGGCCAAAC
GCCTCCAGGAGCACCAGCGTATGATTCAGCCCATTGAGGACACTAACGAT
ATCATTGACGAGATGATCCTCAAGGCATTCAAGATTGTGACCAAGGGTAC
TCGCTTTCTAGACATTCTGGATGAGGACAGGAAATCTCGAGCACCATCAG
TCACGGTCATGGCAACCGTCATGGAGGAGGTGACGCCGCCCGTCGACGGA
AAGCCTGCAAATAGCGAACAGGCAAAGGCACTGCGGGCGTTGACGGCAGG
TGCAGGCGAAGACTCGTCTGCCGTGGACGACACCACGGAGCAGACGGTCG
TTGTACGTCCTACTAACAGGCGCATGTCGACCATCACATCGCCAATTTCG
GCAACCAACACGAGGAGAATGTCGCTGGGTAGCAACCCCCACCGGGTGTC
GACGGCAATCTCGCACCGAGTCTCGCTTGTCCCATCACCATCCACCAAGG
CCCAGAACCTCATCTCACAGCAATTGAGCGACAGCCACGATACCTTCCTG
TCATACCTGGGTTCGTTCATCGGCCGCCTGCACCTGCAGTCCCAGTCTAG
GCCGCATTTGGCGCTTGCCGTCAAGCAGTCGGCAACGTCGGGTGGCGAGC
TGCTGGTGGTTGTCGATGTGGTGTGCGCCCACAACCGCATGAGCCAGGAT
```

-continued

```
TTCCTTGATGCTTACCGCGATGCCATGTTTGCACGTCTCCGAGACCTTGT
CTTGGCGGCACAGGATGTCCTGACCAGCCGCGGTCGCGAGATGGAGGACG
TCATCTTTCCCCAGGACAACAGCAGACTGCTTCAGGCGGCCACGGGTTGC
GTGCGGGCCACGGGCGAGTGTGTTGCCAAGACCAAATGGTTCCTCGAAAA
GATTGGCGACTTTGAGTTTGAGCTGGAACGGGGAGCTTCGGCTCTGAACA
TGGATCTTGGCTTTTTGGAGATTAAAGTTGCCGAGGACAGGGATAAGGAC
CAGGGCATGGACGCCACCAGCATCGCCGAGTCCAACAAATCAGGCTCTAC
CGAAACCTCGACGGTAACGGCAACTACGACACAGTCCGCCGCGTCGACAA
CCGCCACGGTGCGGCCGACGGCCCTGGCCACCAACAAGCCGCTTCCTGAG
GTGCCCCAATCCACAACCCCCGACGAGGAGGCCCCGCGGCCTCAACGATC
CCCCGCTTCCTCACGACCGACCTCGCTTGTGGAGGAGGGCCCTGCCAGCA
TGGCTTCCTCTGTGGCGTCGCTGCGTCCTATGCTGCCGCCTCTGCCCAGG
CTTTCCACCTCGCTTATGACGCAGGATGAGTACAGCCCGTCGGAGCACTC
GGCTGGCCACGACAGCGACAACTACCATGGCTCGTTCCGCTCTGAGAGCA
TGACAGCCTCCAGCTCCGGAACCGGCAGCACATATATCAGCCGCGACTCG
GAGTCAAGCCTGGTCTCACAGTCGTCAACGCGTGCGACAACGCCAGACAT
TCCCTTGGCGAACCAAAAGTCGCTCTCGGATATTAGCAACTCTGGCAGCG
GAGCTTGTGTGGTTGAGGAGGATGACGTCGAGTCGAGGCTGCTCGAGAGG
ACATATGCGCACGAGCTCATGTTCAACAAGGAGGGCCAAGTTACCGGCGG
CTCACTCCCCGCTCTGGTCGAGAGGCTGACCACTCACGAGTCCACCCCCG
ACGCCATGTTCGTGTCGACCTTTTACTTGACTTTCAGGCTCTTCTGCACA
CCCGTAAAATTGGCCGAGAGCTTGATCGACCGATTCGACTACGTTGCCGA
GTCTGCTCACATGGCAGGTCCCGTTCGTCTGCGTGTCTACAACGTCTTCA
AGGGCTGGCTCGAGTCCCACTGGAGGGACGAGACGGACCGCGAAGCCCTG
AGTCTCATCGAGCCGTTTGCTACTTTCAAACTTGGCGAGGTGCTTCCCTC
GGCCGGCAAGCGTATCCTCGAGCTTGTCGATCGCGTCTCTGCGTGCGGCG
GTGGTGCATTGGTCCCACGCCTGGTGTCTTCGATGGGCAAGACCAACACA
TCCATCTCTCAATACGTTCCCGCCGACACTCCCCTGCCAAACCCGGTATT
CACCAAGAGCCACGCGCACCTGCTGGCCAACTGGAGGAACGGCGGCAGCT
GCCCTAGCATCCTCGACCTTGATGCTCTCGAGATTGCCCGGCAGCTTACC
ATCAAGCAGATGAACATCTTTTGCTCGATAATGCCCGAGGAGCTCCTAGG
CTCTCAGTGGATGAAGAATGGAGGTGCCGAGTCGCCCAACGTCAAGGCCA
TGTCGACCTTTTCCAACGACTTGTCCTCGCTGGTGTCGGACACAATCCTG
CACTACAACGAGGTCAAGAAGCGTGCAGCCGTGCTCAAGCAGTGGATCAA
GATTGCCCACCAGTGCCTGGACTTGAACAACTATGACGCCCTCATGGCGA
TCATCTGCAGTCTCAACAGCTCCACCATCACGCGCCTCCGGCGCACATGG
GAGGCCGTCTCGCCTCGTCGCCGTGAGCTCCTCAAGCAGCTCCAAGCCAT
TGTCGAGCCGTCTCAGAACAACAAGGTCCTGCGCGGTCGCTTGGCCGGCC
ACGTCCCGCCCTGCCTGCCATTCCTCGGCATGTTCCTCACCGACCTGACC
TTTGTCGACATTGGCAACCCGGCCATCAAGCAGCTCCCTGGTAACGAGGG
CGACGGCAAGGCTCCGGCCATCACCGTCATCAACTTTGACAAGCACGCCC
```

GCACGGCCAAGATCATCGGCGAGCTGCAGCGCTTCCAGATTCCTTACCGG
CTGCAGGAGCTTACCGAGGTGCAGGAGTGGATCCAGGCCCAGATTGCACG
ACTCCGCGAGCTCGAGACGCCCAACGATAACGTCCAGGTCGCCTACTACC
GCAAGAGTCTGCTGCTCGAGCCCCGCGAGGTCACGGCCACGCCCCAGACG
CTACGGAACTCGTCCGAGACGTTTTCCTCGTCGTCGGCCACGCTCGCACC
TCCAAGCGCCAGAGACTCGACCGCTGCCAACGGCAGAGCAGCAGAGAGAA
CTGCTCAGTCGCAGAGGACGGATTATTTTGGCTGGATGCGAGGATCTGGG
GGCAGCCACAGAGATCATCCTGCTGCTTGA

Figure 30:
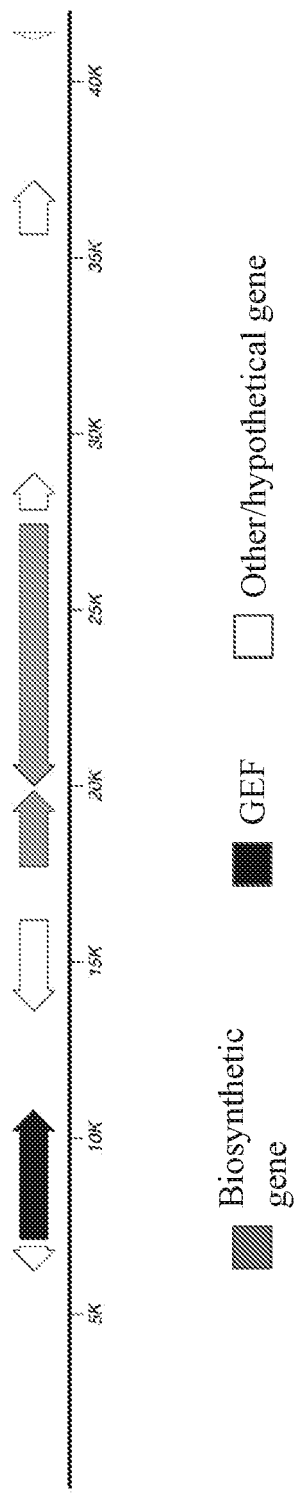
FIG. 30 depicts example biosynthetic gene clusters related to RasGEF, e.g., from *Arthroderma gypseum* CBS 118893. Illustrated RasGEF homolog is indicated in black.

FIG. 30: *Arthroderma gypseum* CBS 118893. RasGEF ETaG sequence.

ATGGCTGCTCGCGATGGCTACTCCAGCCAGGGCGCTGCTGGTGCGGCGAA
TGACGATGGTCTGTACCAAAATTTACTTCCTCTTCTTCCGGTTCTACCCA
CGTCGTATTAACCGCATTTCACAGGCTACGTATCACCAACAGAGGCGCCT
CCGGCTCTCTATGTTAGAGCTCTGTACAAGTACACCTCAGACGACCACAC
CAGCCTTAGCTTCGAGCAAGGCGACATTATTCAGGTGCTGAATCAGCTCG
AGACCGGCTGGTGGGACGGTGTGATTGGTGATGTCCGTGGCTGGTTCCCA
AGTAACTACTGCGCTGTCGTTCCTGGGCCCGAGGCTCTCAACGAGCACGC
CGGTGATGCCAGTGCCGAATCTGGCGCAGACGATGACTACGAGGACGACG
TTGACGGCCTTGACACTACCCTGAGAGACGACGACCTGCCTATTGAAAGC
AATGGAGCAGACGGCGGCGAGCCCGAAGAGGCCGCCTTCTGGATCCCCCA
GGCCACCGCAGACGGGCGCCTGTTCTACTACAACACATTGACCGGCTACA
GCACAATGGAACTTCCCCTGGAGACGCCGACTTCCGTCAACGAGTCTGGC
CCTCGGGACCGTACAAACGTCTACGTGCCCGAACACACCAGGCTGCCACC
TGAGATGATGGCCCGTGGCATCGATCGCTACGAAGATGACTATGATGGCT
CTGCCTCAGAGGCTGAAGGTGACTCCCTCTTAATGGCATCGCAGCGCCGA
CATTCGTTCATTTCTGATGGCGTCTCTCCTGCTACATCCTTAGGTTCCGT
CAATCCTTCACCAATCACCAAACACTATGATCTCAAATCAGCTTATCCTC
CCCATTTCGTTGCAAACGGTGGAAACGCTGGCATGGACTCTATCCCTATC
ATGGGCACTCCCATGTCCACCCACTCGAACGCGACTGATCGATCTCTGCC
CTTTGGCATCTCAACCTCTATCCCTCGCTATTTCCTGGATGACTCCACCG
CTCCTCATCCTACCTGGAACTCGTCGTCAGCAACATGCGAGATGCAATT
GAGGCGTATCGACAGGCCATCATCGAAGGTCGGCGGTCAGAGTACGTTCG
CAGGGCCGAGGATGTGTCCGATCACCTGCGGATGCTTCTCGCGGCAGGCT
CCGATACTACAGATAACCACTCGGGCAACCCGTCAATCATCTCTACAAAC
AAGGCGCTATACCCGCATTTCCGCGATATGATGTCCAAATTCTCCAAGCT
CGTCCTATCCTCACATATTGCCGCGGCTGACTGGCCGGGACCAGACTCTG
CGACCAAATGTCTCCATGAAGCCGAGGGCGTTCTACAGGGCGTTTACGGC
TACGTCGAAGTGGCCAAGCAGCAGCGAGGAGACGATATCCGCCGTCTGAC
ACCTGGCTTTGTCGCCGGCAGCACTTCTGGCGGTCACTGGCAGAACAACA
ACCTCGCTCGAAGGGATCCAACGTCTTTCCTCGAGCATGACTCTGAGTCT
CACCGCACTCCGTCGGTCTCGCTTGACTCAAAGCTTCTAGAGCGAATCGA
AGAGCTTCGCAAGATGCTAGCTGTCAGCTCCCGCAGGCTAGAAGAGCAGC
TCTCATCCTTCAAGGGTAAAATTGTTACGCCAAAAAGCCATGCCGAGATT
GGCGACGCTGTATGTGAAGCTGGCGTGCCGATAGTCGAAAACTTTCGCCC
GTGGGTGGCGCTCATCGAGTCTATCGACTTGTCACACTTTGGCTCTGATC
TCCAGAACCCGCAATTAGCGGACTTCAGCGTTCAGAAGCAGCGCGTGTAC
GACAGCATCTCGGACCTCGTTATGAGCTGCCAGCACATCTCTGCTCCGCT
AGGCGACGAGTGGGCCGAGATCAGGGGCGATTCGCTTGAGACTCGTCTAA
ATAATACCCGCATGATGTCAAGGCAGCTCACTAATTGCGTTCAACAGATT
GGATTCTCGTTGACCTTACTATTGGAACAAGCTCCACAACAACAAATACA
AAATGGAGATGGATATAACAAATCTGCTCCCAAGGTACGCAAGAGTCCGC
CATCATCTATTGGCATACCTTCCAGCTATGGCGTGGGCGATGACCATGAT
AAGCCACCACGGTCTCTGGATAAGGCGCAGCGGTTCTTTGGCCAACCCGT
GCCGAGGGAGCCGACTTCTGCCAGAGAACCCGAGGAAACACCGTGGTTCC
TGAAACTCGACCATGAGGCCGAGGTGTTTTACGACGTCAAGGGTGACGTG
CAGCAGCTCAAGTGCGGTACGCTGGCAGGACTAGTTGAACAGCTTACCCG
CCATGACAAGCTTGATCCCTCCTTCAAGGATACCTTCCTTCTCACATACC
GGTCCTTCACCACGGCTTCGGAGCTTTTTGAGATGGTGGTACATCGCTTC
ACACTCCAGCCTCCCTACGGCCTGACCAAAGCAGAGCTACAAATCTGGAC
CGAACAAAAGCAAATACCCATCCGGATCCGTGTCGTCAACATCCTCAAGA
GTTGGTTCGAGAACTTCTGGATGGAACCAAATGATGAGGCAAACACACAT
TTACTTGGCCGTATACACTCCTTCGTTACCGAGGCAGTTGCATCGACTAA
GACGCCTGGCGCGCAACAACTAGTCAGTTTGATAGAGCAACGCCTACGTG
GAGAAGAAACTACCGCCAAACGCCTGGTACCCACCATTAGCTCCAATGCA
CCCACTCCCATCACACCCAAGAACATGAGGAGGATCAAGTTCTTGGATAT
CGACCCAACGGAGTTTGCGCGCCAGTTGACTATCATCGAGTCGCGGCTGT
ATGCTAAGATTAAGCCTACGGAGTGTTTGAATAAGACCTGGCAGAAAAAG
GCTGGACCAGGCGAGGCCGAGCCGGCGCCGAACGTCAAGGCTCTTATTCT
ACATTCTAACCAGCTTACCAACTGGGTGGCTGAGATGATTTTGACCCAGT
CGGACGTCAGGAGACGAGTCGTCGTTATCAAACACTTTGTCTCCGTTGCT
GATGTAAGTTGATTTATCTTCTTACCCCCTTAACACATAAAAATTATGCT
AACAAATTTGATAGAAATGCCGACAACTTAACAATTATTCTACTTTGACA
TCTATTATCTCTGCGCTTGGCACCGCGCCAATCCATCGACTGGCTCGTAC
ATGGGCGCAAGTCAGCCAGAGAACCGCTGGAACCCTCGAGATGATCCGCA
AACTCATGGCTAGCACAAAGAACTTTGGCGAATACCGTGAAACCCTTCAC
CTAGCCAATCCCCCTTGCATTCCTTTCTTCGGTAACGACAATTTCCTATT
TTTTTTTATCGGCGCAGAGCCACTAACACACGCACAGGTGTCTACCTAAC
GGATCTTACCTTCATCGAAGACGGCATTCCCTCACTCACTCAATCCGATC
TAATCAACTTCAACAAACGCACCAAGACCGCGGAGGTGATCCGCGATATC
CAGCAGTACCAGAATGCGCCTTACCAGCTCATTCCCGTGCCGGAGCTGCA

-continued

```
GGAGTACGTGCTGAATAATATGCAGGCTGCAGGCGATGTGCACGACATGT
ACGACCGCAGTCTTGAAATCGAACCCCGAGAAAGGGAAGACGAGAAAATC
GCAAGGTATGGTAAACACTACTACGACCCATCGGTCGTTGCACTCTCCCT
GACGGTTGGCATACATTGA
```

Figure 31:
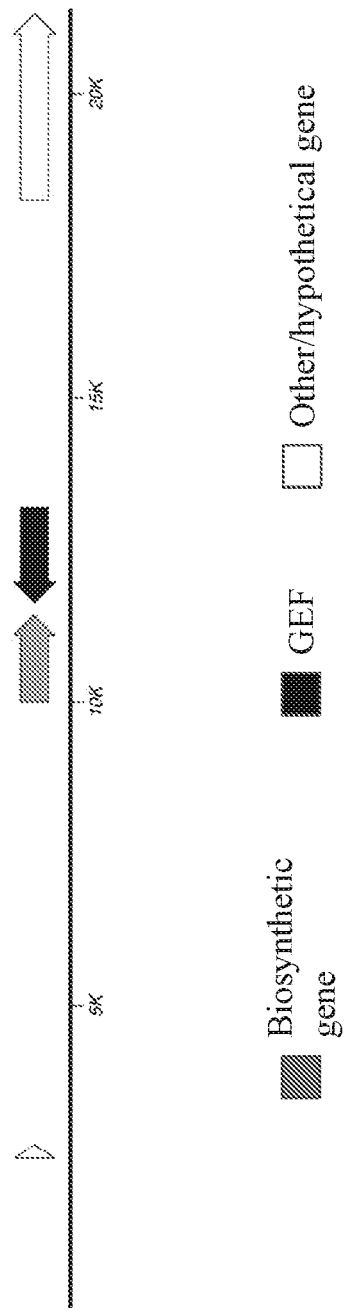
FIG. 31 depicts example biosynthetic gene clusters related to RasGEF, e.g., from *Endocarpon pusillum* strain KoLRI No. LF000583. Illustrated RasGEF homolog is indicated in black.

FIG. 31: *Endocarpon pusillum* strain KoLRI No. LF000583. RasGEF ETaG sequence.

```
ATGGAGGAGAATGACGGAGAGAGCAGGAAGCTTCTCGACAGGATCTACT
CATTTGCTAAAGACTCAATTGCCACGACCAAGACACCAGGCTCAGGACCT
TTGATGGCGGTGGTTGAGCAGAGGCTGAAGGGTCAGGACACTTCTGCTAA
AAGACTTGTGCTAACATTGACGAATTCTGCTCCCGCCCCGATCTTGCCAA
AAAATATGAAGAAGCTCAAGTTCCTCGACATAGACGCAACAGAATTCGCA
CGACAGCTTACCATTATCGAGTCTAAGCTCTATGGAAAGATCAAACCAAC
TGAATGTTTGGGCAAGACGTGGCAGAAAAAGGTTGGTCCTGAGGAGCCCG
ACCCAGCACCCAATGTGAAGTCCTTGATCCTCCATTCCAACCAGCTCACG
AACTGGGTTGCGGAGATGATACTATCACAGTCCGAGGTTAAGAAGCGAGT
ACTCGTCATCAAGCACTTTGTTTCGATTGCAGATGTGAGTCCAGCCGTAA
ACGCCAATTCGCAAAGACTGACCCATACAGAAATGCCGCAACATGAATAA
TTTCTCAACCCTTACCTCTATTGTTTCTGCTCTGGGAACTGCTCCAATAC
ACCGGCTTAATCGAACATGGACCCAAGTCAGCCCAAAGACCATGACTTCT
CTGAGTGTGATGCGACAGCTTATGGCCAGCACCAAGAACTTTGGTGAATA
TCGGGAGAGGCTACGCCGGGCAAACCCGCCATGCATACCCTTCCTAGGTG
TTTATCTTACGGATCTGACATTCATTGAAGATGGAATCGCGTCGATCGTC
AAGAACTCCAACCTCATTAATTTTGCCAAGCGGACCAAGACGGCCGAGGT
CATTCGTGCATCCAGCAGTACCAGAACGTACCGTACTCGCTCAACCCTG
TTCCTGATCTTCAGGAGTATATACTCAGCAACATGAGAGAAGCTGGCGAT
GTACATGAGATGTATGATAAGAGCTTGCAAATCGAACCAAGGGAGCGAGA
GGATGAGAAGATCGCAAGGTGAGTGTGTACAAGGAAATCTTCACACCCCC
AACGATGCAGATGGGTCTGACTCACGTCTCTCCTCGATTATAGATTGCTG
TCTGAGTCTGGTTTCCTTTGATCCGTGAGCAGGACTCGCGATTCGCTGGT
TTCTCAACATACCTTTTGAGTTGAATAGCCGCGGGGTTTGCAGGTGCCGA
ATCTCCCTTGTCCCTAACTATGATGTCAATTCTACATAAGTACTGGGGAT
GCTACACAAGGCCGGTCCTACGTAACAAGCCATTGCATGGATACTTGGAT
GGTTGGGGGTTTTTCTGGTAGATATCTGATTCAGGCTTGGTGGCATGGTA
TTGGACGTCTGACATGAAATTGCACGAGCAAACGAGTCGATGAGACACTT
ATCTGGACATGGTCAAACATCAACGAAGCTCATGGATAGGAGCGATACTA
ATTCAGGCTGATCTCGGAGCTTGTGATGGGGAATCTGCGATATCTAGTGC
TTTTGAATATACATTTTTGTTGCTAATGCAGAATGAGTAGCTGCATTTTT
GCGCAGTCGATCGGTTTTCTAG
```

Figure 32:
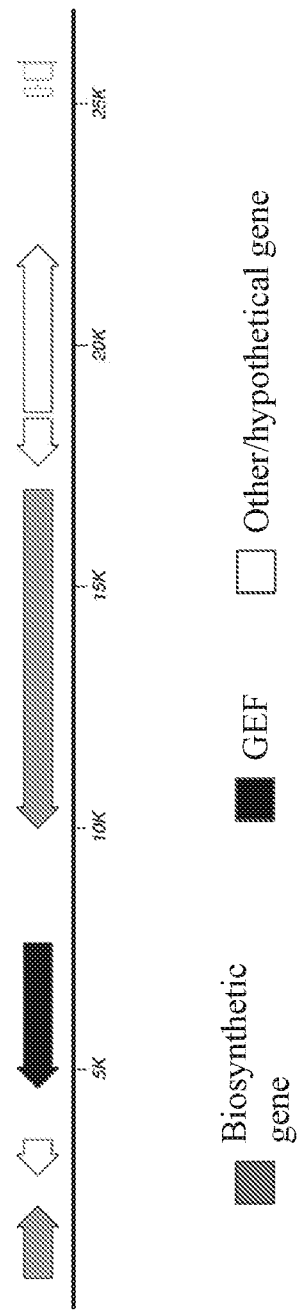
FIG. 32 depicts example biosynthetic gene clusters related to RasGEF, e.g., from *Fistulina hepatica* ATCC 64428. Illustrated RasGEF homolog is indicated in black.

FIG. 32: *Fistulina hepatica* ATCC 64428. RasGEF ETaG sequence.

```
ATGTACGATCTCGTACACGAAATTGTTGCCATTGTGTGCAAGCTACTTAC
CATCGCGGACGCTGTAATGCTGCACCCAGACATCCCGCCAAACAAAGTCA
AGAACCTCAGCCACTCAAAGAATGCGCTGTACGATTCGACGACGGCATTG
ATGGAATGTGTCCAGACGTTGACGCAACCACTCGCGCCGACGGTGACGGA
AGAGGATGAGAAGAGCGCGTTACTGGTCACCGCCACATCCGCAGTAAAGG
TTGGTGCAGACTGCGTGGCCGCGATCAAGATGTGCCTGTCGCGTTCGGTG
GGCGAACGGCCATTCGTACTGCAGCTGCCCGACAAGAATCACCCTCCTGT
GGCAGTGCCTTTACAACGACCAAAGCTCGGCAAGGCAACAAGCCTTGGCT
CGTTGAATACGTCCACTAACGTGCCTGAAGACCACGATGACACCATCCGG
CCGCCCGTACCACCACTTCCACAACAGTGTTCGCGTGATCTTTCTTCTGG
ATCGGAAAAGAGCGACGCGTCGGCACAGAGTTCGACGAGCTCACGAGACA
CAGGCTTTACGTCGTTGGACGCCTTGAAGCTGGTTTCACCGAAAGAGAAG
CCTCTGCCCGCTCTCCTTAAGCTTACAAAAGCCGCCGTCGAAAAAGATCT
CCCCTCGCCCACATCTCTTGCTCCCACTGAAGCTGCAAGTACATGGGAAG
GTGCTCCATCACATTACTTGCACTCGCTCGGTAAATCATCAACCACTTCA
TCAAATGCGGCGCTCAGCTTGCAATCTATCCACAATCCTTGCCATCACT
GCCGGCGCTTGTCAATGCACATGACTATTCCGACGACGAGGTGGCATGCA
ATAGCGAGGGACACATCGTCGGTGCAACGATGAGCGTGTTAGTGGCACGG
ATGACGCCACATGACAATCTCGTCGATGCCGCCTTCGCCGCAGTCTTCTT
CATGACGTTCCGCTTGTTTTCGTCGCCCGAAGAGCTCGTTGACACTCTGA
TAGCTCGGTACAACATCCAGCCGCCTGAATTCCTGAGTCAGGCGGACAAG
GAGTTGTGGATGCATCAAAAGGGCATGCCCATTCGACTTCGTGCGGCGAA
CCTTGTAAAGAGCTGGGTTGAAAGTTATTGGCGCCCTGGTGTTGACGATG
CAGTGTCGCAGACCATCTACGAATTTGCAGAGACTTGTGTGCATAAGACC
TTTGCGTCGGTCGCCAACCGTATTGTGGAACTGCTGGAGGTGCGGCAAAC
GACAAGTAACGCGGTAATCACGCCGAAAGGCGATCGCACACGCGACCCCG
GCATGTCAATTAACCCTCCGATTGTGAATTCGCCGTCCGAAATTCCGCGA
CCGATCGTGTCCAAACCATTGTTTGCGGCGTTGAGGAATCGGAATTTCTC
GTCGATCAGTGTGCTTGACTTCGATGCATTGGAATTGGCCCGCCAACTCA
CGCTTATGGAATGCACGCTCTATTGTGCAATACGGCCGGAGGAAGTGCTC
GAACCTGGCCAGCCGGGAAAGCCGAACATGAATGTCAAGGCGATGAGCAC
GCTGAGCACTGTTATCACAGGTTGGGTAACTGAGTCTATACTCAGTGAAC
AAGATGCGAAGAAACGGACTACGCTGGTTAAGTTCTTCGTCAAGGTCGCA
GATGTACGTGTTCGTTCTATGTCAACCGTCTGTAAAGATTTTGAACTCCT
TGTCAGAGATGTGTCTCACTGAACAATTTCAGTACCTCGTGGTCCCTTCT
AGCGGCTCTCGATTCTTCTACCATTTCACGGCTTCATCAGACCTGGACCG
TAAGTACCAAATTTGTCTCTTGTTCTCTCGTTAAAATATGATTCTTGCTT
CCAGGGCCTGCCTCAGAAGAATCGGCAACAGCTTGATGCACTTCGCAAGT
TATCGGACCGTGCTCGGAATTACCGCGAGTACAGAAATAAATTGCGGAAC
```

```
ACCGCGCCGCCAGCTGTTCCGTTCTTGGGTTTGTGCACTGTTTCTGCTCC
TTTTCGCGATGAGACGGATTAACAATGGTTTTCAGGCCTCTACCTGACGG
ATGTGACATTTTGTCGTGAGGGCAATCCCTCCACTAAACCGTCGCCTCTA
GATCCCAATAAGCAGCTCATCAACTTCAATAAATATCATAAGTTGGCGCG
AATCGTGCAAGGTATTTTCACATGCGCGTGCCGCACTATGTCATAATGCT
TGAACTTCGGTTTGCAGATATGCAGCGTTTCCAAGTGCCTTACAATTTCA
AGGCTATACCTGTTATCCAGGAATATTTGAACGTCGCGTTCGAGACTTCG
AAGAAGAACAGCGATCTTCAAGACTTGTACCGTCGTAGGCAAGTACACAG
TATGAATTCTTCTGTGGCCATAATCGCTGATGATGTGCTCAGTCTTATGA
TCGAGCCAAAGCGGCCGGTCGACACGCCACCCGCGAGCGCGAGCGATACG
CGATTGTTCCATTGGGCTTCGAAGTCCCAAACACCATCTCAGACTGTAGC
TGCTCCATTCTAGATGTCCCTGCTTATTTGTACTATTTTCACTATGTTTA
TACATGGGTTCCGTGCACACGGTTGCTCATATTTGTGTCTCTTTCTTTTT
TTTGGCGGACCCGTTCGCGTGTTTTCGATGACTTTCTCTCTCCGTCCTCG
GTGTTCACATATTAACTCGACTCTCTGTCTCTCTGTCTCTTTCGCTCTTG
TTATTCATTTCGCTTTGTTGTTAGGTTATATATACATTATATTGTCAAGC
CATCTGTACGTTCACCCATCCACTGCATTGGTTTAGCCTCACTACTTTTG
TCTGCTTGAATACACTGGTTCGTCCATCACCCGTGTCGTCTCTGGCCAGT
AGGGAAGGGAGCACGCATCGTTTCACTATACATAGGTCAGTCAGGTCGAG
TCTTTCTTCTTCTGGGTTCATCCCTCAGGTCATGAGGTGCGTCATGCAGC
GACTTGTTATTCTCAATCTGATTATGGTCAGTTATATCAGCGGTGAAACT
CTTCACGAATAG
```

Figure 33:
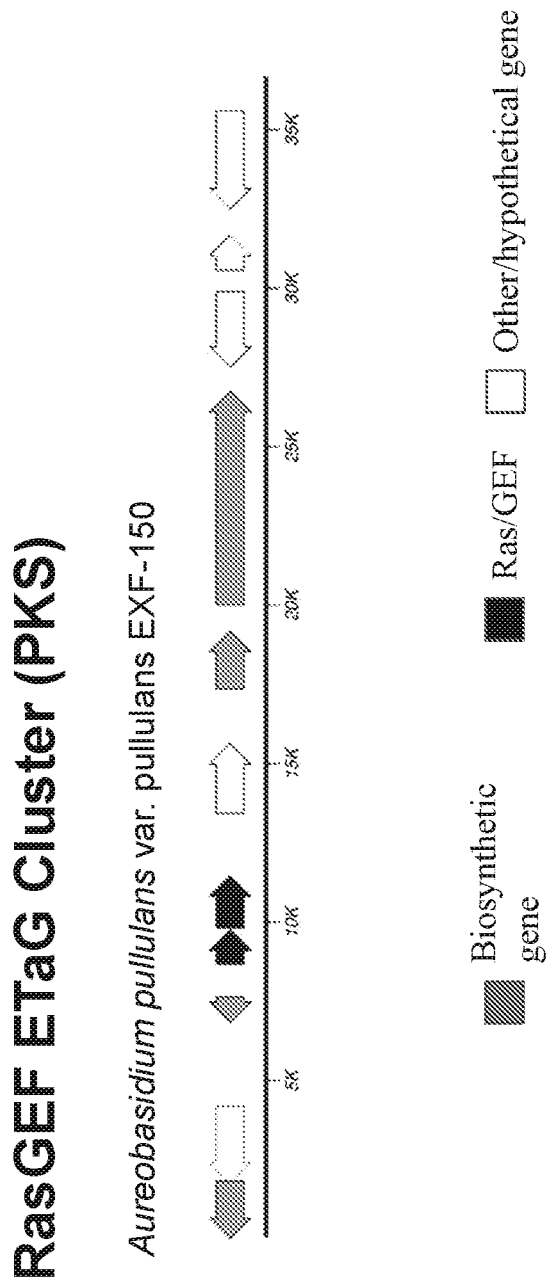
FIG. 33 depicts example biosynthetic gene clusters related to RasGEF, e.g., from *Aureobasidium pullulans* var. *pullulans* EXF-150. Illustrated RasGEF homolog is indicated in black.

FIG. 33: *Aureobasidium pullulans* var. *pullulans* EXF-150. RasGEF ETaG sequence.

```
ATGGTGACAACCCCTTCAGCCTCCACAAATCCGCCCCTCGACATTGACAC
GAATTTGGACGAATCACGCGACGACATTACAGACTCATCTCGTTCTGAGC
ACGCCTCCTCATCTGAGGATGGCGGTCTTGATGTCGATAGTCAATCAGAG
GCCCCATCCGATGAGCGGGGATACTCCTTTGACAACCTCGTCGACCGTCT
CCTGGGGCTACCGCGATCAAAAGCCGACACACGATTCGGCTCTGTCTTTC
TTGCCCTCTATCGGAAATTCGCTGCACCCGGACAGTTGCTGGAAGCTATA
GTTCATCGCTTCGAAGCCTTGGAAAAAGAAAACTGTCCTTTCATGACAAA
GACTGTCTCACAATTACGCTACTTATCTGTCATTGAGCAATGGATTGGAA
CATACCCTGGAGACTTTGCACACACAAAAACCCGCCGTCGCATGCGCATC
TTCGTCGCCAAGCTGTCCAACACACGCATCTTCTCTGCTGCCGCTCGTGA
GATGAGCTGTGACTTGGACGTTGTGACAGAAGACGATGATACAAATTGGG
CTTGTTGTGACATGGATCGTGAAAAACGCGGTCTCCTGAGCCCCGATCTC
GGCTGGTCATCCCGTGTGAGCACACTCCTGGACGATCCCGAATTTGACTT
TAGCGACAACCTGGGAAGCCTGTCTCTCGATGGCGGCCAGGGTAGAAATG
CAGCCCATTCCTTACATACCGACTTTGGCATGCTGCAGACCGTGGACGCA
GCACGTAGACAAGGCCCATCTCTGGTTCCCGTCCCCAAGATTCCAATCAG
CAAGATGCATTGGCACATGCTTATGGAAACACCAACGGATCACATCGCTT
GCGAACTGACACGCATTGACTGGATCATGTTCAGTGCAGTACGTCCGCGT
GATTTGGTGCGGCACGTTTCCTTATCGCAAACTCAGAAGGCACAGTGCAA
ATCCATAGTACATGTCAGCCGCATGATCGACCATTTCAATCACATTCGAG
ACTGGGTGGCCAACTTCATCTTGCTTAGAGAGAAGGCGAAACACCGTGTA
CTGATGTTGGAAAAGCTCATGCATGTCGCCCGTAAGCTGCGAGAGATGAA
CAACTACAACTCGCTGGGGGCGTTCCTTGCCGGTATCAGCAGTGCAGCCG
TACACCGACTTGCCGCTACTCGAGAACTGGTTTCACCCGAGACCGGCAAG
GATTGGATGAAGCTGGAGATATTGATGTCTCCCACTCGCTCTTATTCTGC
TTATCGCCTGGCTTGGGAGAACTCAAGCGGAGAGAGAATCCCTTTCCTCC
CTCTACCCATCCGAGATCTTGTGGCCGCCGAGGAAGGCAACAAGACCTTT
GTCGGCGACGAAGTGAATGGCAGAATCAACTGGCGCAAGTTCGAAGTCAT
GGGAGAAACGGTCGTCGGGATTCAAAAGGCGCAAGGTCTGCCTTATAGGA
ACTCCATGCTCGGCCCTAGGAATGATGAGTTGAGAGCATTGATCCTGAAC
AGTAACATGATCAGAGATGACGAGGTAAGTTCTTCAGAGATCAAGGTATT
TGCAGACACACGACTAACTGAATCTTCCAGGCTCTTTATGACCGTAGCTG
TTCTCTCGAATCTACCAACGACAGAAGGGGGCTGCGAGATATCTTCAGAC
GCGCATAG
```

Figure 34:
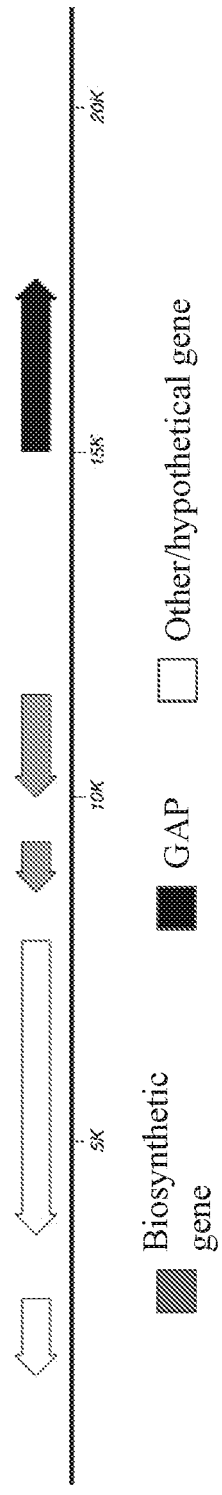
FIG. 34 depicts example biosynthetic gene clusters related to RasGAP, e.g., from *Acremonium furcatum* var. *pullulans* EXF-150. Illustrated RasGAP homolog is indicated in black.

FIG. 34: *Acremoniumn furcatum*. RasGAP ETaG sequence.

```
ATGTCTGTGATGCTGCAAGCTCCTTCCCGAGCCTCCACTGCATCCTCCTC
CTCCATCCAGCCCCTCTCCCGACAGAACACCATGTCTTCCTACGATGGCT
CGCGGTCCGCCCGCCAGTCGAAGCGGTACTCCATGTCCGCGCTGTACATG
TCCATGTCAGCCAACGACGGAGAGCTCGAGATCGAAGACGATCTGGCCAA
AGGTAGGCTACATGCATTCCCAGTTGCACTACGACTGGATTCTCTCGCTA
ACACGCTCAAAACACAGCCCAGAAAATCCTGCGAGAACTCAAGTCCAAGA
TCTCCTCCCAGTCCAAGAAGAACTTCGTCCTCGAGAAGGATGTTCGATAT
CTCGACTCTCGAATCGCCCTTCTCATCCAGAACCGCATGGCTCTGGAGGA
ACAGAACGAAGTCGCCAGCCATCTTGAAGACGCCACAGACATGCAAGAGG
GAGCCTTCCCGAACGACGACAAGACCCAGAAATATGGCAACCTCATGTTT
TTGCTGCAGTCCGAGCCGAGGCACATCGCCCATCTGTGCCGTCTTGTGTC
CATGGCTGAGATCGACTCGCTGCTCCAGACCGTCATGTTCACGATCTATG
GAAATCAGTACGAGAGCCGCGAAGAGCACCTGCTTCTTACCATGTTCCAG
GTCCGCCTGCCTACCTGCACTATATCAGATCATTGCTAACAAGGACTTCC
AGTCTGTTCTGACCTATCAGTTCGACAACACCCCTGAGTACTCCTCGCTC
CTGCGCGCAAATACCCCGTCTCTCGCATGATGACGACATACACGAGGAG
AGGCCCTGGACAGAGTTTCCTCAAGTCTGTTCTGGCCGATAGGATCAACA
GCCTGATCGAACTGAAGGACCTCGACCTTGAAATCAACCCCTTGAAGGTG
TATGAGCGCATGATCGAGCAGATCGAAGAGGACACAGGAAGCCTACCCGC
ATCCCTGCCAAAGGGAATCACTGCTGAGCAGGCGGCGGAAAACCCTCAAG
```

-continued

```
TCCAGGCCATCATCGAACCCCGTCTGACGATGCTGACGGATCTCGCCAAT
GGCTTCTTGTCGACCATCATCGAGGGGCTCGATGAAGCTCCTTATGGGAT
CCGTTGGATTTGCAAGCAGATCCGCAGCTTGACCAAGCGCAAGTATCCTG
ATGCTAATGATCAGGTTGTTTGCACCCTCATCGGCGGTTTCTTCTTCCTG
CGCTTCATCAACCCTGCCATTGTCACGCCCAAGTCCTACATGCTCATCGA
AGGCCAGCCTGCCGAGCGACCCAGGCGCACCTTGACCTACATTGCCAAGA
TGCTCCAGAACCTGGCCAACAAGCCCTCGTATGCCAAGGAGCCGTACATG
GCGAAGCTTCAGCCCTTCATTCAGCACAACAAGGACCGGGTCAACAAGTT
CATGCTCGACCTCTGCGAGGTGCAAGATTTCTACGAAAGCCTCGAGATGG
ACAACTACGTGGCCCTGTCCAAGAAGGACCTGGAGCTGTCCATCACACTG
AACGAAATCTACGCCATGCACTCACTGATCGAGAAGCATCATGATGAGCT
CTGCAAGGACGCCAATTCTCACCTGGCAATCATCATGTCTGAACTGTCTT
CGGCCCCGGCCCAAGTCCCACGCAAGGAGAACAGGGTCGTCAACTTGCCC
CTATTCAGTCGCTGGGAGACAGCCATGGATGACCTCACTGCCGCACTTGA
CATTACGCAAGAGGAGGTGTTCTTTATGGAAGCCAAGTCCATCTTCGTAC
AGATCATGCGGTCCATCCCGTCCAACAGCAGCGTTTCTCGACGCCCCTG
```

-continued

```
CGCCTCGAGAGGATCGCTGACGCAGCAGCCACCAGCCGAAACGATGCGGT
TATGGTCCGCAAGGGCATTCGAGCCATGGAGCTGCTTTCACAGCTTCAGG
AGCTGAGGGTCATTGATAAGAGCGACCATTTCAGTCTGCTCCGCGATGAG
GTGGAGCAAGAGCTGCAGCACCTGGGGTCGCTCAAGGAAGCCGTCATCCG
TGAGACATCGAAGCTCGAGGAGGTTTTCAAGACCATTCGCGACCATAACA
CGTACCTGGTCGGCCAGCTCGAGACGTACAAAAGCTATCTTCACAACGTC
CGCTCGCAGAGCGAAGGAACGAAGAGGAAGCAGCAGAAGCAGCAGGTCCT
TGGTCCTTACAAGTTCACCCATCAGCAGCTTGAAAAGGAGGGCGTCATCC
AGAAGAGCAATGTCCCCGACAACCGACGGGCGAACATTTACTTCAACTTC
ACGAGCCCTTTGCCGGGCACTTTCGTCATTTCCCTTCACTACAAGGGTGA
GTATTCCTCATTGCCGCGCCCTCATTGATTCATGCTTACAACTGCGTAGG
ACGCAACCGAGGATTGCTGGAGCTTGATCTCAAGCTGGACGACCTTCTGG
AGATGCAGAAGGACGGGCAAGACGACCTCGACCTTGAGTACGTGCAGTTC
AATGTGCCCAAGGTCCTGGCGCTCTTGAACAAGCGCTTCGCGAGGAAGAA
GGGGTGGTAA
```

Figure 35:
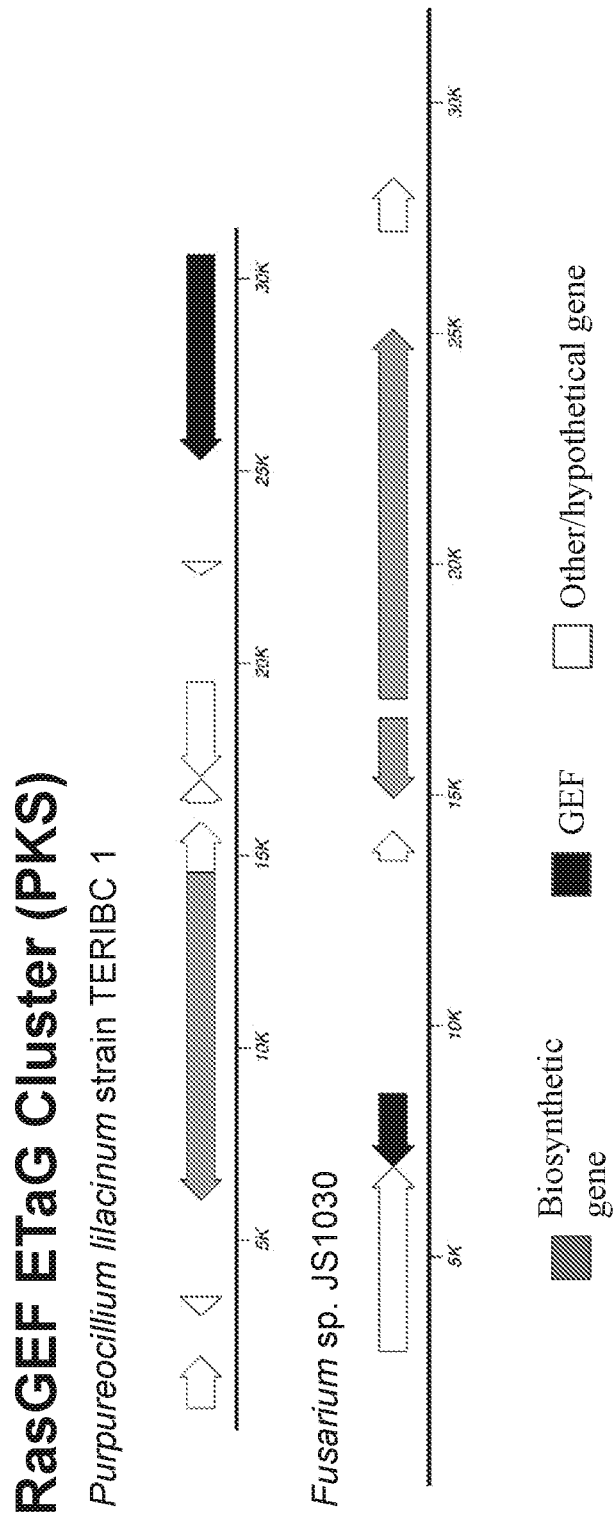
FIG. 35 depicts example biosynthetic gene clusters related to RasGEF, e.g., from *Purpureocillium lilacinum* strain TERIBC 1 and *Fusarium* sp. JS1030. Illustrated RasGEF homologs are indicated in black.

FIG. 35: *Purpureocillium lilacinum* strain TERIBC 1. RasGEF ETaG sequence.

```
ATGGTCAGGGACTCAGGGTCACGTCCAGGACGGGAAGACGTCTGGCTGTT
GGCTGTCTTTCTCGTCGCCCCAAGAAAGGGTAGGGAGTCTTGGCTGCTCCGCAGAGA
CTTGTATTTGCATGGCCGCCATCCCATCGGCGCCGTGTGTGGCATGGCACGGGTGCT
GCTGCGTGCTTCGTTCGAATGGGGTCGATGATGCCCAATTCCTCGGGGATCCTCGTC
GTGGTATATTACCTTACCTTTGCATCTACCTAATCGACGGCGGCGGCGCCAGGCAAA
TGGAAGCTGGCCGCCGGCAAGGTCACCGCCCACGGCACCCCTAATCGTCAATTACG
ACAGACGCCCGACCAACGACACCCACCTCTGTGGCCGGGGCTGCACACCCGAGTGT
AGGTTCAAGGTTGATCTTGCGTACCTCACGGAGTACAGGCGAGGTACTGCAGCGCGT
GCCTTCCTTGCCCGTGGCCGGACCGCGCCAACACCGACGAGTACCTGCCCCGTACTC
CGTGGAGTGCTCCGCGCCGTGCCTTGCTTGCCTCGAGTACAAAGCCAGGGTACTTCC
GTACATTGCCCCTCGACCAGGCCACCACCCAGACCCGCAAAAAAGACAACGACAAG
ACAACAGCGTCACCCTTCCCCTTGTCCGTGCTCCAGCAAGCCCGCTTGTCCTCGACC
GGTGCTGTCTCGCCGGCGCGCGCGCCTCGATACCATACCCTCTCTTTTCTACAATTGC
ACTCACTTTCCCCATCCGTCGGGGCTTTGCGTTTTTCGGCCCAGAATAGCCGTCGAC
GGTACTGTGCGCCATTGCCAGAGAGCTTGATCTGTTGTTGCGGCGCCAAACACCGAA
CGCTCTTTATACTTTCCTGTGCCCCTTGACCTGAACGCAGTCGCAGCGTTCTCGCCCT
TCGACCCCGGCATCGAGCTTGGAAACCGACAAGCAGCTCCCCCACAATCCTGGCCT
GCCGCTTTCTCCGCATCGCCTCGTCCGCCTTTCGTAACGACTGCTTCGTCGCCCGCGT
TCGACTCCGCCTGGCCTCGAACCTCGAGGCGCCTGCGTGTAAGTCAGTCACCTTGCG
TGCTTTGATCCTGCGGCTCAGCTGCAGCCCCCCCACCAGCAGTTTGCCCTTGCTTCAG
GTCCTGCTGTCATGTCGTCCACGCTCTCAGCAGTTCTCTTGTACTTCTTAGTTCACCC
TGCATTCCTCGCCACGCCCGCCCCGTCCCCCTCTGGCCTGCATTCCAGACACGGGTC
ATTGGCTCTTGCCACAACATCCAGGTCGCGCTCCGGCCTTGCTAACATCCAATCTCG
```

-continued

```
CCTCCAGACAAACGAGCGTCGCGTACATCTCACAACTGCTGGTTGCGCCCACCTGCG
TTGACCTGCGCCTCGGTGGTCGCGGCCGTCGTTGTCACATCCCTGGGTCCTCGCCAG
CACCAGCATACCCCCCCTCAAAAAGAACGAACTGTCACGGAACCCCCCCCTGGGGC
TCCTCCACTGCGCTCTTTGGATAACCAAAGCACTTACTTTGGAACCAGGGCGCGGCT
GGCCGTCGCTCTGGGACGGGCCGTCGACGCTAGACCGCGAGGCCTCGACCAGATGA
TCTTGACACTCGTCTCTACCTTCTCACAGGCGCAATGCTGAGCGACCAACCGTCGCG
AACTGCTTTACACGTGGCCCCGCTGGAGATACCCGCGTCGCAGCCACAGGACGGTG
CCAATGGCTTGTGCCATCAAGAACATCAGACGAATCTCTACTCACAGACCCCTATGA
CTCCGCCGGAAACACCTAACGGCTCCCAGGAGGACCTGACGCCGGAGCCTCTCGCC
CCGCCCGTCTTTCACAATTTCCTTAGGGCCTTCTACCCGTTTCACCCCGGCTACGCCT
TGTCCGACTCGAGCGTCACGCTGCCACTGGACGAAGGCGATGTCGTACTTATACACT
CTGTACACACCAATGGTTGGGCGGACGGTACTCTTTTGGCAACCGGCGCCAGGGGCT
GGCTGCCAACTAACTACTGCGATGCCTACGAGCCCGAGGATATGCGGAGCCTTCTG
AAGGCGCTTCTCAACTTTTGGGACCTCCTACGTAGCGCATCAGTAAACAATGAGATC
TTCAGGAACCAAGAATTTATGAAGGGCGTCATAGCTGGAGTTCGGTTTCTCTTGGTA
GGCTTGCGCTATCTTCTCCCCCACAAGGGCTCATTGTCTTTGCTAATGACAATGTGCT
CAGGAACGCACAAACTGCTTAAACCGAGAATCGACCATCATTCAGCGCAGTGACAG
TTTAAGGAGATGTCGCAAATCATTGCTCTCAGAACTCTCATCATTGGTCAAGACAGC
GAAGAAAACACAGGAGTGCCAAAAGGGGACACTCCACCCACCGCAGGATGTCAAC
GACATCATTGACGAGATGATACTCAAGGCATTCAAGATTGTCACCAAAGGCGTCCG
GTTTCTCGATGTTCTCGAGGACGAACGGAGGGCTCGCGCACCAGCAGCTGTCACTGT
CATGGCCACTGTCGCCGAGGAATCATACATTCCACCTACACCCCCTGCGGAGCGCTT
GGCTTTCGACGATCAAAGTTTGAACAATGGCAGCGAGACGGCTTCCCGCGGAACGG
CCGACAGTGTGGTTGGCAGCAGCGCCACTTCGGAACCCAGCGTTGCATCACTCAATC
CATGGAACAGGCGCATGTCGTCTCTGGGTGGATCTCAAGGCACGGCGGCCCAGAAT
CGATGGTCTCAAGGAAGTCTCCAACAAGTCAACCGTTTGTCCACAAGTATGGCGCAC
AGAGTCTCGCTGGCCGGCCCATCCCCGCTGTCGAGGCCTCAACATTTGGTATCGGAG
CGCCTCAACCGCAGCCATGACAAATTCCTCTCGCACCTCGGATCTTTCATTGGGCGA
CTGCACTTGCAGTCACACTCGCAACCGGAACTGGCACTCGCGATCAAGCAATCTGCC
ACATCGGGCGGTGAATTACTGGCAGTCATCGACGGTGTCTGCGAGTACAACAGCTCT
AGTGCCGCGGCGCTCGCTATTGTCCGAGATGCCATGTTTGAGCGCATTCAGATCTTG
GTCCACTCTGCCAGAGATATTTTGGCCAATGCCGCTACTGAAGGGGCCGACATAATC
CTGCCACAAGACAATGGGGTTTTGCTCATGGCAGCCACTGGTTGCGTGAAAGCCGCA
GGAGAATGCGTCGCCAAGGCCAAGGCCGCCATTGAGAGGGCGGGGACTTCGAGTT
CGAGCTGGAAGAGAACACGCTCGGGATAGACCTGAGCATCTTGGACATTGTCGTGG
ACGAGCGGGCGAGAACGCCCTCGGTAACGGATCGATCGGACCCTATGAGCAGCGTT
GCAGAATCGTTCCAGACCCCCGAATCGACTGTTCAGCCTCAAAAGCGGCCGATCGC
ACCCGCCGTCGACAAGCCGCTTCCCCAAGTACCCAGAATCACCATCCCCGCAGACTC
GCACAGTCGTCAAAGCAACTCCCCAGTGTCCTCTCGACCCCCGTCCCTCAACGAGGA
CAATGCTTCTAGCGTCGCGTCGTCTGTTTCGTCTATTCGCCCTGTTCTCCCGCCCCTC
```

```
CCTGAGGTTTCCACAACACCGCAGCCTCTGGATCGCGATGGTTCCGACACGACAACA
ATCGAGTCGGACGCCCATACCTCGAGGTTCGACGCCTTGGCGGCGTCCAGCGCGGG
CAGCAGTACCACTTACCTCAGCCGGGACTCTGAAACGAGCATGATGTCGCAGACGT
CGACGCGAGCGACGACGCCGGATCACACCTTGGTGCCTCGCAGCCAGCCCTCGATG
TCGGAGCTGAGTACGGCCGGCAGCTTCTCCCAGGCCGAAGAGGCGGATGACGTCGA
AACAAGACTTATGGAGAGGACGTACGCTCACGAGCTCATGTTCAATAAGGAAGGTC
AAGTCACTGGCGGATCGCTCCAGGCTCTGGTCGAACGTCTCACCACGCACGAGTCG
ACTCCGGACGCGGCTTTTGTCTCGACTTTCTACCTCACATTCCGACTGTTTTGCTCAC
CGGTCAGGTTGACGGAAGCGCTCATCGAACGTTTCGATTACGTTGGAGAATCGCCTC
ACATGTCGGGCCCCGTGCGTTTGAGGGTATACAATGCTTTCAAAGGCTGGCTGGAAT
CCCACTGGAAGGAGCAGACTGATCGAGACGCACTACAGCTCATGATTCCCTTTGCG
GAAGGAAAGCTGGCTTCGGTTCTGCCATCAGCGGGACGCCGCCTGTCCGAGCTGGC
CAAGCGTGTCTCCGGAGAAGGGTCTCTGGTGCCGCGGCTTGTCTCGTCAATGGGAAA
GACGAGCACGTCCATTGCTCAATTTGTCCCGGCTGATAGCCCCGTGCCGCAGCCTAT
CATTTCAAAAGCCAGCAGAATTTGCTTACGTCCTTCAAAATTGGCAGTGGGATGCC
AACCATCCTCGACTTTGACCCTCTCGAGCTGGCACGACAGATCACTCTGAGGCAGAT
GGGCATTTTCTGCTCCATCCAACCGGAAGAGCTGCTTGCATCGCAGTGGATGAAGAA
CGGTGGTGTAGATGCACCACACGTCAAGGCTATGTCAGCGCTGTCGACGGACTTGTC
GAATCTGGTGGCAGAGACCATCCTTCAGTACACCGAGATCAAGAAGCGAGCCGCTG
CCATCAAGCAGTGGATTAAGATCGCCCATAAATGCCACGAACTGCACAACTACGAC
GGGCTCATGGCCATAATTTGCAGCCTGAACAGCAGCACGATCAGCCGCCTTCGCAA
AACCTGGGACGCGATTTCTGCAAAGCGAAAGGAGGTGTTACGCGCACTGCAGGAGA
TCGTGGAACCATCTCAGAACAACAAAGTTCTGCGGACGCGACTACACGATCACGTA
CCTCCTTGCCTGCCCTTCCTCGGCATGTACCTCACGGATCTCACCTTTGTGGACATTG
GCAACCCCGCGACGAAGCAGATGTCCCTGGGCACCCAGTCGGAAGAGGACAGCACG
GGCGGCTTGACTGTTGTCAACTTTGACAAGCACAGTCGCACTGCCAAAATCATTGGC
GAGCTTCAACGTTTCCAAATCCCGTATCGGCTGGTGGAAGTGTCTGACATGCAGGAC
TGGCTGGCCGCTCAGGTGCGGCGTGTGCGCGAAGGTGACCAAGGCAACGTCCAGGT
CACTTACTATCGCAAGAGCCTGCTCCTGGAACCCCGCGAGAGCGCTTCGCGACGCG
AAGCCGAGCCGCCTACACCTGGTTCAACTGGTGTTGGCAGCTCTCGCACCGACTTGT
TTGGCTGGATGTCCCGCGACCGAAGCGGACAAACCGCTACACCAGCACCCGTATAG
```

*Fusarium* sp. JS1030. RasGEF ETaG sequence.

```
ATGCACAAGGGCACCGGTGCTGTGCAAAATTGCCTCATTGCAGCTGAAAG
GCAGTCTACAAAGCGTTTGACGACCATCGATGAAACTAGTGACGCCCGTCGTCCAA
GCTTGAGGGACGATTCACTATCCCATCCCCGACTTCATCTGAACGAGAACGCTGAGG
TGACTGGAGGCACCCTTCCGGGCCTTGTGGGCCATCTCACCTCTCGACAATCCGCAT
CCGACATCATGTTCCCGTACGCTTTCTTTCTTACATTCCGACAATTCTGCAAGCCACG
AGAGCTCGCAGAACAGCTTGTCGAGAGATTCGATAGTGCCAACGACTCTTCCTTTGC
CGAAGATACGCAGTTGAGGGTCTGCGACGGTTTCAAGCTTTGGCTCGAAATGTACTG
GCGAGTGGAGACTGACCAAGAGGCTCTACCGGTTATCAAGCCCTTTATCACATCGAG
```

-continued

CTTGTCTTCTATCATCCCAGCCGCGAGTAGGAAGCTAGCTCGGTTGATCGAGCACCT

TCCAGCTCGAGAGCCTTGTTTGTTGCCTCTAGCAGATCATGATAAACTCATAACAAC

TGTTTTTGACTCACCTAGAGTCAGGAGACATCGAGCTCAGCCTAATGATTCAGCGAC
GCATCAATGGGGCTTTTTGAGGACGCTGAGGAACAGTAAAAGCTCGTCGACTTTCCT
CAGCTTTGGCTGTATAGAGTTTGCCCGACAGTTGAGCATTGAGCAGACGACTCTATT

CTGCCGCATTCCTCCCCAAGAGTTCCTGGGTTGTGCGTGGGTATGCAAAACTGGCAA

CATGGCGCCTAATATCAGAGCAATGGTGTCTTTCACTAGTCAGCTTTCAAACCTTGT

GGTGGAAACCATTCTCGACCATCAAACGGCTCGCAAGCGGGCTGCTGCCATTAACC

ACTGGGTCAACATCGCACAGGAGTGCTCAAACTTTCGCAACTACGATGGCCTTGTGG

CCCTCCTCTCAGGCTTGGGCCACAGTGCCATTCTCCGGCTACGTCAGACATGGAATC

TGGTATCACCCAAGTACATAAACACCTTACAATTCCTTAAGACGCGTATGGACCGCT

CCGATAATCACAAATCACTTCGCGCATTATTGGAAACCCATGACAACCCATGTCTGC

CCTTTCTTGGCATGTATCTAACAGAGCTGGCTTTTGTGGAGATGGGTCAGTCTTGGAT

CGATCCGCAAAATCCTCACGACGAAACAACATCTGAGCAGCCCTTTATTGACTTTGC

TAAATATGCTCGGACGGCTAAGATTGTAAGGCAGCTTCAGCGTTTCCAGACGCCATC

CAAGTTAACAGCTCACCCTCGTCTACAAAATTGGTTGTCTTTTAAAATCTCAGAACTT

GATTGCAATAATGACCCTAAACTGGATGTTAGCTTTTTTGATAGAAGTGTGTCATTG
GAGCCGTACAGGATAAAAAAGTAGTTGTGGCCCGCTCTCTCTAAATAAAATAATCGT
AATGTCTAAAGCAGTGTTTGTTTAATCCGTGCCAGTATATGACCCTTATTTGCGGATT

CCTTGCGCTCAAATAGCCGTAAACATGCGTTCTAGTCCCCCAAGCTAGGCG

FIG. 36: *Corynespora cassiicola* UM 591. RasGAP ETaG sequence.

ATGGACCAAACAAGGCAGAGTCGGCGCAACAGGAGGGAGATTGGCGCTC
CGGAAGCAACTCAGCCTCTGCCACGCGACCAACGGCGAGACGATCGCGGCTCGTAC
AATTCGGCGACGATCCGTACCGTCACCCCCGATTCCATCCCAGAGGACAGCGTTGCC
AGCCAGACGTACACTACCTCCCCGCCCATCTCGCCGCGCTCCAACAGTACCTCCCAG
TCCGCCCGCAACAGCAACCCGCGCACCTTTGTTGCCCGCGCAAACTCGAACGACGC
AGAATACTCGCTCAGGGCTGCCCGTGAGACTCAGACTCGTCCGCGGACCAGGACCC
TGGAGGAGCGCTCAACGCGCGATCGCTCTCCGCCGAATCTATTCGTAACCAGCCGCC
ACCGCATCGGCTCGGTGCACAGCGCTGCGCCCTCCAATTTCCAGAGCCTCGAGGAGT
CGGTCGTCACCTCCATCGGCCATCCCTCTACCATATCCGCCGGCCCTACCGCCCCTCC
GCCTCGAACCTCGAGCAGCAACCGAAGCCGCATCATAAAACAGCAGGCCCAGCCGC
AACCGCCCCAGCGTGCCACCTCGCCCACCTCCTCGACCGCCGTCTCTCCCAATGCCC
AGCAGCCAGACTCGTGGGTGTCGCCTGTGCCGGCTTCAGACGCCCGCAAGGTCCTG
AAGCTCATGCGCGCCACATGCGGCAAGATGCAGGGCATGCTGGCCTTCCGCAGAGG
AGAGTCGAATCCGTGGTCGCTCTCCTACTGCTACATCAATGAGGAGGCCGGGAGCTT
GGTGTACGAGCCAAAGAGTGACACATCGTACCACAGGACGCTGGTGCCGGACCTGC
GCGGCTGTCGTGTCAAGACTGCCTACGATGCCGAGTCGTACACCGCCTACATTCACG
TTCTGGGCCACAACTCCAAGCTCGAGGTGTTTTTGCGCCCGCCCACCCAAGAAGAAT

-continued
```
TTGACTCTTGGTTTGCCGCACTTCTCTGCTGGGGCCCCATCCGCCCCAAGGGCATCC

ACAACAAGATGGCGAAGCCCCAGACGCCAATGGTGACGGAACGGCGACTCGCCGAT

AGCAGGAGACACTCCGAGGTGTCTCTGCTCAAAGAGGCGCCCATCATCAAAGTCGG

AAAGATGATCTACTGGGATACCAGCGTGACATATAGCAACACAGGAACCCCCAAGG

CCACTGGAGTCGCCAGGCCCCAAGCCTACCGGATACAAAGCCATGGCTCCCGCAGG

TGGAGAAGAGTATCGTGCACCTTGCGAGAGAACGGAGAGCTCAAGCTATACTCCGA

CACTGATGTCACTCTAGTCTCGGTCGTTCAGCTTTCCCAGCTGTCGCGGTGCGCCGTC

CAGCGCCTGGACCCATCTGTTCTGGATAACGAATTCTGCATCGCTATCTACCCGCAA

TACACCTCGACGTCGACGTCATTATCACTACTACGCCCCATTTTCCTATCGCTGGAAT

CACGAGTTCTTTACGAAGTGTGGATTGTTCTGTTACGAGCATTTACCATTCCGCAACT

CTACGGCCCGAAACAGCCGACCCTAAACGACGAAGGCGCCCTCTCGCCTTCGTTCG

GTACACAAGACATGTTCCGCATGGAGCGTTCGCTACTGGTCAGAGTCATCGAGGCA

AGGTTGATACCACCGATAAGCCCCAAGGTCTCAGAAAACAGCGGGCGGCCGACGTC

CTCGGCGAATATGAACGCCGGAGGTTACTACGTCGAAGTCTTGTTGGATGGAGAAG

CGCGAGCCCGGACCATGGCCAAGAATGAGGGCAACAATCCATTTTGGCGGGAGGAA

TTTGAGTTTCTTGACCTACCTGCAGTCCTCTCAACAGCTTCTTTGCTGTTGAAGAAGC

GACCTCCGAGCCAAGCCCGCAACGACAAGAACTTTTACGAGACACAGCTCAACTCC

GAATCCTTCAACTCGGACGGTGCAGGTGGCTATGCCGGCATCTCTTTCGATCAGACA

TGCGGCAAGACAGACATCTATCTTGACGACCTGGGTCCGAATCAGGAAGTTGAGAA

GTGGTGGCCGCTTGTCAACATGTACGGCAACAGTGTCGGCGAAGTCCTCGTCAAGGT

TAGCGCTGAAGAGTGTGTCATTCTCATGGCTCGAGATTACCAGCCCATGTCGGAGCT

TCTGCATCGCTTCTCCAATGGTCTGACATTGCAGATTGCGCAGATGATCCCGAATGA

GCTCAAGAAGCTGTCAGAATACCTCCTCAATATATTTCAAGTTTCGGGCCAGGCCGG

CGAGTGGATCATGGCTCTTGTTGAGGAAGAGATTGATGGCACCCTCAAGGAAAGCC

CGGCGAGTCGTCTGCGTTTCAGCAAGAGACTGGGATCTAGCGAGTCTAGCGAGTCCT

TCGGCTCGTCGAGTGACCGCGAACTCTTTTTGAGAGACATGGGCAACAATGCTAAGC

TGGAGGCGAACTTGTTGTTCCGCGGCAACACCCTCTTGACTAAGTCCCTGGACTTCC

ACATGAAACGGCTCGGAAAGGAGTACCTGGAAGAGACTCTTAGCGAAAGACTGCGA

GAGATCAACGAAAAGGACCCCGAGTGCGAGGTGGATCCAAACAAGATCACATCCCA

AAATGAGCTTGACCGCAACTGGAGGAGACTCATCAACATCACCGAGGATCTCTGGC

GTGCCATTTACAATTCCGTCTCGCGTTGCCCCCAGGAACTGAGGCTGATCTTTCGAC

ACATTCAAGCTTGTGCCGAGGATCGTTATGCGATTTCCTCAGGACGGTCAAGTACA

GCAGCGTTTCGGGCTTTCTTTTCCTCCGCTTCTTCGTCCCAGCCGTGCTTAATCCGAA

GCTGTTCGGCTTACTGAAAGGTATGTGGTGACTTCTTGCCAACAGGTTGGGCGATAC

TAAATAATGCAGACCACCCGAAACCCAGAGCACGCAGAACATTTACACTGGTAGCC

AAGTCCCTACAGGGCCTTGCCAACATGTCATCTTTTGGTACAAAAGAGGCATGGATG

GAGCCGATGAACTCCTTCCTCTCATCGCACCGTCAAGAGTTCAAGACTTACCTAGAC

AACATCTGCTCCATCTCCTCGACAACCTCGCCTGCCCCTCCTATACCTCCTTCGTACA

GCACCCCTCTTGCGATTCTGCAGCGCCTACCACCCACTTCTCGAGAAGGTTTTCCTTC

TCTTCCGTATCTCATCGACCATGCACGCAACTTTGCTGCTCTGGTAGACCTATGGCTC

CAGAATACGAGAAGCAGCGCGCCGAATATCCAGTCAACAGATGGCGATCTTCTCCG
```

-continued

```
CTTTCACAACATCTGCGTGGCTCTACATGAACGCACAGATGATTGCCTGAACAGGGC

AGAACGTGCCGAACGTCCTAGCTCGTCGTTGAGTGTCAAATGGGAAGAGTTGGTCG

AGCAACTGCAGGGTTCTGCAAGCTTTGACAGCTCAAGGGGCGCTGCCACAAGGAAT

CGAGGAGCAACAATCAAAGAAGAGGAGAGGGAGTATCTGCCAATATCCCCGGGAA

CGTGCGACGAAATGACTAGTTCCTCGTCCACGAGCACCCCTGTGACCATGAAGCCTG

TTCGACAACCCAAGGGGCGGCATCAGCAGAACAGTTCCATATCTGCGTCTACTAATT

CAGTCGCCAGCAATAACTCAGGCACCATGACCTTTCCAAACCCCTTTGCACCAAAGA

CTGCCCGCAGTGCAGGTTATCCGCCCTCAGTAAACGATTCGGTATCCGCTTCCCAGT

CTGCATCGGCCTCCGCCAGCGCATCTGCATCCGCAAATGAGGAAACGCCACCTGGG

AGCTCCGATGGCTTGCACATGGCACCTGCCCCTGCTTATCCACAGACTCATACCCAC

CCATCCGCCTCTACGAATTCTTTCACGTATGCGAACCCCAATGCACACATTAACACG

GGGACGATGGCATCAGGAGCCCTTACACGCCCTCCTCGTAGTGCAGGCGGCCACAG

TCTGGAAAACTCCGATGCAGGAAGCACGCACGAGGAAGAGTACACTACGGCACTCC

CTGCCTTCTCCAAGGACTCGCAGAAGGAGAAGAAGGAGCGTGGCTTCCGCGGTGTT

TTGCCATTCCAACGCAAGCGTAAAGACAAGGATAAGGATAAGGACAAGGATAAGG

ACAAGGACAGGGAAAAGGATAAAGACAAAGATAAAGACAGGGAGAAGGACAAAG

ACAAGGACAAAGACAAGGAGAGGGCAAAGAAAAAGACAGGGACAAAGAGAAAG

AAAAAGACAAGGGCAAGCTCCGAGAAAGGGAACGAAGCGTGGAACGGAATGACCG

TGGTGGACACTCTGCCATGGGCGAATACCACAGCCACAGTAGCCTTCGGGGTCGAG

CGCAGAACGAAGAGTTCTGA
```

*Magnaporthe oryzae* strain SV9610. RasGAP ETaG sequence.

ATGTCTAAGAAGCATGAGCGCGGACAGAGTCTGGACATGAGCAAACTCGCCATCTT

CGAACAAGAGAAGACGGTCACACCCGCACCAGCGCCGCCGCCCAGGATGGGGAGC

TTGCGGCCAACGTCGATGCTCCTCACTCGATCTGACACGATCAACCGAGGGGGAAG

TGCCGCTGTCGCCCATGCCCATGGCCCCGCCTCGCCTCCGCCCTTGCACCATCCACA

GGCAGTCCAACTGCCCGGATCCGATCTTGAGATCCTTGGCCGCTCATCCACAAACCA

ACTTCGTACCCTCTCGAAACTTGCACAGTCTGGAGAGGCTGATGAGTTTGCCATCAC

GTCACCGGCGCAAGAGGTTGTCGGACTAAAAGGCCGCCGCAGGCTTCAGAGAGCCG

ACAGGTCAAATGCTGGCCGCCTCGGTCAGAAGTCTAGCGGATATGGGTGGGAAGGG

AGAAATTGGATGGACAAACAACGACAATTCCTTCAGGCATACGAATATCTTTGTCAC

ATCGGTGAGGCAAAAGAGTGGATCGAAGATGTTATGAACAAATCTATTGGTGAGAT

TGTGAAGCTGGAAGAGGAGCTTAGGAACGGCGAGACTCTGGCGGAGGTGGTTCAAG

CGCTGAACCCGGACCGAAGATATCGTATTTTCCGGCACCCTCGTCTACAGTACCGCC

ATTCGGACAACATTGCAATCTTCTTCCGGTACCTCGACGAGGTTGAACTACCCGACC

TCTTCCGATTTGAACTGATCGATCTTTACGAAAAGAAAAACATCCCAAAGGTCATCT

ACTGCATACATGCTCTCAGCTGGCTCTTATACCGCAAAGGAATTGTCGATTTCCGAA

TCGGAAACCTGGTTGGTCAACTTGAGTTTGAGCACCACGATCTTGAAGCTATGCAGA

AGGGCCTGGATAAGCTAGGGGCCAGTATGCCGACCTTTGGTGACATGGGCGCTGAC

-continued

```
TTTGGGGTTGAGCCGGAACCGGAACCCGAAGAAACGGAAGAGGAGCGGATAGAAA
GGGAACTTGGAGAAAATGAGGAGTCCATCGTCGAGCTGCAAGCTCAAGTACGCGGT
GCATTATTGCGAATGCGGCTTGGGGAGACAATGCAGGAACTCTGGGACTCGGAGAA
CTGGCTTGTCGACCTTCAGGCCCGGATTCGTGGTGATTTTGCGCGCCAGATCATCGA
CTACCGACTAAACATGAGGCGCTTCGCAGTGAATCTACAGAGTGCCGCACGCGGGT
TCCTCGTTCGGTCGCGGCAAGCAGAGAGAGAGTACATGTGGAAGCGCTCAGAGCCC
GCCGTTCTGAAGCTACAGAGTCTCTTCCGGGCTGCAAAGGTCCGCGATGAGGTACGA
GACGTGCGATCTCAATTGTCAGAGGCTACAGGTCCTGTACGCGAGATCCAAGCGGTT
ATGCGAGGCTTTCTCGCCCGCAAGGGTGTGCGCACCCAGGTGCAAGAGACGAGTCG
AACGTCGGGAGCCGCACCGGGTCTCCAGGCGGCCATTCGTGGTATGCTGCTGAGGA
ACAGGCTTGATCATGACAGGGCTATTCTTGCCGAGGAAGCTGTTTCGATCTGCAGCT
TTCAGGCCGCCTCCCGTGCCTTGCTCACAAGAAAACAGGTCGCCCTTCAACGGGAGT
CACTAGCAAGCTTCACGGCGCAGTGGGAGGGTCTTCAATCCGCCTCCAGGGGGATG
TTCGCCAGGAACAGCATCCATGTCACCAAGGCGGAGCTCCGGGGACACTCTCCTGC
CATTGGCCTCCTGCAGGCTTTTTCAAGGGCCGGTGCTGTACGACGTGAAACGACCCG
GGTGTTGGACGCCATCGCTGTACACGAGCCGCAGGTGGTTGAGCTTCAGGGCTTGAT
CCGCGGCGCCATTCAACGCCAACGTATTGCCGCCGACTACCAGGACCTTGAGGAAC
AAGTCCCTCAGATTACCGACCTGCAGTCTCAGATCCGTGGTATGCTCTGCCGCAAAG
AGCAAGGTGAGCTTCTTGATCAGCTCCAGAGCAACGAAGAGCAAATCATCACTTTG
CAGGCCCAGATCAGGGCTATGATCCTGCGAAACAACTTGGATGTAGTGCTGGCCGA
GCTCGAAGAGCAAGAAGGGACGATTGTGCAGCTGCAGGCTGCGGCCAGGGGTGTGA
TTGTACGCAAGAGGTTCGAGGAGAAGAAGCGTCACTTCAAGGAGAACATGTCCAAG
GTCATCAAGATCCAAAGTTTTGTTCGTGGAAAGCTCCAAGGTGAAGCCTACAAGAG
CCTCACAACAGGCAAGAGCCCGCCCGTCAGTGCCGTCAAGAACTTTGTCCATCTGCT
GAACGACAGCGATTTTGACTTCAACGAGGAGGTTGAGTTTGAGCGGATGCGCAAGA
CTGTGGTACAACAGGTGCGGCAAAACGAGATGTTGGAGCAGTACATCGACCAGCTG
GACATCAAGATCGCTCTGCTCGTCAAGAACAAGATCACTCTGGACGAGGTAGTTAG
GCACCAGAGCAACTTTGGTGGCCACACCAGCAATCTGATAGCGAACAGCTCCATCG
CTTCAGTGAACCAGTATGATCTCAAGGCCCTGAACAAGACGTCGAGGAAGAAGCTC
GAGTCATACCAGCATCTCTTCTACAACCTACAAACGCAACCGCAATATCTGGCACGC
CTGTTCCGCAGGATACGTGAGCAAGGCACGGCCGAGAAGGAGTGCAAGCGCATCGA
GCATCTCATCATGGGTCTCTTTGGGTATGCACAAAAGAGGAGAGAAGAGTACTACCT
CCTCAAGCTAATTTCTCGCTCTATCTGGGAGGAGGTTGAAGCTAGCCACATGGTACA
AGACTCACTACGTGGTAACCTCTTCTGGTCTAAGCTCCTAGGCAACTATTCGAGGTC
ACCTCGCGACAGGAAGTACCTGCGAGACCTGCTCGGCCCTCTGATTCGTGACAACAT
TATCGAGGACCCTGCTCTCGACCTTGAAAGCGATCCTCTCCAGATCTATCGATCCGC
CATCAACAACGAGGAGCTGCGGACGGGCATGCCAAGCCAAAGGCCACTCGACGTCC
CCAGGGAAGTAGCCATCAAGGATCCCGAGACGAGGGAGCTGTTCATTGATCATCTT
CGGGATCTCCGTGAGATTTGCGACCAGTTCTTGCTTGCCCTCGAAGACCTGCTTCCTC
GACTGCCATATGGCCTCAGATACATATGCCGCCAGATGTTTGATGCCTTGTGCCAAC
ATTTCAAGCGTGAGCCGCAGCACATATTGCTACAGATGGTGGGCAACTGGTTCTGGC
```

-continued

```
GCTTTTACCTGCAGCCTGCCCTGACGGCTCCTGAGAACGTCGGCGTGATGGAGAAGG

GGTTGAGCCCGCTGCAGAAGCGCAACCTGGGTGAGGTTGCCAAGGTTCTCGGCCAG

GTAGCCTCTGGCCGTCCGTTTGGCGGTGATAATATCTACCTGCAGCCATTAAACGCC

TTTGTCGCTGAGTCCATGGAGCGTTTAGGCCATATCCTGGGCGAGCTGATCTCAGTC

GCCGATGCCGAAAGTACATTTGACATTGATGAGTTCAACGACCTTTACGCCAAAAAC

CGGCCCACGCTTTATATCAAGCTTGCAGATATCTTCGCCATACACAACCTGATCTCG

TCAGACCTTCCCACTATTTGTCCCAACCGCGACGACATGCTCCGGGAGATCATGCAG

GAGCTCGGTAGTGCCAAGAACAACGAGAGTGAGATGACGGCTACCGGCTCGTCCGA

CATCCAGATGTTCCTCACTCCCAAGCTGCACGATGTCGAAGATCCCGAGGCAGAGAT

CAAGGCTCTCTTCATGGAGACGAAGCGCTGCATCCTGTACATTATTCGTGTCCAGTC

AGGCTCAACCCTCCTCGAGATCCTGGTCAAGCCCGTCACGCAAGAGGACGAGCGCA

AGTGGATGGCGGTGCTGCACGACGACTTTAGTGACGGCGGGTCCACAAAGGGAGCT

TATTCCGACGTTAATATGGTCGACGTTACCCGTATGTCGTACCTCGACCTCAAGCGC

ACGGCACTCGAGAACGTCATGAGGCTGGAGCACGCCGGCAGGATCTCCAAGCACAA

CCACTACCAAGATATATTGAACGCCATTGCACTCGATATCCGGACCAAAAGCAGGA

GGAGAGTTCAGAGGCAGCGCGAGCTCGACGGGGTCCGCATGACGCTTTCTAATCTC

CACGAGAAGGCAAAGTACCTAGAGCAACAGCGCAAGAGCTACGATGACTACATTGA

GCAGGCCATGGCGACTCTGCAGAATAGGAAAGGGTAAGTCGACCTACGATACCAAC

ATGCTTCTCGTCTGAACAAGTAAAGGCTAACCTCGTTGGTTTGTTAACTTTGAACAG

CAAGAAACGGTTCCTGCTTCCATTCACAAAGCAGTACAACCACCAACGCGAGCTCG

AGCGTAGCGGCCGGGTGCCCAAGTTCGGATCGTACAAGTACAGCGCACGCCAGCTC

GCCGACAAGGGCGTACTTGTCAGCTGGGCGGGAGTGTCGGAGCGCGACCTGAGCCA

GATCAACCTCACTATCTCTTGCGACGAGGTGGGCGTATTTGTCATCGAGGGCTCGCG

TGGCCACATCCAGATCCCCGGCGCGAGTGCCCTAGTCCCTATCGAGGACCTGCTGCA

AGCCCAGTTTGAGTCGCATCAGTTCATGAACCTCTTCGAGGGCAACCTGAGGCTCAA

TGTCAATATCTTGCTGCATCTGCTTTATAAGAAATTTTATAGGACACAATAAATGGT

CGGGGCGAATTGGGGAGGGTCTAA
```

Figure 37:
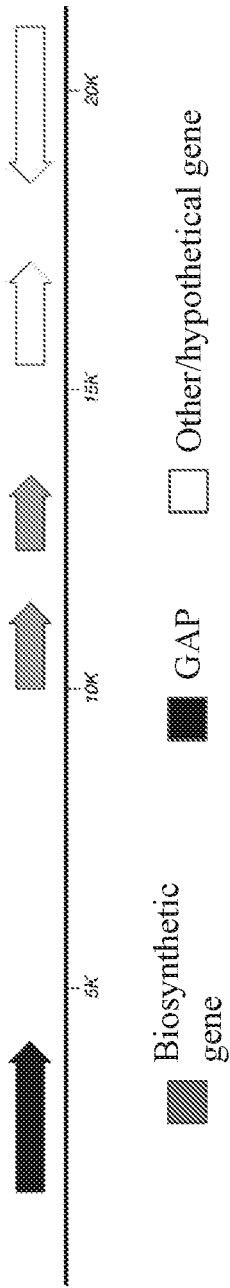
FIG. 37 depicts example biosynthetic gene clusters related to RasGAP, e.g., *Colletotrichum acutatum* strain 1 KC05_01. Illustrated RasGAP homolog is indicated in black.

FIG. 37: *Colletotrichum acutatum* strain 1 KC05_01. RasGAP ETaG sequence.

```
ATGTCCGTCATGCTCCAAACACCATCTCGAGCTTCTACCGCCTCCTCCTCCTCCTTCC

AACCCCTTTCCCGCCAAAACACCATGTCTTCTTACGATGGATCGCGGTCCGCCCGCC

AATCGAAGCGTTACTCCATGTCCGCGCTGTACATGTCCATGTCAGCGAACGAGACTG

ATCTGGAGATTGAGGATGACTTGGCCAAAGGTAGGCTCTGTAACCTCCGCAGTTTCC

TTGCCCTTTTGCCCTACTGACGATGGATTTTACAGCCCAGAAGATTCTCAGAGAGCT

CAAGTCCAAGATCTCTTCGCAGTCCAAAAAGAACTTCGTACTGGAAAAGGATGTAC

GATATCTTGATTCACGAATCGCCCTCCTCATCCAGAACCGAATGGCTCTCGAGGAAC

AGAACGAAGTCGCGAGCCACTTGGAAGACGCGACGGATATGCAAGAAGGCGCCTTT

CCTAACGACGACAAGACGCAAAAGTATGGCAACTTGATGTTCTTGTTGCAATCCGAG

CCGAGGCATATTGCACACCTCTGCCGTCTGGTGTCAATGTCGGAAATCGACTCTCTG
```

-continued

```
CTGCAGACTGTCATGTTCACCATCTACGGAAACCAATACGAGAGTCGCGAAGAACA
TCTGCTCTTGACTATGTTCCAGGTTTGTGACCCGTGACTATACTACGCGATCTGGCAA
GCTGACTCTTGACCCATTAGTCTGTTCTGACCTACCAATTCGACAACACCCCCGAAT
ATTCTTCGCTTCTGCGTGCGAACACCCCCGTCTCGAGAATGATGACCACGTATACGC
GGAGAGGACCAGGACAGAGCTTTCTCAAGTCAGTTCTCGCTGATAGAATCAACAGT
CTGATCGAGTTGAAGGATCTCGACCTGGAGATCAACCCCCTCAAGGTCTACGAGCG
CATGATTGAGCAAATTGAGGAGGACACTGGCAGTCTGCCTGCATCGCTTCCCAAGG
GCGTTACTGCTGAGCAGGCTGCGGAGAACCCCCAAGTTCAAGCCATCATCGAGCCG
CGTCTGACAATGCTCACCGAGATTGCTAATGGCTTCTTGACAACCATCATTGACGGA
CTCGACGAAGCGCCGTACGGTATTCGGTGGATTTGCAAACAGATTCGCAGCTTGACG
AAGCGCAAGTACCCTGATGCCAATGATCAGGTCATTTGCACTCTTATCGGCGGATTC
TTCTTCTTGCGGTTCATCAACCCGGCAATCGTGACACCAAAGTCATACATGCTCATT
GACGGTCAGCCGGCTGATCGCCCGAGAAGAACGCTGACTTTGATTGCAAAGATGCT
GCAAAACCTTGCTAACAAGCCCTCCTACGCCAAGGAGCCATACATGGCCAAGCTGC
AACCCTTCATCTACCAGAACAAGGAGCGTATCAACAAATTCATGCTTGACTTGTGTG
AAGTTGGCGACTTTTATGAGAGCTTGGAAATGGATAACTACGTCGCACTCTCGAAGA
AGGATTTGGAACTGTCCATCACCTTGAACGAAATCTATGCCATGCATGGCCTGATTG
AGAAGCACAACGGAGAGCTCTGCAAGGACGACAACTCGCACTTGGGCATCATCATG
TCTGAGCTAGGAGGCGCACCCCCACAGGTTCCTCGCAAGGAGAACCGCGCCATCAA
CCTCCCCCTCTTTAGCCGATGGGAAACAGCGATCGACGACTTGACAGCGGCGCTCGA
CATCACGCAAGAGGAAGTGTACTTTATGGAAGCCAAGTCCGTCTTTGTGCAAATTAT
GCGATCGATCCCATCCAACAGCAGTGTTGCACGAAGACCTCTGCGACTCGAGCGGA
TTGCCGACGCCGCAGCTACGAGCCGAAACGACGCCGTGATGGTTCGCAAAGGTATC
AGAGCGATGGAGCTGCTCTCACAGCTGCAGGAACTGAAAGTCATCGATAAGAGCGA
TCAATTCGGCCTGCTGCGTGACGAAGTCGAGCAGGAACTGCAACACCTTGGATCGCT
CAAGGACGGAGTCATTCAAGAGACTGGCAAATTGGAAGAAGTCTACAAGACCATTC
GCGACCACAACAACTATCTCGTTGGCCAATTGGAGACGTACAAGAGCTACCTGCAC
AACGTGCGTTCGCAAAGCGAGGGAACCAAGCGCAAGCAGCAGAAGCAACAGGTCC
TCGGGCCTTACAAATTCACTCACCAGCAGCTGGAGAAGGAGGGTGTCATTCAAAAA
AGCAACGTCCCGGATAACCGGAGGGCCAACATTTACTTCAACTTTACCAGCCCTTTG
CCGGGAACTTTTGTTATCTCTCTTCACTACAAGGGTACGTTGCCTCGATTGGTCATTG
CGCAACTTTTACTGACTTTTGTACAGGACGCAACCGCGGTCTTCTTGAACTGGATCTC
AAGCTCGACGACCTGCTTGAGATGCAGAAAGACGGCCAGGACGACCTAGATCTGGA
GTACGTCCAGTTCAACGTCACCAAGGTTCTCACTTTGTTGAACAAGCGATTTGCGAG
AAAGAAGGGGTGGTAA
```

Figure 38:
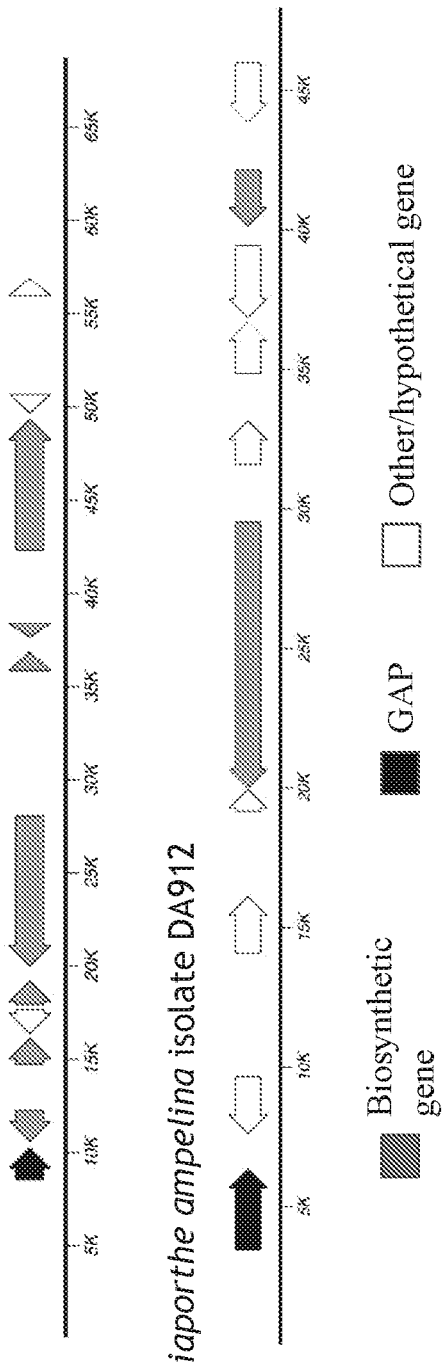
FIG. 38 depicts example biosynthetic gene clusters related to RasGAP, e.g., from *Hypoxylon* sp. E7406B and *Diaporthe ampelina* isolate DA912. Illustrated RasGAP homologs are indicated in black.

FIG. 38: *Hypoxylon* sp. E7406B. RasGAP ETaG sequence.

```
ATGACTACCTACACTAGGCGTGGACCAGGACAGAGCTTCTTGCGAACGGTACTGGC
GCAAAGAATCAACAGCCTAATTGAGTTGACAGATCTAGACCTTGAGATCAACCCCTT
GAAAGTCTATGAACGCATGTGTCAACAAATTGAAGAAGACACCGGTAGTCTTCCCC
```

-continued

```
CCTCTCTACCTAGAGGAATCACAGGCGAACAAGCTGCCGAGAATCCCCAAGTGCAA

GCCATCATAGAGCCTCGTTTAACGATGCTAACGGAGATTGCCAATGGCTTCCTGACC

ACAATTATCGAGGGCCTCGAAGAGGCTCCCTATGGCATTAGATGGATATGCAAGCA

GATTCGGAGTTTGACCAAACGAAAATATCCTGATGCGAATGACCAGGTCATTTGCAC

ACTGATCGGCGGCTTTTTCTTCCTGCGCTTTATCAATCCTGCTATCGTTACACCCAAG

TCCTACATGCTCATCGATGGAGTGCCTTCTGAACGACCACGCCGAACGTTAACCCTG

GTTGCCAAGATGCTTCAGAACTTGGCCAATAAACCATCGTATGCTAAAGAACCGTAC

ATGGCGAAGTTGCAACCATTTATCCAGCAGAACAAGGATCGTGTCAACAAGTTTATG

CTTGATCTCTGCGAGGTCCAGGACTTCTACGAGAGTCTCGAGATGGACAACTATGTT

GCACTTTCAAAGAAAGACCTAGAGCTCTCCATTACGCTGAATGAGATATACGCCATG

CACGCCTTGATCGAAAAGCACAGTGGAGAACTCTGTAGGGACGAGAACTCCCACTT

GTCACAAATCATCCAGGAGCTCGGCAAAGCACCCGCGCAGGTACCTCGGAAGGAGA

ATAGGGCGATTAATCTTCCCCTGTTTAGCCGATGGGAGACAGCTATAGATGATTTGA

CTGCCGCCCTAGATATCACGCAGGAGGAAGTGTATTTCATGGAAGCAAAGTCAATCT

TTGTACAAGTTATGCGGTCCATTCCTGCTAACAGCTCGGTTGCTCGGCGACCTCTAC

GCCTAGAGAGAATTGCTGATGCGGCTGCCACATCAAGGAACGACGCAGTGATGGTC

CGGAAAGGTATCCGGGCCATGGAGCTGCTTAGTCAACTACAGGAGATGAAGGTTAT

TGATAAGTCAGACCAGTTCAGCCTCCTGAGGGATGAGGTCGAACAAGAGTTACAAC

ATCTAGGTTCCCTGAAGGATGGTGTCATTGCCGAAACCGCGAAGCTCGAAGAGGTTT

ACAAGACGATTAGGGATCATAACTCGTACCTCGTCGGCCAGCTAGAGACTTACAAG

AGCTATCTCCACAACGTGCGAAGTCAGTCCGAAGGCACGAGACGGAAACAGCAAAA

GCAGCAAGTTCTCGGGCCTTACAAGTTTACTCACCAGCAACTAGAGAAGGAAGGCG

TCATCCAGAAGAGTAATGTTCCGGACAATAGAAGGGCTAACATCTACTTCAATTTCA

CAAGTCCTTTACCTGGAACTTTTGTGATTTCATTACACTACAAAGGTCAGTCAGAAG

GGACATTCCACTTCAGTCACGGGCTAACAAATGAATAGGACGCAATCGTGGTCTTCT

AGAACTCGACCTTAAGTTGGACGATCTGTTAGAAATGCAGAAGGACAATCAAGATG

ACTTGGACCTCGAATACGTGCAGTTCAACGTCACGAAGGTATTGGCCTTGTTAAACA

AGCGCTTTGCCAGGAAGAAGGGCTGGTAA
```

*Diaporthe ampelina* isolate DA912. RasGAP ETaG sequence.

```
ATGTCTGTGATGCTGCAAACTCCTTCCCGGGCCTCAACCGCATCCTCCTCCTCCTACC

AGGCCCTCTCCCGCCAGAACACCATGTCTTCCTACGATGGCTCGCGGTCAGCCCGCC

AATCGAAACGGTACTCCATGTCGGCATTGTACATGTCCATGTCGGCACAGGAAACCG

ACTTGGAAATAGAAGACGATCTTGCTAAAGGTTTGTTCCCAACCCCTCTCATCCAGG

CCGAAATCTTGACCGAAGTCCCATTACTTACTGTCCCCAGCCCAAAAGATACTACGG

GACTTGAAGTCCAAGATTTCCTCCCAATCCAAGAAGAACTTCGTGCTTGAAAAGGAC

GTGCGGTACCTCGACTCACGTATTGCATTGCTGATTCAGAATCGCATGGCTTTGGAG

GAGCAGAACGAAGTCGCCAGCCACTTAGAAGACGCGACAGATATTCAGGAAGGGGT

CTTTCCAAACGACGACAAGACGCAGAGATATGGCAACCTCATGTTTCTCTTGCAATC
```

-continued

```
AGAGCCCAGGCACATTGCGCATCTCTGCCGGCTTGTGTCCATGTCCGAGATCGACTC
CCTGCTGCAGACAGTCATGTTCACCATCTATGGAAACCAGTACGAGAGCCGAGAAG
AGCATCTGCTGCTAACTATGTTTCAGGTTTGCCTACCTTCTATTTCAACGTGAGTGCT
CATGCTAACTCTTGCCACCAGTCCGTTTTGACGTATCAGTTCGATAACACGCCTGAA
TATTCGTCGCTGCTTCGCGCCAACACACCAGTCTCCCGGATGATGACAACATACACG
AGGAGAGGCCCGGGTCAGAGTTTTTTGAGATCGGTGCTTGCGCACAGGATTAATGG
CCTTATCGAGCTGCACGATCTGGATCTCGAGATCAACCCCCTCAAAGTTTACGAGCG
CATGTGCGAACAAATCGAGCAGGACACGGGCAGCCTTCCGCCGTCTCTGCCAAAGG
GCATCACTGCTGAACAGGCCGCGGAGAATGCTCAGGTCCAAGCTATCATCGAGCCG
AGACTCACCATGCTTACCGAGATCGCGAATGGCTTTTTGTCGACCATCATCGACGGC
CTGGACGAAGCGCCGTACGGAATTCGATGGATCTGCAAACAAATTCGCAGCTTGAC
GAAGCGGAAGTACCCCGATGCCAACGACCAGGTCATTTGTACACTGATCGGAGGAT
TTTTCTTCCTGCGCTTCATAAACCCTGCCATCGTTACGCCGAAGTCGTACATGCTGAT
AGATGGAACACCGGCGGATCGGCCGAGGAGGACCTTGACGCTGATCGCAAAAATGC
TGCAAAACCTTGCGAACAAGCCATCCTACGCGAAGGAGCCCTACATGGCCAAGCTG
CAGCCGTTTATCCAATCGAACAAAGAACGGATCAACAAGTTCATGCTTGATCTTTGC
GATGTGCAAGACTTCTACGAAAGTCTGGAGATGGACAACTACGTGGCGCTTTCAAA
GAAGGATCTGGAGCTGTCCATAACACTGAACGAGATCTATGCCATGCACGGCCTCAT
TGACAAGCACCGGAATGAAATTTGCAAGGACGAGAACTCGCACCTACACATCATCA
TGTCCGAGCTTGGCCCTTCTCCTCCGCAGGTGCCCAGGAAGGAGAACCGGGTGATCA
ACTTACCACTGTTCAGCAGATGGGAGTCGGCCATGGATGACTTGACCGCCGCGCTCG
ATATCACCCAGGAGGAGATTTATTTCATGGAGGCCAAAAACGTATTTGTACAGATCA
TGCGTTCCATTCCATCGAATAACTCGGTTCAGCGAAGGCCTCTTCGCCTCGAGCGTA
TCGCCGATGCAGCAGCGACATCTCGGAACGACGCGGTTATGGTCCGCAAAGGTATC
CGTGCTATGGAACTGCTGAGTCAACTCCAGGAGCTGCGAGTCATAGACAAATCCGA
CCAGTTCAGCCTGCTACGAGATGAGGTCGAGCAAGAGCTACAGCATCTGGGCTCTCT
TAAGGATGCGGTCCTTGTGGAGACTTCCAAGCTTGACGAGGTCTACAAGACAATCCG
CGACCACAACACGTATCTGGTCGGCCAGCTGGAAACGTACAAGAGCTATCTGCACA
ATGTCCGCAGCCAGAGTGAGGGTACACGGCGGAAACAGCAGAAGCAGCAGGTTCTC
GGTCCCTACAAGTTCACACACCAACAATTGGAGAAGGAAGGGGTTATCCAGAAGAG
CAATGTGCCGGACAACAGGCGGGCCAACATATATTTCAACTTCACAAGCCCCCTTCC
GGGAACATTCGTGATTTCTCTGCACTACAAGGGCAAGTATAGCAGCTCGAGGGCTG
AGGACCATCCGGCATCATTCGTGAATTTATTACTGACATCCATCCCAGGGCGTAACC
GCGGGCTCTTGGAGCTTGATCTCAAGCTCGACGATCTCCTGGAGATGCAGAAAGAC
GGACAGGACGAGCTGGACCTCGAGTATGTCCAATTCAATGTGCCGAAAGTGCTCGC
CCTTCTGAACAAGCGGTTCGCTCGGAAGAAGGGTTGGTAAATAACGGATTGCCACA
CGTTATTCTGCCTTGTGTGCATCCTAGAAGATGAGGCAAGCGGTGGTCCATCCACAG
TGGCCTACTTCTTCACAACACATATCTCACGATCGATCATTCTGCCATCTCCAACATA
CAACATCATGTATCGCTAAGGGACTGTCGGCGTTTTGGGGCCGGCGTGCACTTTTAT
```

-continued
AATCCTTGATACCATCGTCTATACGCAACATCGTCTTTCAGGTCGCCCGCCTACACCT

TCACCTTTCCCCACTATATATCCCGACCGAGAGAGCCCTCTCTCGTACTGCACGCCC

CCCGCCCCCTGGGGCAGCACATCAACAGCCTCTATCAATATCTAA

Figure 39:
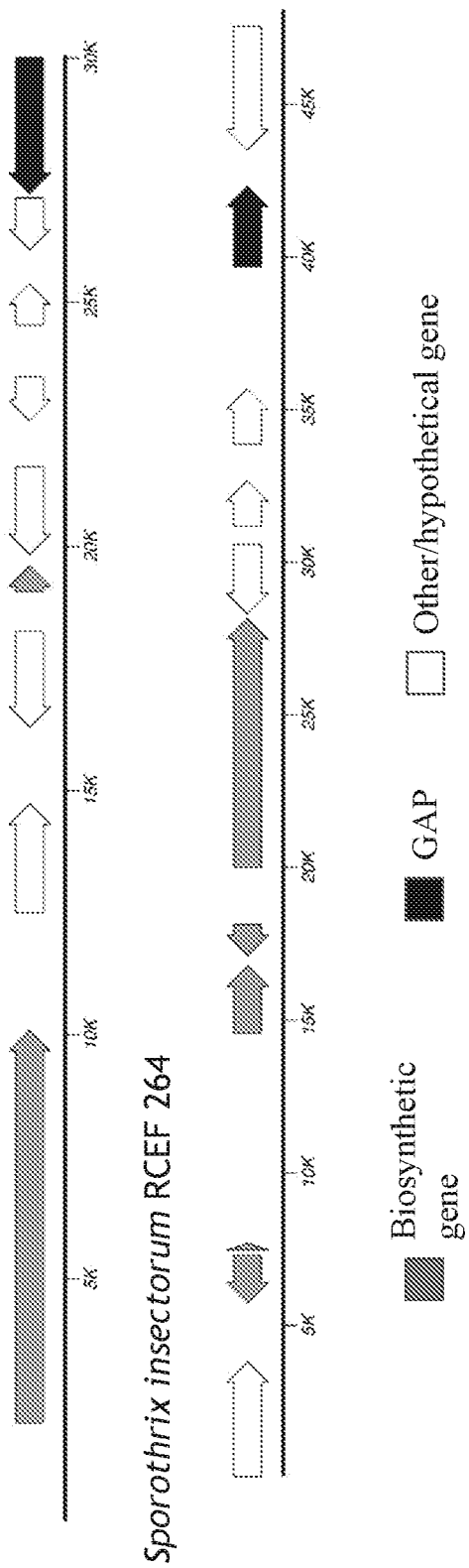
FIG. 39 depicts example biosynthetic gene clusters related to RasGAP, e.g., from *Talaromyces piceae* strain 9-3 and *Sporothrix insectorum* RCEF 264. Illustrated RasGAP homologs are indicated in black.

FIG. 39: *Talaromyces piceae* strain 9-3. RasGAP ETaG sequence.

TTCGACAACACGCCCGAGTACTCGTCGCTTCTCCGTCAAAACACCCCCGTT

TCCCGCATGATGACCACCTACACCCGCCGCGGTCCCGGTCAAAGCTACCTGAAACAT

GTCTTGGCTGAACAGATCAATACGCTCATTGACTTGCACGATGTCGATCTCGAGATC

AACCCCTTGAAGGTGTACGAAAGTATGGTGCAGCAGCTTCAGGAAGACACGGGCAG

TTTGCCCGACTACCTGCCCCGAGCAGTCACCGCCGAAGTCGCTGCCGAGAACGAGC

AGGTCCAGGCGATTATTGCTCCGCGCCTGAAGATGTTGACGGACCTTGCCAACAATT

TTCTCAACACCATCATCGAGGGGCTCGAAGATGCTCCGTACGGGATCCGCTGGATCT

GCAAACAAATCCGAAGTCTCTCCCGACGCAAGTACCCGGACGCTCAGGACCAGACC

ATCTGCACGCTTATCGGCGGCTTCTTTTTCCTTCGCTTCATCAACCCGGCCATTGTGA

CGCCTCGGTCGTACATGCTCATTGAGGCGACCCCGACCGACAAGCCCGCCGGACCT

TGACCCTGATCGCCAAGATGCTGCAGAACTTGGCCAATAAGCCGTCGTACGCCAAA

GAACCGTACATGGCCAAATTGAGCCCCTTTATCGACGAGAACAAAGACCGCGTGAA

CAAATTCTTGCTCGATCTGTGTGAAGTCCAGGACTTTTACGAGAGCCTGGAGATGGA

CAACTATGTCGCCCTGACGAAGCGGGACCTGGAGCTGCAGATCACGTTGAACGAGG

TGTATGCCACACACGCGCTGCTGGAGAAACACAGCGCCAGCCTGGCGGCTTCAGAC

CAACACTCTCACTTGCAAGCTCTTCTCCAGGAACTAGGGCCGGCACCGAGCCAGGTT

CCCCGGAAAGACAATCGCGCGATCAACCTGCCGCTGTTTAGCAAGTGGGAGACCTC

GGTCGACGATCTCACGGCGGCCCTGGATATCACCCAGGAAGAGATTTTCTTTATGGA

AGCCAAGTCGACCTTTGTCCAGATCCTGCGTTCGCTACCCTCCAACTCGGCTGTCAT

GCGGCGTCCTTTGCGGCTGGATCGCATCGCCGAGGCCGCGGCAACTCTGAAGAACG

ATGCCGTCATGGTTCGAAAGGGGATTCGTACGATGGAGCTCCTGAGCCAGCTCCAG

GAGCTGGGCGTGATTGATCGATCCGATGAGTTTGGGCTGTTGCGCGACGAAGTCGA

ACAGGAACTCGTCCATCTGGGTTCGCTCAAGGAGAAAGTGGTGCAAGAGACTCGGC

AGTTGGAGGAAGTGTACAAGACCATTCGCGATCACAACGCCTACTTGGTCGGCCAG

CTCGAAACCTACAAGTCGTATCTGCACAACGTGCGCAGCCAGTCCGAAGGCAAATC

CCGGAACAAAAAGGAGAAGAACCAGGAGCTCGGTCCGTACAAGTTTACCCACCAGC

AACTTGAAAAGGAGGGAGTCATCCGCAAAAGCAACGTGCCCGAGAATCGGCGTGCC

AACATCTATTTTATGTTCAAGAGTCCGCTGCCGGGCACATTTGTCATCAGTCTACACT

ACAAAGGTGAGCTTTCGTCCTTTTGTTTTCCTGGTTTGCTGAAGCCCCGCCCCAAACT

AACTATCACCAGGACGAGCCCGCGGTCTTCTCGAGCTCGACTTGAAACTGGACGAC

CTTTTGGAGATGCAAAAAGACAACCAAGAGGACCTTGATCTTGAATACGTTCAATTC

AACGTCACCAAAGTACTGACCCTGCTGAACAAGCGCTTTGCGCGTAAAAAGGGGTG

GTAATGGCCCCTTGACGACTTTCCATGACCCTGGCACCCCGTTGTGCTTTACCTAACC

CGTATCCTTTTGTTTTCGAAACACAGTGCTTGCGTTGTCCGTGTGAGTTCAACAGCTT

GCCATGATACCCCGCTCCGGCTCGAATTTAGTCTACATCTTGATTATGCTATTGATCG

```
TTTGCGCATACCCCTGTTGGTTTTTTGGTTCACCTGAATTGTTGGTTTGATTTTTGGAA

AATGGATTAAAAAAAGCACAAAAAAAAAGAAGAAGAAGAAGAAAAAGAGGAAAA

AAAAAAAAAAAAGAGGAAGTCAAAGTCTCCATGGGGATATCCTGTTATGGATGTCG

GGAAATGTGGTGAATTGCTTACATGACTTGCGTCCACCGTTCGCTGGCTCGAAAGGT

GTATTGTTTGTGTTTGGTGATTGTTTGCGTGTCGTGCGCTTTGGTGTTTGAGTCTCTG

GACCGTATACAGAGCGGCTTGAAGCATTTTTTGTTTGCGTGCGTTTCGATGGTTGGG

ATTGTTATGCTGATCCGACCACGTGTAATAATATATATATATATATATATATATCAAT

CATAGGCTTTCATGACAATCACTTCTTGTCTCTCCTCCCCTTGGTCCATATCGCCATA

TCTGGTCAGACCAGGGTGGCGAGCGAATCAGCACAGACAACCAAACTAGGCAAAGC

TAGTCGCAACTTTGCCGCCAACTGCAACACCAGCCACAACTGCCGCCCGCCGCTGCT

CCCCCAGCCCACTTGGCCCGATCAGCGCACGCCAGACCTTTGTTTTCTAGTTTCTCCT

CAGCTGCAATCACACTTTACCCTTCAGACCGCAACTTCAGACTTGTGTGTTCTGCAAT

TCCTTCCCTTTTCCTCTTTTCCTCGCTGTGTCCTCTATCCGCACCTGCCGGGCACAAAT

CGAATTGACCGCAGTCATCATCGACTCACCACCAGTCAATCTCGCCGGACCCCGCTA

TCCCGCTTGA
```

*Sporothrix insectorum* RCEF 264. RasGAP ETaG sequence.

```
ATGTCTGTCATGCTGCAGACGCCTTCTCGAGCCTCCACTGCCTCTTCTTCGTCCTTTC

AACCCATCTCCAGACAGAACACCATGTCGTCCTACGATGGCACGCGGTCCGCCCGCC

AATCCAAGCGGATTTCCATGTCCGCCCTCTACATGTCCATGTCGGCCAACGAAACCG

ACTTGGAGATTGAGGACGAGCTGGCCAAAGGTTGGTCCAAAGCCCCTGCCTGCTGCT

GCCTTCTGTGGACGTTTTTGTCTGGTTTGCAAACTGCCCATGATGTACTAATGCCGTG

TTCTCTTCTCCCTGCCACAGCACAAAAGAAGCTTCGCGATCTCAAAGCCAAAATCTC

GATGCAATCGAAACAGAACTTTGTCCTCGAGAAGGACGTGCGGTATCTCGATTCGA

GAATTGCCTTGCTGATTCAAAATCGCATGGCCTTGGAAGAGGTATGCATTGAAGCGG

CTGCGGATTACAGAAACAACAAATGACCCATACTCCGTTGTTGTTGATGTCGTTCTT

GTTCTCTTGTTCCCTTTCCTAACGCCAATTGTGCTTTAGCAAAACGAAGTGGCGAGCC

GTCTCGAAGACGCACTCGAATTGCAAGTCGGCGCCTTTCCGAACGACATGCAAACC

CAAAAATACGGCAACCTGATGTTCCTGCTACAGTCCGAGCCTCGGCACATTGCGCAT

CTCTGCCGCCTGGTGTCCATGTCCGAAATCGACTCACTGCTGCAGACGGTCATGTTC

ACCATCTACGGCAACCAGTACGAGAGCCGCGAAGAGCACCTGCTCCTGACCATGTT

TCAGTCTGTGCTCACCTACCAATTCGACAACACCCCCGAATACTCCTCGCTGCTGCG

GGCCAACACCCCCGTCTCGCGCATGATGACGACGTACACGCGACGCGGACCCGGCC

AGAGCTTTCTCAAGACCATCCTCGCCGACCGGATCAACAGCCTCATCGAGCTCCAAG

ACCTCGACCTGGAAATCAACCCGCTCAAGGTCTACGAGCGCATGGTCGCCCAGATC

GAAGAAGACACGGGCAGCCTCCCCGCGTCCCTCCCCAAGGGCATCACGGCCGAACA

GGCCGCCGAAAACCCACAGGTCCAGGCCATCATCGAGCCGCGCCTGACCATGCTCA

ACGAGATCGCCAACGGGTTCCTCGCCACCATCATTGACGGCCTGGAGGAGGCGCCG

TACGGCATCCGCTGGATCTGCAAGCAGATCCGCAGCCTCACGAAGCGCAAGTACCC
```

-continued
CGACGCCAACGACCAGGCCATCTGCACCCTGATCGGCGGCTTCTTCTTCCTGCGCTT

CATCAACCCGGCCATTGTCACCCCCAAGTCGTACATGCTGATCGACGGCACGCCCGC

CGACCGGCCGCGCCGGACCTTGACGCTGATCGCCAAGATGCTGCAGAACCTGGCCA

ACAAGCCCTCGTACGCCAAGGAGCCGTACATGTCCAAGCTGCAGCCCTTCATCCACC

ACAACAAAGACCGTGTCAACAAGTTCATGCTGGACCTGTGCGAGGTGCAGGATTTCT

ACGAGAGCCTGGAGATGGACAACTACGTGGCGCTGTCCAAGAAGGACCTCGAGCTG

TCCATCACCCTCAACGAGATCTACGCCATGCACGGCCTGATCGAAAAGCACAGCGG

CGAGCTCTGCAGCGACGCGAACTCGCATCTGGCCGTCATGATGGCCGACCTCGGTGC

CGCGCCCGCGCAGCTCCCCCGCAAGGAAAATCGCGTGATCAACCTGCCCCTGTTCAG

CCGCTGGGAAGCCGCGCTCGACGACCTGACGGCGGCGCTCGACATCACCCAGGAGG

AGGTGTACTTCATGGAGGCCAAGTCCATCTTTGTGCAAATCATGCGGTCCATCCCGC

AGAACTCGTCCGTGGCGCGCCGGCCCCTGCGCCTCGAACGCATCGCCGACGCCGCG

GCCACGTTCAAAAACGACGCCGTCATGGTGCGCAAGGGCATCCGCGCCATGGAGCT

ACTGAGCCAGTTGCAGGAGATGAAGGTCACCGATAAGTCCGATGGCTTCTCTCTGTT

GCGCGACGAGGTGGAGCAGGAGCTGCAGCACCTCGGCTCGCTGAAGGAGGGCGTCC

TCACCGAAACGAAGAAGCTGTCCGAGGTGTTTGCGACCATCACCGACCACAACACG

TACCTGAACGGCCAGCTCGAGACGTACAAGAGCTACCTGCACAACGTGCGCAGCCA

GAGCGAAGGCACGCGCCGGAAACCCCAGAAACAGCAGGTACTCGGCCCGTACAAG

TTCACACACCAGCAGCTAGAGAAGGAGGGCGTCATCCAGAAGAGCAATGTCCCCGA

CAACCGCCGAGCCAACATCTACTTCAACTTTACCAGTCCTCTGCCGGGCACCTTTGT

CATCTCCCTGCATTATAAAGGTAAGGCGCTCCTCTGCCGCATTTGCGTTGTCCCATTA

TGCATTTGTACGGTTTCGGTACTCACTAACGCATGCAGGGCGCACCCGGGGCCTGTT

GGAGCTGGATCTCAAACTCGACGATCTCCTGGAGATGCAGAAAAACAACTTGGACG

AGCTCGATTTGGAATACGTTCGGTTCAACGTCCCCAAGGTGCTGGCCCTGTTGAACA

AGCGCTTTGCAAGGAAGAAGGGCTGGTAG

With the identified biosynthetic gene clusters, a number of methods can be utilized to identify and characterize compounds produced by the enzymes of these biosynthetic gene clusters (e.g., those described in Clevenger, et al., Nat. Chem. Bio., 13, 895-901 (2017) and references cited therein) in accordance with the present disclosure. The compounds, once identified, can be assayed to assess their capability for modulating human Ras proteins. Additionally and alternatively, the compounds can used as lead compounds to prepare more analogs for, e.g., SAR studies, to further improve affinity, efficacy, selectivity, etc. for modulating Ras activities. It is expected that useful compounds will be developed from biosynthetic gene clusters related to the identified ETaGs.

While various embodiments have been described and illustrated herein, those of ordinary skill in the art will readily envision a variety of other means and/or structures for performing the functions and/or obtaining the results and/or one or more of the advantages described in the present disclosure, and each of such variations and/or modifications is deemed to be included. More generally, those skilled in the art will readily appreciate that all parameters, dimensions, materials, and configurations described herein are meant to be example and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described in the present disclosure. It is, therefore, to be understood that the foregoing embodiments are presented by way of example only and that, provided technologies, including those to be claimed, may be practiced otherwise than as specifically described and claimed. In addition, any combination of two or more features, systems, articles, materials, kits, and/or methods, if such features, systems, articles, materials, kits, and/or methods are not mutually inconsistent, is included within the scope of the present disclosure.

The invention claimed is:
1. A method comprising steps of:
querying a set of nucleic acid sequences, each of which is found in a fungal strain and comprises a biosynthetic gene cluster; and
identifying within at least one of the fungal nucleic acid sequences an embedded target gene (ETaG) sequence characterized in that it:
is not required for or is not involved in the biosynthesis of the product of the biosynthetic gene cluster;

is within a proximity zone relative to at least one gene in the cluster;
is homologous to a mammalian nucleic acid sequence; and
is optionally co-regulated with at least one biosynthetic gene in the cluster.

2. The method of claim 1, wherein the ETaG sequence is within a proximity zone relative to at least one biosynthetic gene in the cluster.

3. The method of claim 2, wherein a nucleic acid sequence comprising a biosynthetic gene cluster contains no more sequences beyond the nucleic acid sequences of the proximity zones relative to the biosynthetic genes of the biosynthetic gene cluster and the nucleic acid sequence of the biosynthetic gene cluster.

4. The method of claim 3, wherein a proximity zone is no more than 1, 2, 3, 4, 5, 6, 7, 8, 9, 10, 20, 30, 40, 50, 60, 70, 80, 90, or 100 kb upstream or downstream of a biosynthetic gene in the cluster.

5. The method of claim 4, wherein the mammalian nucleic acid sequence is a human nucleic acid sequence.

6. The method of claim 5, wherein an embedded target gene sequence is homologous to an expressed mammalian nucleic acid sequence in that its base sequence or a portion thereof is of at least 50%, 60%, 70%, 80%, or 90% identical to that of a mammalian nucleic acid sequence.

7. The method of claim 6, wherein the sequence or a portion thereof is at least 50, 100, 150, or 200 base pairs in length.

8. The method of claim 5, wherein an embedded target gene sequence is homologous to an expressed mammalian nucleic acid sequence in that a protein encoded by an embedded target gene or a portion thereof is homologous to that of a mammalian nucleic acid sequence or a portion thereof.

9. The method of claim 8, wherein the protein encoded by an embedded target gene or a portion thereof is of at least 50%, 60%, 70%, 80%, or 90% similarity to that encoded by a mammalian nucleic acid sequence or a portion thereof.

10. The method of claim 9, wherein a protein encoded by an embedded target gene or a portion thereof has a 3-dimensional structure that is similar to a protein encoded by a mammalian nucleic acid sequence in that a small molecule binding to the protein encoded by the embedded target gene or a portion thereof also binds to the protein encoded by the mammalian nucleic acid sequence or a portion thereof.

11. The method of claim 10, wherein the binding of the small molecule to the proteins encoded by the embedded target gene and the mammalian nucleic acid sequence or portions thereof has a Kd no more than 100 µM, 50 µM, 10 µM, 5 µM or 1 µM.

12. The method of claim 10, wherein the small molecule is a biosynthetic product of a biosynthetic gene cluster.

13. The method of claim 5, wherein a portion of the protein encoded by an embedded target gene is of at least 50%, 60%, 70%, 80%, or 90% similarity to a portion of the protein encoded by an expressed mammalian nucleic acid sequence, wherein the portion of the protein is a protein domain.

14. The method of claim 1, wherein the embedded target gene is absent from 80%, 90%, 95%, or 100% of all fungal nucleic acid sequences in the set that are from a different fungal strain and comprise a homologous or identical biosynthetic gene cluster.

15. The method of claim 14, wherein the set comprises nucleic acid sequences from at least 100, 500, 1,000, 5,000, 10,000, 15,000, 20,000, 22,000, 25,000 or 30,000 distinct fungal strains.

16. A computer system, adapted to perform a method comprising steps of:
querying a set of nucleic acid sequences, each of which is found in a fungal strain and comprises a biosynthetic gene cluster; and
identifying within at least one of the fungal nucleic acid sequences an embedded target gene (ETaG) sequence characterized in that it:
is not required for or is not involved in the biosynthesis of the product of the biosynthetic gene cluster;
is within a proximity zone relative to at least one gene in the cluster;
is homologous to a mammalian nucleic acid sequence; and
is optionally co-regulated with at least one biosynthetic gene in the cluster.

17. A method comprising steps of:
contacting at least one test compound with a gene product encoded by an embedded target gene of a fungal nucleic acid sequence, which embedded target gene (ETaG) is characterized in that it:
is not required for or is not involved in the biosynthesis of the product of the biosynthetic gene cluster;
is within a proximity zone relative to at least one biosynthetic gene in the cluster;
is homologous to a mammalian nucleic acid sequence; and
is optionally co-regulated with at least one biosynthetic gene in the cluster; and determining that:
a level or activity of the gene product is altered when the test compound is present as compared with when it is absent; or
a level or activity of the gene product is comparable to that observed when a reference agent having a known effect on the level or activity is present.

18. A method comprising steps of:
contacting at least one test compound with a gene product encoded by an expressed mammalian nucleic acid sequence, which sequence is the expressed mammalian nucleic acid sequence to which the embedded target gene sequence of claim 1 is homologous.

19. A method comprising:
identifying a human homolog of an ETaG that is within a proximity zone relative to at least one biosynthetic gene of a biosynthetic gene cluster; and
optionally assaying an effect of the product produced by enzymes encoded by the biosynthetic gene cluster, or an analog of the product, on the human homolog.

20. A method for identifying and/or characterizing a modulator of a human target, comprising:
providing a product or an analog thereof, which product is produced by the enzymes encoded by a biosynthetic gene cluster, wherein, within a proximity zone relative to at least one gene in the biosynthetic gene cluster, exists an ETaG that:
is homologous to the human target, or a nucleic acid sequence that encodes the human target; and
is optionally co-regulated with at least one biosynthetic gene in the cluster.

21. A method for modulating a human target, comprising:
providing a product or an analog thereof, which product is produced by the enzymes encoded by a biosynthetic gene cluster, wherein, within a proximity zone relative to at least one biosynthetic gene in the biosynthetic gene cluster, exists an ETaG that:

is homologous to the human target, or a nucleic acid sequence that encodes the human target; and is optionally co-regulated with at least one biosynthetic gene in the cluster.

22. The method of claim 20, wherein the human target is a Ras protein.

23. The method of claim 21, wherein the human target is a Ras protein.

* * * * *